(12) United States Patent
Ali et al.

(10) Patent No.: US 9,676,780 B2
(45) Date of Patent: Jun. 13, 2017

(54) PIPERAZINE-SUBSTITUTED [1,2,4]TRIAZOLO[1,5-C]QUINAZOLIN-5-AMINE COMPOUNDS WITH $A_{2A}$ ANTAGONIST PROPERTIES

(71) Applicants: MERCK SHARP & DOHME CORP., Rahway, NJ (US); Amjad Ali, Rahway, NJ (US); Michael Man-Chu Lo, Rahway, NJ (US); Yeon-Hee Lim, Rahway, NJ (US); Andrew Stamford, Rahway, NJ (US); Rongze Kuang, Rahway, NJ (US); Paul Tempest, Shanghai (CN); Younong Yu, Rahway, NJ (US); Michael Berlin, Flemington, NJ (US); Pauline Ting, Rahway, NJ (US); Gang Zhou, Rahway, NJ (US); Tao Yu, Rahway, NJ (US); Christopher Boyce, Rahway, NJ (US); Joseph Michael Kelly, Rahway, NJ (US); Jayaram R. Tagat, Kenilworth, NJ (US); Junying Zheng, Rahway, NJ (US); Xianhai Huang, Rahway, NJ (US); Wei Zhou, Rahway, NJ (US); Jae-Hun Kim, Rahway, NJ (US); Nicolas Zorn, Rahway (FR); Dong Xiao, Kenilworth, NJ (US); Gioconda V. Gallo, Rahway, NJ (US); Walter Won, Rahway, NJ (US); Heping Wu, Rahway, NJ (US); Rajan Anand, Rahway, NJ (US); Qiaolin Deng, Rahway, NJ (US)

(72) Inventors: Amjad Ali, Freehold, NJ (US); Michael Man-Chu Lo, Bedminister, NJ (US); Yeon-Hee Lim, Piscataway, NJ (US); Andrew Stamford, Chatham, NJ (US); Rongze Kuang, Green Brook, NJ (US); Paul Tempest, Shanghai (CN); Younong Yu, East Brunswick, NJ (US); Michael Berlin, Flemington, NJ (US); Pauline Ting, New Providence, NJ (US); Gang Zhou, Bridgewater, NJ (US); Tao Yu, Edison, NJ (US); Christopher Boyce, Flemington, NJ (US); Joseph Michael Kelly, Parlin, NJ (US); Jayaram R. Tagat, Westfield, NJ (US); Junying Zheng, New Providence, NJ (US); Xianhai Huang, Warren, NJ (US); Wei Zhou, Scotch Plains, NJ (US); Jae-Hun Kim, Scotch Plains, NJ (US); Nicolas Zorn, Durmenach (FR); Dong Xiao, Warren, NJ (US); Gioconda V. Gallo, Summit, NJ (US); Walter Won, Alpine, NJ (US); Heping Wu, Edison, NJ (US); Rajan Anand, Fanwood, NJ (US); Qiaolin Deng, Edison, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 54 days.

(21) Appl. No.: 14/655,572

(22) PCT Filed: Dec. 20, 2013

(86) PCT No.: PCT/US2013/076775
§ 371 (c)(1),
(2) Date: Jun. 25, 2015

(87) PCT Pub. No.: WO2014/105664
PCT Pub. Date: Jul. 3, 2014

(65) Prior Publication Data
US 2016/0194330 A1    Jul. 7, 2016

(30) Foreign Application Priority Data
Dec. 20, 2012    (WO) ................ PCT/CN2012/087851

(51) Int. Cl.
*C07D 487/04* (2006.01)
*A61K 31/519* (2006.01)
(Continued)

(52) U.S. Cl.
CPC ......... *C07D 487/04* (2013.01); *C07D 487/08* (2013.01); *C07D 487/18* (2013.01); *C07D 513/04* (2013.01)

(58) Field of Classification Search
None
See application file for complete search history.

(56) References Cited

U.S. PATENT DOCUMENTS

| 4,713,383 A * | 12/1987 | Francis ................ C07D 487/04 514/23 |
| 2009/0029967 A1 | 1/2009 | Grzelak et al. |
| 2012/0232086 A1 | 9/2012 | Harris et al. |

OTHER PUBLICATIONS

International Search Report—Issued on Apr. 24, 2014.

* cited by examiner

*Primary Examiner* — Michael Barker
(74) *Attorney, Agent, or Firm* — H. Eric Fischer; John C. Todaro

(57) ABSTRACT

Disclosed are compounds of Formula A: (structurally represented) where "RG1", "RG2a", "RG4", "RG5", "MG1", "n" and "m" are defined herein which compounds are antagonists of A2A receptor. Disclosed herein also are uses of the compounds described herein as antagonists of the A2a receptor in the potential treatment or prevention of neurological disorders and diseases in which A2A receptors are involved. Disclosed herein also are pharmaceutical compositions comprising these compounds and uses of these pharmaceutical compositions.

(Continued)

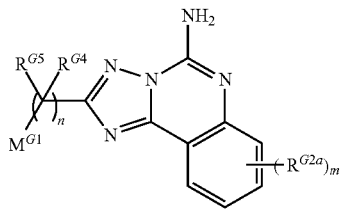
Formula A
15 Claims, No Drawings
(51) Int. Cl.
*C07D 487/08* (2006.01)
*C07D 487/18* (2006.01)
*C07D 513/04* (2006.01)

PIPERAZINE-SUBSTITUTED [1,2,4]TRIAZOLO[1,5-C]QUINAZOLIN-5-AMINE COMPOUNDS WITH $A_{2A}$ ANTAGONIST PROPERTIES

CROSS-REFERENCE TO RELATED APPLICATIONS

This application is a U.S. National Phase application under 35 U.S.C. §371 of PCT Application No. PCT/US2013/076775 filed Dec. 20, 2013, which claims priority of PCT/CN2012/087851 filed Dec. 28, 2012, each of which applications is incorporated in its entirety herein by reference.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors that belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the post-synaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds that are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

Formula PI

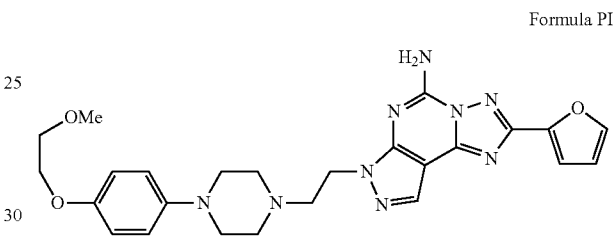

In the '475 patent, example Schemes 1 to 5, along with preparative Schemes 1 to 4, show general methods of preparing compounds of Formula PI. The '475 patent also describes that the compound of Formula I can be prepared as a pharmaceutically acceptable salt that may be useful for treating Parkinson's disease.

The use of $A_{2A}$ receptor antagonists in the treatment of central nervous system diseases, in particular Parkinson's disease, and pharmaceutical compositions comprising said compounds, has elevated the need for potent, moderately lipophilic, brain penetrant inhibitors of the $A_{2A}$ receptor. Such compounds would provide an expansion of the arsenal of compounds that are believed to have value in the treatment of central nervous system disorders, in particular treating or managing the progression of such diseases, for example, but not limited to, Parkinson's disease.

SUMMARY OF THE INVENTION

In one aspect, the invention provides one or more compounds, or a pharmaceutical salt thereof, believed to have utility as an $A_{2A}$-receptor antagonist that have the structure:

Formula A

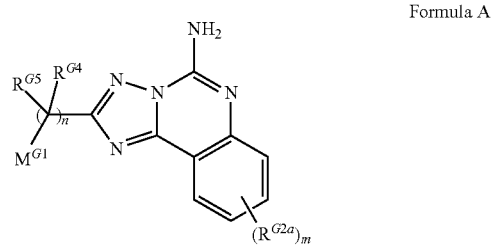

wherein:
m and n are independently an integer of from 1 to 3, with the proviso that no more than two $R^{G2a}$ substituents are located on adjacent ring carbon atoms;

$R^{G2a}$ is independently: (i) —OH; (ii) —CN; (iii) halogen (preferably —Cl or —F); (iv) —$C_{1-6}$-linear alkyl, which is optionally substituted by one or more fluorine substituents, and preferably when fluorine-substituted, is —$CF_3$; or (v) —$C_{1-6}$-alkoxy, which is optionally substituted by a $C_{1-4}$-alkoxy moiety, and preferably when so substituted the alkoxy substituent is —O—$CH_3$, and in some embodiments where $R^{G2a}$ is an alkoxy-substituted-alkoxy moiety, preferably it is —O—$(CH_2)_{1-4}$—$OCH_3$;

$R^{G4}$ and $R^{G5}$ are:
(a) independently, for each occurrence, (i) —H; (ii) —F; or (iii) —$C_{1-6}$-alkyl (linear, branched or cyclic), which is optionally substituted with one or more fluorine substituents; or,
(b) $R^{G4}$ and $R^{G5}$ are taken together to form a carbonyl [—C(O)—] moiety, with the proviso that where in >1, $R^{G4}$ and $R^{G5}$ are not selected to form two adjacent carbonyl moieties; and, $M^{G1}$ is a moiety of the formula:

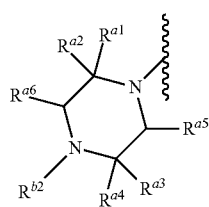

wherein substituents $R^{a1}$, $R^{a2}$, $R^{a3}$, $R^{a4}$, $R^{a5}$, and $R^{a6}$, are defined as follows:
(a) $R^{a6}$ is —H or —$CH_3$; and $R^{a1}$, $R^{a2}$, $R^{a3}$, $R^{a4}$ and $R^{a5}$ are independently:
(i) —H;
(ii) an aromatic moiety of from 6 to 10 carbon atoms; or,
(iii) —$C_{1-5}$ linear, branched or cyclic alkyl, which is optionally substituted with one or more of —F or —$C_{1-4}$-alkyl substituents, wherein one or more carbon atoms in said optional $C_{1-4}$-alkyl substituent is optionally substituted with one or more —F atoms; or,
(b) $R^{a1}$, $R^{a2}$, $R^{a1}$, and $R^{a4}$ are independently: —H, —$C_{1-5}$ linear, —$C_{3-5}$-branched or —$C_{3-5}$-cyclic alkyl; and $R^{a5}$ and $R^{a6}$ together form a bridge of the formula: —$CH_2)_q$—, providing a moiety of the structure:

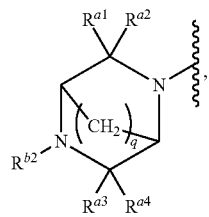

where "q" is 1 or 2, wherein q is 1 or 2;
(c) one pair of $R^{a1}/R^{a2}$ or $R^{a3}/R^{a4}$ together form an oxo-functional group, and each substituent of the other pair is hydrogen, providing a structure of Formula Ga$^1$ or Formula Ga$^2$:

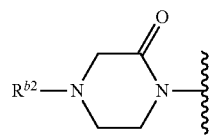

Formula Ga$^1$

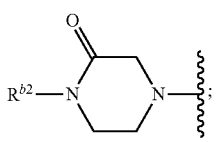

Formula Ga$^2$ (d) each of one pair of $R^{a1}/R^{a2}$ or $R^{a3}/R^{a4}$ is —H, and the other pair together comprise up to five carbon atoms which are cyclized, thereby providing a spirocycle of Formula Fb$^3$ or Formula Fb$^4$:

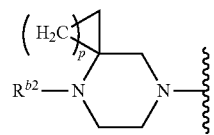

Formula Fb$^3$

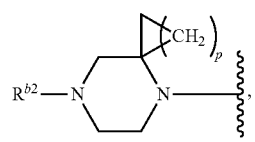

Formula Fb$^4$ wherein p is an integer from 1 to 3; or,
$R^{a1}$, $R^{a2}$, $R^{a3}$, $R^{a4}$, $R^{a5}$, and $R^{a6}$ are selected to provide an ethylene-bridged moiety of the formula:

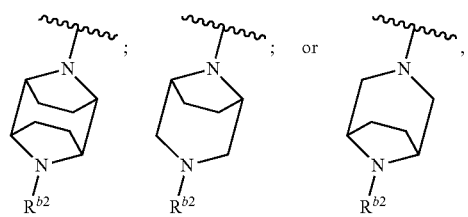

wherein:
(i) $R^{a6}$ together with one of $R^{a3}$ or $R^{a4}$ form an ethylene bridge and any of $R^{a1}$, $R^{a2}$ $R^{a3}$, $R^{a4}$, or $R^{a5}$, which are not part of said ethylene bridge are hydrogen; (ii) $R^{a5}$ together with one of $R^{a1}$ or $R^{a2}$ form an ethylene bridge and any of $R^{a1}$, $R^{a2}$, $R^{a3}$, $R^{a4}$, or $R^{a6}$ which are not part of said ethylene bridge are hydrogen; or (iii) $R^{a6}$ together with one of $R^{a3}$ or $R^{a4}$, and $R^{a5}$ together with one of $R^{a1}$ or $R^{a2}$ each form ethylene bridge, and any of $R^{a1}$, $R^{a2}$, $R^{a3}$, or $R^{a4}$ which are not selected to form an ethylene bridge are hydrogen; and $R^{b2}$ is:
(a) —$C_{1-6}$-alkyl, which is optionally substituted on one or more carbon atoms with: (i) halogen; (ii) $C_{1-6}$-alkoxy; or (iii) $C_{1-6}$-alkyl-$SO_2$—;
(b) —C(O)—$R^d$, wherein, $R^d$ is: (i) aryl; (ii) $C_{1-6}$-alkoxy; or (iii) $C_{1-6}$-alkyl;

(c) a mono- or polycyclic aryl moiety comprising from 5 to 10 carbon atoms which is optionally linked to a nitrogen of the piperazine moiety through a carbonyl carbon, thereby forming an amide linkage, and wherein the ring of said aryl moiety optionally comprises one or more substituents which are, independently:
(i) halogen, preferably F or Cl;
(ii) $C_{1-6}$-alkyl, which is optionally halogen substituted, and in some embodiments when substituted by halogen, preferably it is —$CF_3$;
(iii) $C_{1-6}$-alkoxy, preferably methoxy;
(iv) $C_{1-6}$-alkoxy-$C_{1-6}$-alkoxide;
(v) aryloxy of from 6 to 10 carbon atoms;
(vi) $C_{1-6}$-heterocycloalkyl comprising from 1 to 3 heteroatoms that are, independently for each occurrence, N, S, or O, wherein in some embodiments a -pyrrolidinyl moiety is preferable, and wherein said heterocycloalkyl may optionally include a carbonyl group (C=O), and wherein in some embodiments where said heterocycloalkyl comprises a carbonyl group, it is preferably a -pyrolidin-oneyl moiety;
(vii) $(R^{d1})_2N$—, wherein $R^{d1}$ is independently —H or —$C_{1-6}$-alkyl;
(viii) nitrile;
(ix) mono- or polycyclic heteroaryl of from 5 to 10 carbon atoms, comprising from 1 to 4 heteroatoms that are, independently for each occurrence, N, O, or S; or
(x) —C(O)—OH; or,
(d) a mono- or polycyclic heteroaryl moiety comprising from 5 to 10 carbon atoms and from 1 to 4 heteroatoms that are, independently for each occurrence, N, O, or S, which is optionally linked to the nitrogen of the piperazine moiety through a carbonyl carbon, thereby forming an amide linkage, and wherein optionally one or more ring carbon atoms is substituted with a moiety that is, independently for each occurrence:
(i) —halogen;
(ii) —$C_{1-6}$-alkyl-sulfonyl;
(iii) —$C_{1-6}$-alkyl, which is optionally substituted with one or more substituents that are, independently for each occurrence, halogen or $C_{1-6}$-alkoxide;
(iv) —$C_{1-6}$-alkoxide, which is optionally substituted with one or more substituents that are, independently for each occurrence, halogen or —$C_{1-6}$-alkyl;
(v) $C_{1-6}$—C(O)—;
(vi) —CN; or,
(vii) $C_{1-6}C(O)O$—.

In some embodiments a compound Formula A preferably has the structure of Formula AI, or a pharmaceutically acceptable salt thereof:

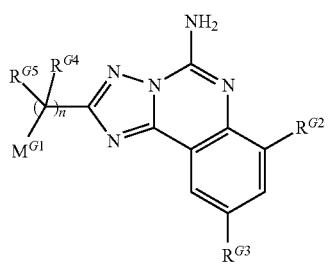

Formula AI wherein:
n, $M^{G1}$, $R^{G4}$ and $R^{G5}$ are as defined for the compound of Formula A;
$R^{G2}$ is independently:
(i) —OH;
(ii) —CN;
(iii) halogen (preferably —Cl or —F);
(iv) —$C_{1-3}$-linear alkyl, which is optionally substituted by one or more fluorine substituents, and preferably when fluorine substituted is —$CF_3$; or,
(v) —$C_{1-6}$-alkoxy, which is optionally substituted by a $C_{1-4}$-alkoxy moiety, and preferably when so substituted the alkoxy substituent is —O—$CH_3$, and in some embodiments where $R^{G2}$ is an alkoxy-substituted-alkoxy moiety, preferably it is —O—$(CH_2)_{1-4}$—$OCH_3$; and,
$R^{G3}$ is —H or —F.

In some aspects, the present invention is the provision of a pharmaceutical formulation comprising at least one compound of Formula A or a pharmaceutically acceptable salt thereof and at least one excipient. In another aspect the invention is directed to the use of compounds, and pharmaceutical formulations thereof, in the potential treatment of movement disorders in which $A_{2A}$ receptors are involved.

In some aspects, the present invention is the provision of a method of treating central nervous system disorders by administering to a patient in need thereof a therapeutic amount of at least one compound of Formula A or a pharmaceutically acceptable salt thereof.

DETAILED DESCRIPTION OF THE INVENTION

As mentioned above, one aspect the invention provides one or more compounds believed to have utility as an $A_{2A}$-receptor antagonist that has the structure of Formula A or a pharmaceutically acceptable salt thereof:

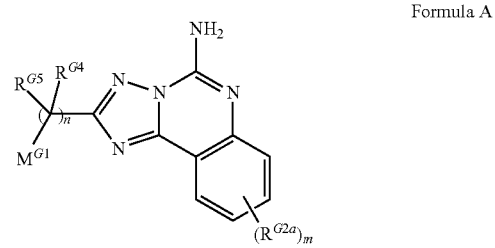

Formula A wherein n, m, $M^{G1}$, $R^{G2A}$, $R^{G4}$ and $R^{G5}$ are as defined above.

In some embodiments, compounds of Formula A preferably have the structure of Formula B or a pharmaceutically acceptable salt thereof:

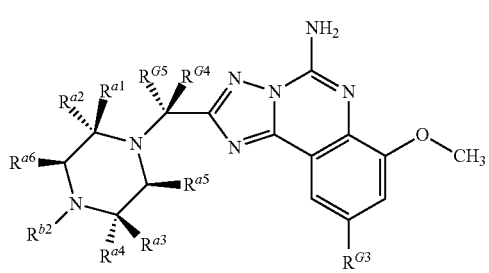

Formula B wherein:

$R^{G3}$ is —F or —H;

$R^{G4}$ and $R^{G5}$ are independently for each occurrence: —H; $C_{1-6}$-alkyl; or $C_{1-6}$-alkoxy; or $R^{G4}$ and $R^{G5}$ together with the carbon to which they are bonded represent a carbonyl moiety (—C(O)—);

$R^{a1}$, $R^{a2}$, $R^{a3}$, $R^{a4}$ and $R^{a5}$ are independently: —H; aryl; or $C_{1-5}$-alkyl; and, $R^{b2}$ is:

(a) —$C_{1-6}$-alkyl, which is optionally substituted on one or more carbon atoms with: (i) halogen; (ii) $C_{1-6}$-alkoxy; or (iii) $C_{1-6}$-alkyl-$SO_2$—;

(b) —C(O)—$R^{c1}$, wherein $R^d$ is: (i) aryl; (ii) $C_{1-6}$-alkoxy; or (iii) $C_{1-6}$-alkyl;

(c) a mono- or polycyclic aryl moiety comprising from 5 to 10 carbon atoms that is optionally linked to the nitrogen of the piperazine moiety through a carbonyl carbon, thereby forming an amide linkage, and wherein one or more ring carbon atoms is optionally substituted with a moiety that is, independently for each occurrence:

(i) halogen, preferably F or Cl;

(ii) $C_{1-6}$-alkyl, which is optionally halogen substituted, and in some embodiments when substituted by halogen, preferably it is —$CF_3$;

(iii) —$C_{1-6}$-alkoxy, preferably methoxy;

(iv) —$C_{1-6}$-alkoxy-$C_{1-6}$-alkoxide;

(v) aryloxy of from 6 to 10 carbon atoms;

(vi) $C_{1-6}$-heterocycloalkyl comprising from 1 to 3 heteroatoms that are, independently for each occurrence, N, S or O, wherein in some embodiments the heterocycloalkyl is preferably a -pyrrolidinyl moiety, and wherein said heterocycloalkyl may optionally include a carbonyl group (C=O), and wherein in some embodiments where said heterocycloalkyl comprises a carbonyl group, it is preferably a -pyrolidin-oneyl moiety;

(vii) $(R^{d1})_2$N—, wherein $R^{d1}$ is independently —H or —$C_{1-6}$-alkyl;

(viii) nitrile;

(ix) mono- or polycyclic heteroaryl of from 5 to 10 carbon atoms comprising from 1 to 4 heteroatoms that are, independently for each occurrence, N, O or S; or, (x) —C(O)—OH; or (d) a mono- or polycyclic heteroaryl moiety comprising from 5 to 10 carbon atoms and from 1 to 4 heteroatoms that are, independently for each occurrence, N, O or S, which is optionally linked to the nitrogen of the piperazine moiety through a carbonyl carbon, thereby forming an amide linkage, and wherein optionally one or more ring carbon atoms is substituted with a moiety that is, independently for each occurrence:

(i) —halogen;

(ii) —$C_{1-6}$-alkylsulfonyl;

(iii) —$C_{1-6}$-alkyl, which is optionally substituted with one or more substituents that are, independently for each occurrence, halogen or $C_{1-6}$-alkoxide;

(iv) —$C_{1-6}$-alkoxide, which is optionally substituted with one or more substituents that are, independently for each occurrence, halogen or —$C_{1-6}$-alkyl;

(v) $C_{1-6}$—C(O)—;

(vi) —CN; or, (vii) $C_{1-6}$C(O)O—.

In some embodiments, compounds of Formula A preferably have the structure of Formula C, or a pharmaceutically acceptable salt thereof:

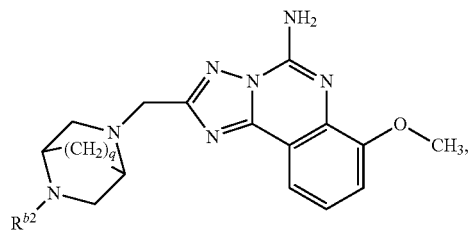

Formula C wherein q is 1 or 2 and $R^{b2}$ is:

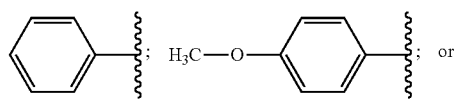

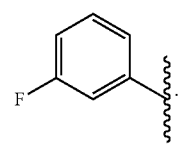

In some embodiments, compounds of Formula A preferably have the structure of Formula F, or a pharmaceutically acceptable sale thereof:

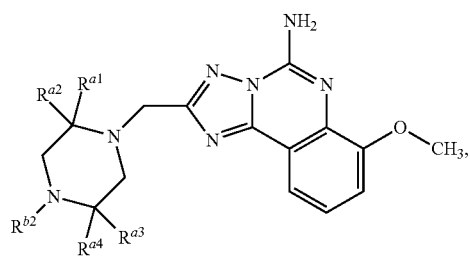

Formula F wherein each substituent of one pair of $R^{a1}/R^{a2}$ or $R^{a3}/R^{a4}$ is —H, and the other pair together form a cycloalkyl moiety of up to five carbon atoms, thereby providing a spirocycle of Formula $Fb^{3a}$ or Formula $Fb^{4a}$:

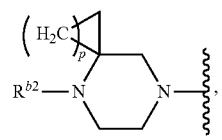

Formula $Fb^{3a}$

-continued

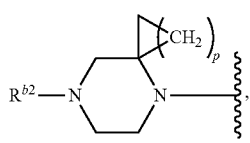

Formula Fb⁴ᵃ wherein p is an integer of from 1 to 4, and $R^{b2}$ is as defined for compounds of Formula B, above.

In some embodiments, a compound of the invention is a compound of Formula B, or a pharmaceutically acceptable salt thereof:

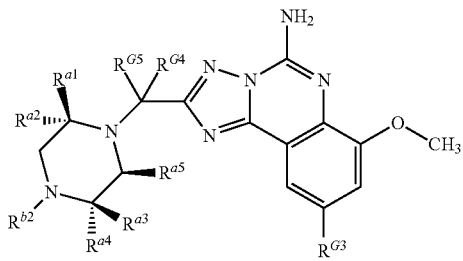

Formula B wherein, $R^{G3}$ is —H, and $R^{G4}$, $R^{G5}$, $R^{a1}$ to $R^{a5}$, and $R^{b1}$ are defined in Table I, below:

TABLE I

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-1 | —CH₃/—H/—H | —H/—H | 4-fluorophenyl | —H/—H |
| Ex-2 | —CH₃/—H/—H | —H/—H | phenyl | —H/—H |
| Ex-3 | —H/phenyl/—H | —H/—H | —CH₃ | —H/—H |
| Ex-8 | —H/—CH₃/—H | —CH₃/—H | phenyl | —H/—H |
| Ex-9 | —H/—CH₃/—H | —H/—H | phenyl | —H/—H |
| Ex-10 | —H/CH₃/—H | —H/—H | 4-fluorophenyl | —H/—H |
| Ex-12 | —CH₃/—H/—H | —H/—H | 1-ethyl-imidazol-2-yl | —H/—H |
| Ex-13 | —CH₃/—H/—H | —H/—H | 1-methyl-imidazo[4,5-c]pyridin-2-yl | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
| --- | --- | --- | --- | --- |
| Ex-14 | —CH₃/—H/—H | —H/—H | 1-ethyl-1H-imidazol-5-yl-methyl | —H/—H |
| Ex-15 | —CH₃/—H/—H | —H/—H | 6-methylimidazo[2,1-b][1,3,4]thiadiazol-5-yl-methyl | —H/—H |
| Ex-16 | —CH₃/—H/—H | —H/—H | oxazol-2-yl-methyl | —H/—H |
| Ex-17 | —CH₃/—H/—H | —H/—H | thiazol-2-yl-methyl | —H/—H |
| Ex-18 | —CH₃/—H/—H | —H/—H | (6-methylpyridin-2-yl)methyl | —H/—H |
| Ex-19 | —CH₃/—H/—H | —H/—H | (3-fluoropyridin-2-yl)methyl | —H/—H |
| Ex-20 | —CH₃/—H/—H | —H/—H | (3,5-dimethoxyphenyl)methyl | —H/—H |
| Ex-21 | —CH₃/—H/—H | —H/—H | (2,4-difluorophenyl)methyl | —H/—H |
| Ex-22 | —CH₃/—H/—H | —H/—H | (3-phenoxyphenyl)methyl | —H/—H |
| Ex-23 | —CH₃/—H/—H | —H/—H | (3,4-difluorophenyl)methyl | —H/—H |

TABLE I-continued
| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-24 | —CH₃/—H/—H | —H/—H | 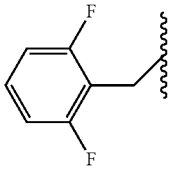 [SMILES: *Cc1c(F)cccc1F] | —H/—H |
| Ex-25 | —CH₃/—H/—H | —H/—H | 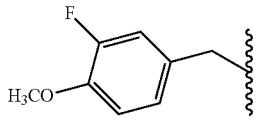 [SMILES: *Cc1ccc(OC)c(F)c1] | —H/—H |
| Ex-26 | —CH₃/—H/—H | —H/—H | 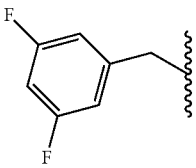 [SMILES: *Cc1cc(F)cc(F)c1] | —H/—H |
| Ex-27 | —CH₃/—H/—H | —H/—H | 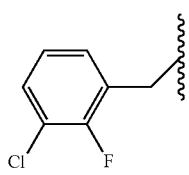 [SMILES: *Cc1cccc(Cl)c1F] | —H/—H |
| Ex-28 | —CH₃/—H/—H | —H/—H | 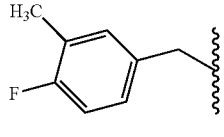 | —H/—H |
| Ex-29 | —CH₃/—H/—H | —H/—H | 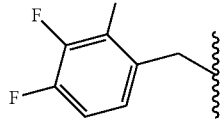 | —H/—H |
| Ex-30 | —CH₃/—H/—H | —H/—H | 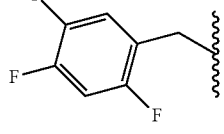 | —H/—H |
| Ex-31 | —CH₃/—H/—H | —H/—H | 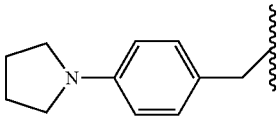 [SMILES: *Cc1ccc(N2CCCC2)cc1] | —H/—H |
| Ex-32 | —CH₃/—H/—H | —H/—H | 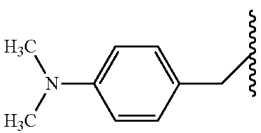 | —H/—H |
| Ex-33 | —CH₃/—H/—H | —H/—H | 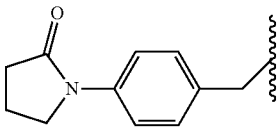 [SMILES: *Cc1ccc(N2CCCC2=O)cc1] | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-34 | —H/—CH₃/—H | —H/—H | 4-Cl-phenyl | —H/—H |
| Ex-35 | —CH₃/—H/—H | —H/—H | 4-Cl-phenyl | —H/—H |
| Ex-36 | —CH₃/—H/—H | —H/—H | 2,5-dimethylphenyl-CH₂— | —H/—H |
| Ex-38 | —CH₃/—H/—H | —H/—H | pyridin-2-yl | —H/—H |
| Ex-39 | —CH₃/—H/—H | —H/—H | 5-fluoropyridin-2-yl | —H/—H |
| Ex-40 | —CH₃/—H/—H | —H/—H | 5-(trifluoromethyl)pyridin-2-yl | —H/—H |
| Ex-43 | -cyclopropyl/—H/—H | —H/—H | 4-F-phenyl | —H/—H |
| Ex-44 | -isopropyl/—H/—H | —H/—H | 4-F-phenyl | —H/—H |
| Ex-45 | —CH₂CH₃/—H/—H | —H/—H | 4-F-phenyl | —H/—H |
| Ex-46 | —CH₂CH₃/—H/—CH₃ | —H/—H | 4-F-phenyl-C(O)— | —H/—H |
| Ex-47 | —CH₃/—H/—H | —H/—H | 2-CF₃-phenyl | —H/—H |
| Ex-48 | —CH₃/—H/—H | —H/—H | 4-CF₃-phenyl | —H/—H |
| Ex-49 | —CH₃/—H/—H | —H/—H | 5-fluoropyridin-2-yl | —CH₃/—H |

TABLE I-continued

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-50 | —CH₃/—H/—H | —H/—H | 4-fluorophenyl | —H/—CH₃ |
| Ex-51 | —CH₃/—H/—H | —H/—H | thiazol-2-yl | —H/—H |
| Ex-52 | —CH₃/—H/—H | —H/—H | 5-methyl-1,2,4-oxadiazol-3-yl | —H/—H |
| Ex-53 | —CH₃/—H/—H | —H/—H | 5-cyclopropyl-1,2,4-oxadiazol-3-yl | —H/—H |
| Ex-54 | —CH₃/—H/—H | —H/—H | 1H-tetrazol-5-yl | —H/—H |
| Ex-55 | —CH₃/—H/—H | —H/—H | 3-(trifluoromethyl)phenyl | —H/—H |
| Ex-56 | —CH₃/—H/—H | —H/—H | 2-fluorophenyl | —H/—H |
| Ex-57 | —CH₃/—H/—H | —H/—H | 3-fluorophenyl | —H/—H |
| Ex-58 | —CH₃/—H/—H | —H/—H | 2-chlorophenyl | —H/—H |
| Ex-59 | —CH₃/—H/—H | —H/—H | 3-cyanopyridin-2-yl | —H/—H |
| Ex-60 | —CH₃/—H/—H | —H/—H | 3-cyanophenyl | —H/—H |
| Ex-61 | —CH₃/—H/—H | —H/—H | 4-cyanophenyl | —H/—H |

TABLE I-continued
| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-62 | —CH$_3$/—H/—H | —H/—H | 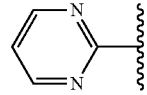 [SMILES: *c1ncccn1] | —H/—H |
| Ex-63 | —CH$_3$/—H/—H | —H/—H | 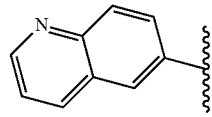 [SMILES: *c1ccc2ncccc2c1] | —H/—H |
| Ex-64 | —CH$_3$/—H/—H | —H/—H | 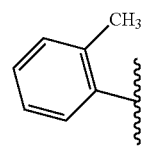 | —H/—H |
| Ex-65 | CH$_3$/—H/—H | —H/—H | 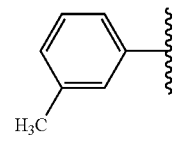 [SMILES: *c1cccc(C)c1] | —H/—H |
| Ex-66 | —CH$_3$/—H/—H | —H/—H | 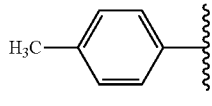 | —H/—H |
| Ex-67 | —CH$_3$/—H/—H | —H/—H | 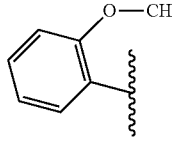 | —H/—H |
| Ex-68 | CH$_3$/—H/—H | —H/—H | 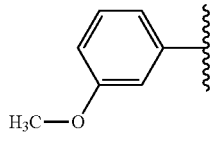 | —H/—H |
| Ex-69 | —CH$_3$/—H/—H | —H/—H | 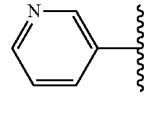 | —H/—H |
| Ex-70 | —CH$_3$/—H/—H | —H/—H | 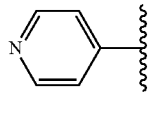 | —H/—H |
| Ex-71 | —CH$_3$/—H/—H | —H/—H | 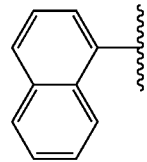 [SMILES: *c1cccc2ccccc12] | —H/—H |
| Ex-72 | —CH$_3$/—H/—H | —H/—H | 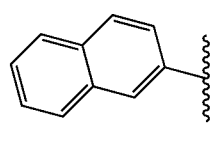 [SMILES: *c1ccc2ccccc2c1] | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-73 | —CH₃/—H/—H | —H/—H | 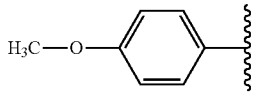 4-methoxyphenyl | —H/—H |
| Ex-74 | —CH₃/—H/—H | —H/—H | 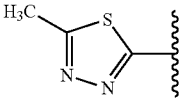 5-methyl-1,3,4-thiadiazol-2-yl | —H/—H |
| Ex-75 | —CH₃/—H/—H | —H/—H | 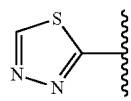 1,3,4-thiadiazol-2-yl | —H/—H |
| Ex-76 | —CH₃/—H/—H | —H/—H | 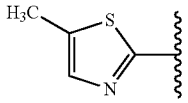 5-methylthiazol-2-yl | —H/—H |
| Ex-77 | —CH₃/—H/—H | —H/—H | 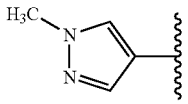 1-methyl-1H-pyrazol-4-yl | —H/—H |
| Ex-78 | —CH₃/—H/—H | —H/—H | 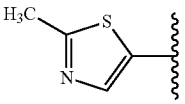 2-methylthiazol-5-yl | —H/—H |
| Ex-79 | —CH₃/—H/—H | —H/—H | 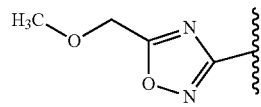 [SMILES: *c1noc(COC)n1] 5-(methoxymethyl)-1,2,4-oxadiazol-3-yl | —H/—H |
| Ex-80 | —CH₃/—H/—H | —H/—H | 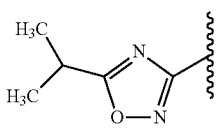 [SMILES: *c1noc(C(C)C)n1] 5-isopropyl-1,2,4-oxadiazol-3-yl | —H/—H |
| Ex-81 | —CH₃/—H/—H | —H/—H | 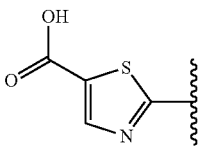 [SMILES: *c1ncc(C(=O)O)s1] 2-(carboxy)thiazol-5-yl | —H/—H |
| Ex-82 | —CH₃/—H/—H | —H/—H | 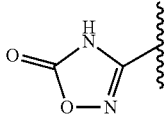 [SMILES: *c1noc(=O)[nH]1] 5-oxo-4,5-dihydro-1,2,4-oxadiazol-3-yl | —H/—H |
| Ex-83 | —CH₃/—H/—H | —H/—H | 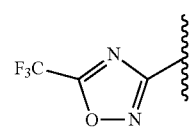 [SMILES: *c1noc(C(F)(F)F)n1] 5-(trifluoromethyl)-1,2,4-oxadiazol-3-yl | —H/—H |
| Ex-84 | —CH₃/—H/—H | —H/—H | 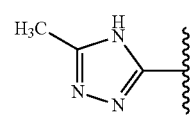 5-methyl-4H-1,2,4-triazol-3-yl | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-85 | —CH₃/—H/—H | —H/—H | 1-ethyl-1H-pyrazol-4-yl | —H/—H |
| Ex-86 | —CH₃/—H/—H | —H/—H | 4-chloro-1,2,5-thiadiazol-3-yl | —H/—H |
| Ex-87 | —CH₃/—H/—H | —H/—H | 5-ethyl-1,2,4-oxadiazol-3-yl | —H/—H |
| Ex-88 | —CH₃/—H/—H | —H/—H | 5-tert-butyl-1,2,4-oxadiazol-3-yl | —H/—H |
| Ex-89 | —CH₃/—H/—H | —H/—H | 1,3,4-thiadiazol-2-yl | —H/—H |
| Ex-90 | —CH₃/—H/—H | —H/—H | (3-cyclopropyl-1,2,4-oxadiazol-5-yl)carbonyl | —H/—H |
| Ex-91 | —CH₃/—H/—H | —H/—H | 3-tert-butyl-1,2,4-oxadiazol-5-yl | —H/—H |
| Ex-92 | —CH₃/—H/—H | —H/—H | (S)-1-(2,4-difluorophenyl)ethyl | —H/—H |
| Ex-93 | —CH₃/—H/—H | —H/—H | (R)-1-(2,4-difluorophenyl)ethyl | —H/—H |
| Ex-94 | —CH₃/—H/—H | —H/—H | 4-(2-methoxyethoxy)phenyl | —H/—H |
| Ex-95 | —CH₃/—H/—H | —H/—H | 2,4-difluorophenylmethyl | —H/—H |

TABLE I-continued
| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-96 | —CH₃/—H/—H | —H/—H | 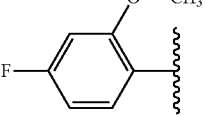 | —H/—H |
| Ex-97 | —CH₃/—H/—H | —H/—H | 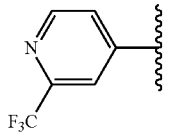 [SMILES: *c1ccnc(C(F)(F)F)c1] | —H/—H |
| Ex-98 | —CH₃/—H/—H | —H/—H | 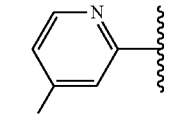 | —H/—H |
| Ex-99 | —CH₃/—H/—H | —H/—H | 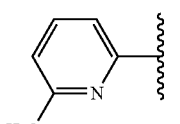 | —H/—H |
| Ex-100 | —CH₃/—H/—H | —H/—H | 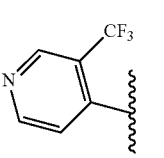 [SMILES: *c1ccncc1C(F)(F)F] | —H/—H |
| Ex-101 | —CH₃/—H/—H | —H/—H | 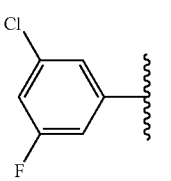 [SMILES: *c1cc(F)cc(Cl)c1] | —H/—H |
| Ex-102 | —CH₃/—H/—H | —H/—H | 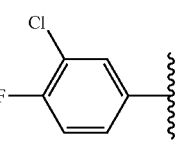 | —H/—H |
| Ex-103 | —CH₃/—H/—H | —H/—H | 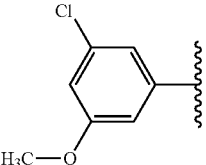 | —H/—H |
| Ex-104 | —CH₃/—H/—H | —H/—H | 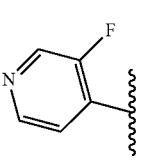 [SMILES: *c1ccncc1F] | —H/—H |
| Ex-105 | —CH₃/—H/—H | —H/—H | 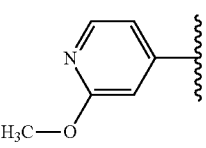 | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
| --- | --- | --- | --- | --- |
| Ex-106 | —CH₃/—H/—H | —H/—H | 3,5-difluorophenyl | —H/—H |
| Ex-107 | —CH₃/—H/—H | —H/—H | 4-fluoropyridin-2-yl | —H/—H |
| Ex-108 | —CH₃/—H/—H | —H/—H | 1-tert-butyl-1H-pyrazol-4-yl | —H/—H |
| Ex-109 | —CH₃/—H/—H | —H/—H | 4-(2-hydroxyethoxy)-1,2,5-thiadiazol-3-yl | —H/—H |
| Ex-110 | —CH₃/—H/—H | —H/—H | 2-cyclopropylbenzo[d]oxazol-6-yl | —H/—H |
| Ex-111 | —CH₃/—H/—H | —H/—H | 2,4-dimethylthiazol-5-yl | —H/—H |
| Ex-112 | —CH₃/—H/—H | —H/—H | 1-methyl-1H-indazol-4-yl | —H/—H |
| Ex-113 | —CH₃/—H/—H | —H/—H | pyrazin-2-yl | —H/—H |
| Ex-114 | —CH₃/—H/—H | —H/—H | 4-cyanopyridin-2-yl | —H/—H |
| Ex-115 | —CH₃/—H/—H | —H/—H | 4-fluoro-3-methoxyphenyl | —H/—H |

TABLE I-continued

| Example No. | R^{a1}/R^{a2}/R^{a5} | R^{a3}/R^{a4} | R^{b2} | R^{G4}/R^{G5} |
|---|---|---|---|---|
| Ex-116 | —CH₃/—H/—H | —H/—H | 3,4-dimethoxypyridin-5-yl | —H/—H |
| Ex-117 | —CH₃/—H/—H | —H/—H | 3,4-bis(trifluoromethyl)phenyl | —H/—H |
| Ex-118 | —CH₃/—H/—H | —H/—H | 4-methoxy-3-(trifluoromethyl)phenyl | —H/—H |
| Ex-119 | —CH₃/—H/—H | —H/—H | 4-morpholinophenyl | —H/—H |
| Ex-120 | —CH₃/—H/—H | —H/—H | 3,5-bis(trifluoromethyl)phenyl | —H/—H |
| Ex-121 | —CH₃/—H/—H | —H/—H | 2-chloro-5-methoxyphenyl | —H/—H |
| Ex-122 | —CH₃/—H/—H | —H/—H | 3,5-difluoropyridin-2-yl | —H/—H |
| Ex-123 | —CH₃/—H/—H | —H/—H | 4-(difluoromethyl)pyridin-2-yl | —H/—H |
| Ex-124 | —CH₃/—H/—H | —H/—H | 3,5-dichlorophenyl | —H/—H |
| Ex-125 | —CH₃/—H/—H | —H/—H | 4-chloro-3-methoxyphenyl | —H/—H |

TABLE I-continued
| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-126 | —CH₃/—H/—H | —H/—H | 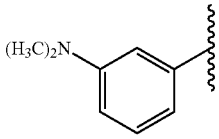 | —H/—H |
| Ex-127 | —CH₃/—H/—H | —H/—H | 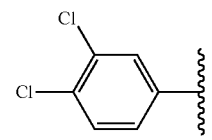 [SMILES: *c1ccc(Cl)c(Cl)c1] | —H/—H |
| Ex-128 | —CH₃/—H/—H | —H/—H | 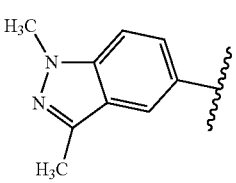 | —H/—H |
| Ex-129 | —CH₃/—H/—H | —H/—H | 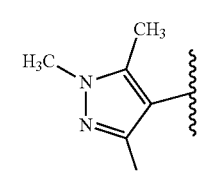 | —H/—H |
| Ex-130 | —CH₃/—H/—H | —H/—H | 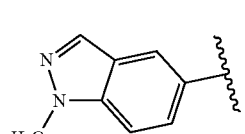 | —H/—H |
| Ex-131 | —CH₃/—H/—H | —H/—H | 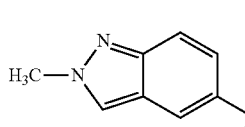 | —H/—H |
| Ex-132 | —CH₃/—H/—H | —H/—H | 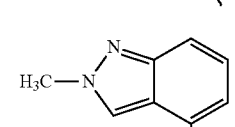 | —H/—H |
| Ex-133 | —CH₃/—H/—H | —H/—H | 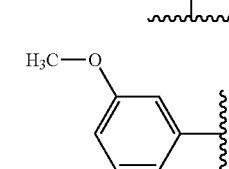 | —H/—H |
| Ex-134 | —CH₃/—H/—H | —H/—H | 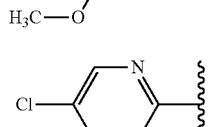 | —H/—H |
| Ex-135 | —CH₃/—H/—H | —H/—H | 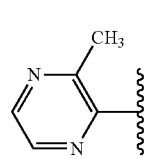 [SMILES: *c1nccnc1C] | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-136 | —CH₃/—H/—H | —H/—H | 3-fluoro-6-methylpyridin-2-yl | —H/—H |
| Ex-137 | —CH₃/—H/—H | —H/—H | 5-cyanopyridin-2-yl | —H/—H |
| Ex-138 | —CH₃/—H/—H | —H/—H | 5-methylpyridin-2-yl | —H/—H |
| Ex-139 | —CH₃/—H/—H | —H/—H | 4,5-bis(trifluoromethyl)pyridin-2-yl | —H/—H |
| Ex-140 | —CH₃/—H/—H | —H/—H | 1-(tert-butyl)-1H-pyrazol-4-yl | —H/—H |
| Ex-141 | —CH₃/—H/—H | —H/—H | 3-(methoxymethyl)-2-methyl-2H-indazol-5-yl | —H/—H |
| Ex-142 | —CH₃/—H/—H | —H/—H | 4-methoxypyridin-2-yl | —H/—H |
| Ex-143 | —CH₃/—H/—H | —H/—H | 3-(methylsulfonyl)phenyl | —H/—H |
| Ex-144 | —CH₃/—H/—H | —H/—H | 4-methylpyridin-3-yl | —H/—H |
| Ex-145 | —CH₃/—H₃/—H | —H/—H | 5-fluoropyridin-3-yl | —H/—H |
| Ex-146 | —CH₃/—H/—H | —H/—H | 5-methoxypyridin-3-yl | —H/—H |

TABLE I-continued
| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-147 | —CH₃/—H/—H | —H/—H | F₃C—H₂C-- | $R^{G4}$ and $R^{G5}$ together form —(C=O)— |
| Ex-148 | —CH₃/—H/—H | —H/—H | 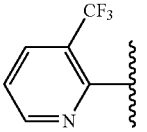 [SMILES: *c1ncccc1C(F)(F)F] | —H/—H |
| Ex-149 | —CH₃/—H/—H | —H/—H | 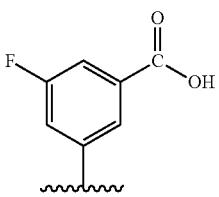 | —H/—H |
| Ex-150 | —CH₃/—H/—CH₃ | —H/—H | 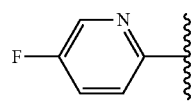 | —H/—H |
| Ex-151 | —CH₃/—H/—H | —H/—H | 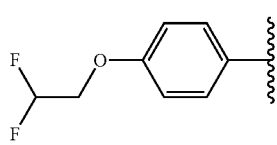 [SMILES: *c1ccc(OCC(F)F)cc1] | —H/—H |
| Ex-152 | —CH₃/—H/—H | —H/—H | 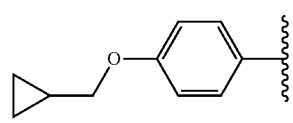 | —H/—H |
| Ex-180 | —H/—H/—H | —CH₃/—CH₃ | 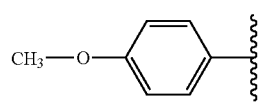 | —H/—H |
| Ex-181 | —H/—H/—H | —H/—CH₃ | 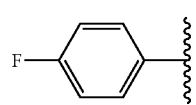 | —H/—H |
| Ex-182 | —H/—H/—H | —H/—CH₃ | 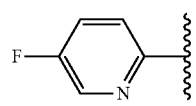 | —H/—H |
| Ex-183 | —CH₃/—CH₃/—H | —H/—H | 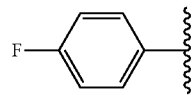 | —H/—H |
| Ex-187 | —H/—H/—H | —CH₃/—CH₃ | 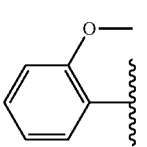 [SMILES: *c1ccccc1OC] | —H/—H |
| Ex-198 | —H/—H/—H | —CH₃/—H | 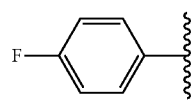 [SMILES: *c1ccc(F)cc1] | —H/—H |

TABLE I-continued

| Example No. | $R^{a1}/R^{a2}/R^{a5}$ | $R^{a3}/R^{a4}$ | $R^{b2}$ | $R^{G4}/R^{G5}$ |
|---|---|---|---|---|
| Ex-199 | —CH$_3$/—CH$_3$/—H | —H/—H | 5-(trifluoromethyl)pyridin-2-yl | —H/—H |
| Ex-200 | —CH$_3$/—CH$_3$/—H | —H/—H | (4-(trifluoromethyl)phenyl)carbonyl | —H/—H |
| Ex-201 | —CH$_3$/—H/—CH$_3$ | —H/—H | (4-fluorophenyl)carbonyl | —H/—H |
| Ex-202 | —CH$_3$/—CH$_3$/—H | —H/—H | (4-fluorophenyl)carbonyl | —H/—H |

In some embodiments, a compound of the invention is a compound of Formula B, or a pharmaceutically acceptable salt thereof:

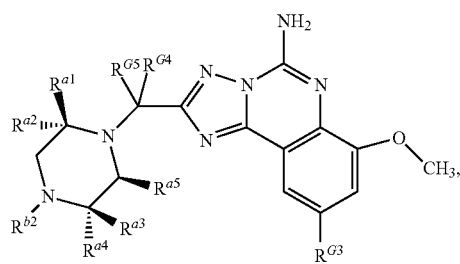

Formula B wherein $R^{G3}$ is —F, $R^{a5}$ is —H, and the $R^{G4}$, $R^{G5}$, $R^{a1}$ to $R^{a4}$, and $R^{b2}$ are defined in Table II, below:

TABLE II

| Example No. | $R^{a1}/R^{a2}$ | $R^{a3}/R^{a4}$ | $R^{b2}$ | $R^{G4}/R^{G5}$ |
|---|---|---|---|---|
| Ex-11 | —CH$_3$/—H | —H/—H | 4-fluorophenyl | —H/—H |
| Ex-37 | —H/—CH$_3$ | —H/—H | 4-fluorophenyl | —H/—H |
| Ex-41 | —CH$_3$/—H | —H/—H | 5-fluoropyridin-2-yl | —H/—H |
| Ex-42 | —CH$_3$/—H | —H/—H | 5-(trifluoromethyl)pyridin-2-yl | —H/—H |
| Ex-178 | —H/—H | —H/—CH$_3$ | 4-fluorophenyl | —H/—H |
| Ex-184 | —H/—H | —CH$_3$/—CH$_3$ | 4-methoxyphenyl | —H/—H |
| Ex-185 | —H/—H | —CH$_3$/—CH$_3$ | 4-bromophenyl | —H/—H |
| Ex-186 | —H/—H | —CH$_3$/—CH$_3$ | 3-methoxyphenyl | —H/—H |

In some embodiments, a compound of the invention is a compound of Formula E, or a pharmaceutically acceptable salt thereof:

Formula E

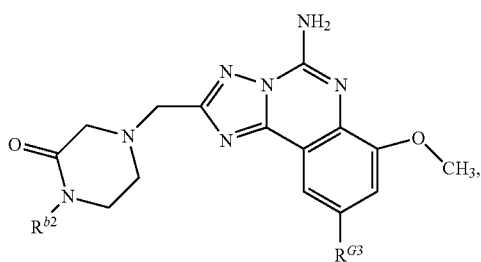

wherein R$^{b2}$ and R$^{G3}$ are defined in Table III, below:

TABLE III

| Example No. | R$^{b2}$ | R$^{G3}$ |
|---|---|---|
| Ex-210 | (4-methylbenzyl) | —H |
| Ex-209 | (4-methoxybenzyl) | —H |
| Ex-211 | (4-fluorobenzyl) | —F |

In some embodiments, the compounds of Formula A have the structure of Formula F, or a pharmaceutically acceptable salt thereof:

Formula F

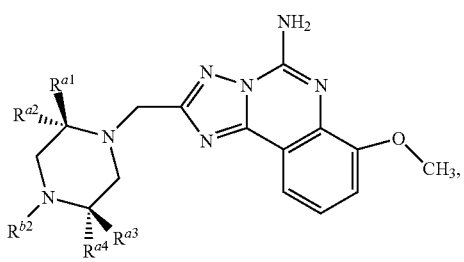

wherein each substituent of one pair of R$^{a1}$/R$^{a2}$ or R$^{a3}$/R$^{a4}$ is —H, and the other pair together form a spirocyclpropyl moiety, in accordance with the definition of R$^{a1}$ to R$^{a4}$ and R$^{b2}$ presented in Table IV below:

TABLE IV

| Example No. | R$^{a1}$/R$^{a2}$ | R$^{a3}$/R$^{a4}$ | R$^{b2}$ |
|---|---|---|---|
| Ex-188 | spirocyclopropyl | —H/—H | ethoxycarbonyl |

TABLE IV-continued

| Example No. | R$^{a1}$/R$^{a2}$ | R$^{a3}$/R$^{a4}$ | R$^{b2}$ |
|---|---|---|---|
| Ex-189 | spirocyclopropyl | —H/—H | 4-(2-methoxyethoxy)phenyl |
| Ex-190 | spirocyclopropyl | —H/—H | 3-(2-methoxyethoxy)phenyl |
| Ex-191 | spirocyclopropyl | —H/—H | 4-fluorophenyl |
| Ex-192 | spirocyclopropyl | —H/—H | FCH$_2$—CH$_2$— |
| Ex-193 | spirocyclopropyl | —H/—H | H$_3$C—O—(CH$_2$)$_2$— |
| Ex-194 | spirocyclopropyl | —H/—H | cyclopropyl-SO$_2$— |
| Ex-195 | —H/—H | spirocyclopropyl | 4-fluorophenyl |
| Ex-196 | spirocyclopropyl | —H/—H | F$_3$C—(CH$_2$)$_2$— |

In some embodiments, compounds of the invention have the structure of Formula G, or a pharmaceutically acceptable salt thereof:

Formula G

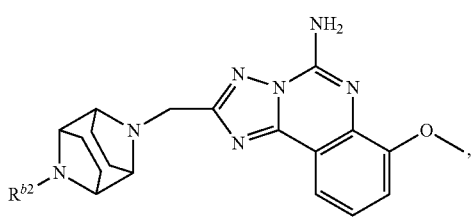

wherein R$^{b2}$ is —H (Ex-208); a 1-(4-fluorophenyl)-methanone substituent (Ex-204); a 1-(4-trifluoromethylphenyl)-methanone substituent (Ex-203), or a 2-[5-(trifluoromethyl)pyridinyl]-substituent (Ex-205).

In some embodiments, compounds of the invention preferably have the structure of Formula CC4a:

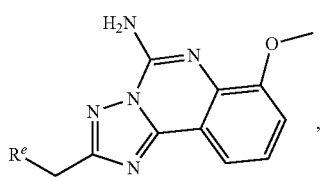
or a salt thereof,
wherein $R^e$ is:
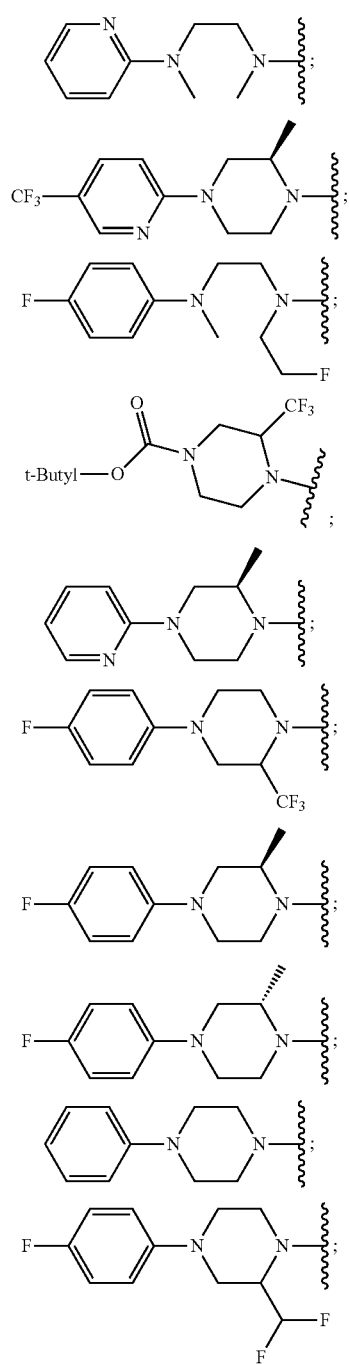
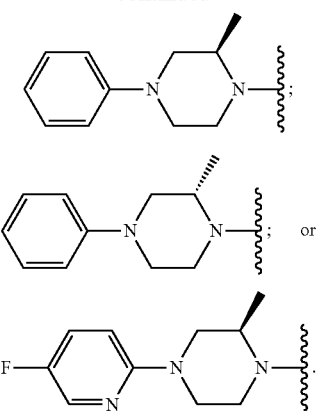
In some embodiments, compounds of the invention preferably have the structure of Formula CC5a:
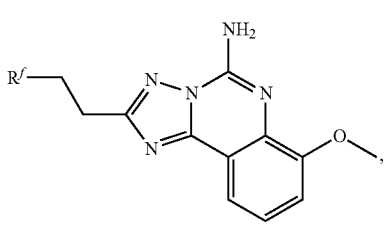
or a salt thereof,
where "$R^f$" is:
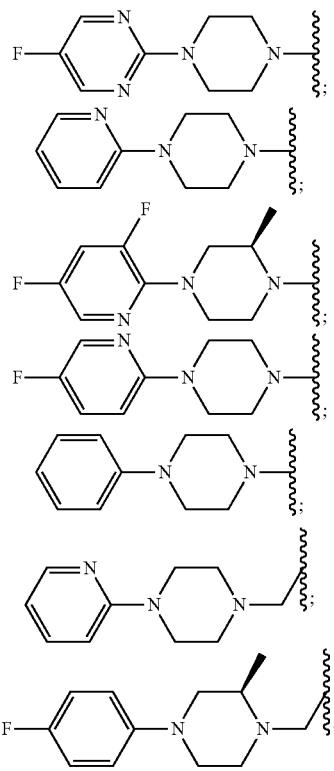

-continued

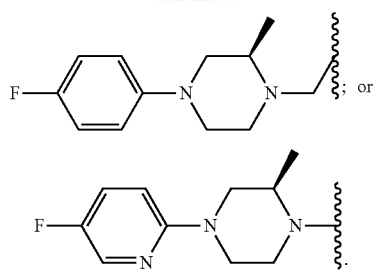

In some embodiments, compounds of the invention have the structure of Formula H, or a pharmaceutically acceptable salt thereof:

Formula H

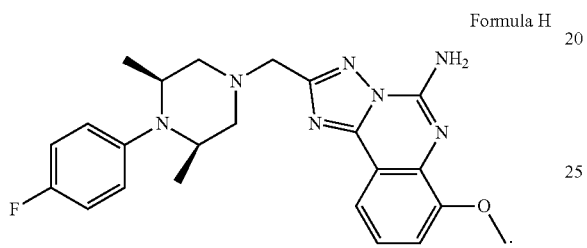

In some embodiments, compounds of the invention have the structure of the Formula Ja or Formula Jb, or a pharmaceutically acceptable salt thereof:

Formula Ja

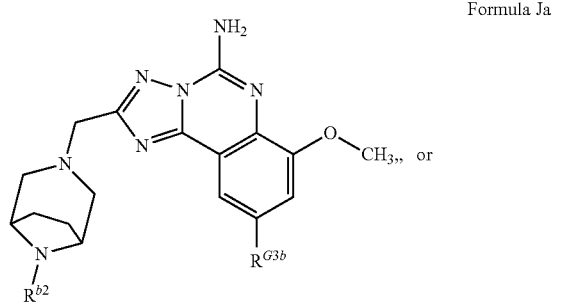

Formula Jb

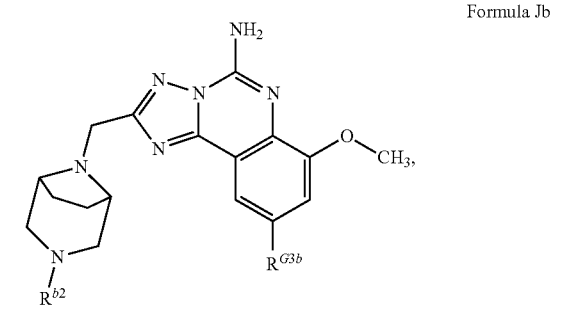

wherein $R^{G3b}$ is —H or —F; and $R^{b2}$ is a mono- or polycyclic aryl moiety comprising from 5 to 10 carbon atoms, which is optionally linked to the nitrogen of the piperazine moiety through a carbonyl carbon, thereby forming an amide linkage, and wherein one or more ring carbon atoms thereof is optionally substituted with a moiety that is, independently for each occurrence:

(i) halogen, preferably F or Cl;
(ii) $C_{1-6}$-alkyl, which is optionally halogen substituted, and in such optional embodiments the halogen-substituted alkyl is preferably —$CF_3$;
(iii) $C_{1-6}$-alkoxy, preferably methoxy;
(iv) $C_{1-6}$-alkoxy-$C_{1-6}$-alkoxide;
(v) aryloxy of from 6 to 10 carbon atoms;
(vi) $C_{1-6}$-heterocycloalkyl comprising from 1 to 3 heteroatoms that are, independently for each occurrence, N, S or O, wherein in some embodiments the heterocycloalkyl it is preferably a -pyrrolidinyl moiety, and wherein said heterocycloalkyl may optionally include a carbonyl group (C=O), and wherein in some embodiments where said heterocycloalkyl comprises a carbonyl group, it is preferably a -pyrolidin-oneyl moiety;
(vii) $(R^{d1})_2N$—, wherein $R^{d1}$ is independently —H or —$C_{1-6}$-alkyl;
(viii) nitrile;
(ix) mono- or polycyclic heteroaryl of from 5 to 10 carbon atoms, comprising from 1 to 4 heteroatoms that are, independently for each occurrence, N, O or S; or,
(x) —C(O)—OH.

In some embodiments, preferably compounds of the invention have the structural formula shown the Examples herein.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I desends into the page, and the hydrogen on the same carbon as the ethyl group of Illus-II emerges from the page. The convention is the same where both a hashed and a solid rectangle are appended to the same carbon, as in Illus-III. he In Illus-III, the methyl group is emerging from the plane of the paper, the ethyl group is descending into the plane of the paper, and the cyclohexene ring is in the plane of the paper.

Illus-I

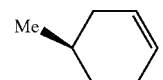

Illus-II

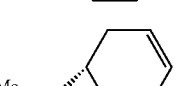

Illus-III

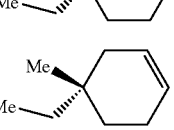

As is conventional, ordinary "stick" bonds or "wavy" bonds are used where there is a mixture of possible isomers present, including a racemic mixture of possible isomers.

As used herein, unless otherwise specified, the following terms have the following meanings.

The phrase "at least one" used in reference to the number of components comprising a composition, for example, "at least one pharmaceutical excipient," means that one member of the specified group is present in the composition, and more than one may additionally be present. Components of a composition are typically aliquots of isolated pure material added to the composition, where the purity level of the isolated material added into the composition is the normally accepted purity level of a substance appropriate for pharmaceutical use.

The phrase "at least one" used in reference to substituents on a compound or moiety appended to the core structure of a compound means that one substituent of the group of substituents specified is present, and more than one substituent may be bonded to chemically accessible bonding points of the core.

The phrase "one or more" means the same as "at least one," whether used in reference to a substituent on a compound or a component of a pharmaceutical composition.

The terms "concurrently" and "contemporaneously" both include in their meaning (1) simultaneously in time (e.g., at the same time); and (2) at different times but within the course of a common treatment schedule.

The term "consecutively" means one following the other.

The term "sequentially" refers to a series administration of therapeutic agents that awaits a period of efficacy to transpire between administering each additional agent. Thus, after an effective time period subsequent to the administration of one component, the next component is then administered. The effective time period may be the amount of time given for realization of a benefit from the administration of the first component.

The phrases "effective amount" or "therapeutically effective amount" is meant to describe the provision of an amount of at least one compound of the invention or of a composition comprising at least one compound of the invention that is effective in treating or inhibiting a disease or condition described herein, and thus produces the desired therapeutic, ameliorative, inhibitory or preventative effect. For example, in treating a movement disorder with one or more of the compounds described herein, "effective amount" (or "therapeutically effective amount") means, for example, providing the amount of at least one compound of Formula A that results in a therapeutic response in a patient afflicted with a movement disorder ("the condition"), including a response suitable to manage, alleviate, ameliorate or treat the condition; to alleviate, ameliorate, reduce or eradicate one or more symptoms attributed to the condition; and/or long-term stabilization of the condition, for example, as may be determined by the analysis of pharmacodynamic markers or clinical evaluation of patients afflicted with the condition.

The terms "patient" and "subject" mean an animal, such as a mammal (e.g., a human being), and is preferably a human being.

The term "prodrug" means compounds that are rapidly transformed, for example, by hydrolysis in blood, in vivo, to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. The scope of this invention includes prodrugs of the compounds of this invention.

The term "solvate" means a physical association of a compound with one or more solvent molecules. This physical association involves varying degrees of ionic and covalent bonding, including hydrogen bonding. In certain instances, a solvate will be capable of isolation, for example, when one or more solvent molecules are incorporated in the crystal lattice of the crystalline solid. The term "solvate" encompasses both solution-phase and isolatable solvates. Non-limiting examples of suitable solvates include ethanolates, methanolates, and the like. A "hydrate" is a solvate wherein the solvent molecule is $H_2O$.

The term "substituted" means that one or more of the enumerated substituents (or, where a list of substituents are not specifically enumerated, the default substituents specified in this "Definitions" section for the particular type of substrate that contains variable substituents) can occupy one or more of the bonding positions on the substrate typically occupied by "—H", provided that such substitution does not exceed the normal valency rules for the atom in the bonding configuration present in the substrate, and that the substitution ultimately provides a stable compound, e.g., mutually reactive substituents are not present geminal or vicinal to each other, and wherein such a compound is sufficiently robust to survive isolation to a useful degree of purity from a reaction mixture. When the text indicates optional substitution of a moiety (e.g. "optionally substituted"), the term means "if present, one or more of the enumerated (or default substituents for the specified substrate) can be present on the substrate in a bonding position normally occupied by a hydrogen atom," in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention, have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like). Moieties are equivalently described herein by structure, typographical representation or chemical terminology without intending any differentiation in meaning. For example, the chemical term "acyl", defined below, is equivalently described herein by the term itself, or by typographical representations "R'—(C═O)—" or "R'—C(O)—", or by the structural representation:

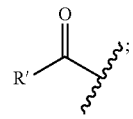

"acyl" means an R'—C(O)—, where R' is a linear, branched or cyclic alkyl; a linear, branched or cyclic alkenyl; or a linear, branched or cyclic alkynyl moiety, each of which moieties can be substituted; wherein the acyl substituent is bonded through the carbonyl carbon to the substrate of which it is a substituent, or —NH—$SO_2$—R', where —R' is as previously defined; non-limiting examples of suitable acyl groups include formyl, acetyl, propanoyl, 2-methylpropanoyl, butanoyl and cyclohexanoyl;

"alkenyl" means an aliphatic hydrocarbon moiety that is not aromatic but includes in its structure at least one constituent of the structure —(R'C═CR'$_2$) or —(R'C═CR')—, where R' is a defined substituent, for example —H or -alkyl; the alkenyl moiety can be incorporated into a linear hydrocarbon chain, or incorporated into a cyclic hydrocarbon chain (termed "cycloalkenyl") and can comprise further, linear, branched or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms;

the term "substituted alkenyl," unless specified otherwise by a recitation of specific substituents defining the term, means that the alkenyl group is substituted by one or more substituents that are independently for each occurrence: $C_{1-10}$ alkyl, $C_{3-10}$ cycloalkyl, and $C_{1-10}$ alkoxy;

"-alkoxy" means a moiety of the structure: alkyl-O— (i.e., the bond to the substrate moiety is through the ether oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxyalkyl" means a moiety of the structure: alkoxy-alkyl- (i.e., the bond to the substrate moiety is through an alkyl moiety, which is terminated by, or substituted with, an alkoxy substituent that is not itself bonded to the substrate); non-limiting examples of alkoxyalkyl groups include $H_3C$—$(CH_2)_y$—O—$CH_2$—$(CH_2)_x$—, wherein "y" and "x" are independently an integer of from 0 to 6;

"alkoxycarbonyl" means a moiety of the structure alkyl-O—C(O)—, equivalently represented as [alkyl-O—(C=O)—] and also as R—O(C=O)—, where "R" is a defined alkyl moiety (i.e., the bond to the parent moiety is through the carbonyl carbon), wherein the alkyoxy portion of the moiety is as previously defined; non-limiting examples of suitable alkoxycarbonyl groups include methoxycarbonyl and ethoxycarbonyl;

"-alkyl" (including the alkyl portions of other moieties, such as trifluoromethyl-alkyl- and -alkoxy) means an aliphatic hydrocarbon chain comprising from about 1 to about 20 carbon atoms (that is, "$C_{1-20}$ alkyl"), preferably 1 to about 10 carbon atoms (herein "$C_{1-10}$ alkyl"), unless the term is modified by an indication that a shorter chain is contemplated, for example, an alkyl moiety of up to 8 carbon atoms (designated herein "$C_{1-8}$-alkyl"); the term "alkyl," unless specifically limited by another term, for example, "linear," "branched" or "cyclic," includes alkyl moieties that are linear (a hydrocarbon chain with no aliphatic hydrocarbon "branches" appended to it); branched (a main hydrocarbon chain comprising up to the maximum specified number of carbon atoms with a lower-alkyl chain appended to one or more carbon atoms comprising, but not terminating, the main hydrocarbon chain); and cyclic (the main hydrocarbon chain forms an cyclic aliphatic moiety of from 3 carbon atoms, the minimum number necessary to provide a cyclic moiety, up to the maximum number of specified carbon atoms), accordingly when unmodified, the term "$C_{1-X}$ alkyl" refers to linear, branched or cyclic alkyl, and the "$C_{1-X}$" designation means: for a cyclic moiety a ring comprising at minimum 3 carbon atoms up to "X" carbon atoms; for a branched moiety, a main chain of at least 3 carbon atoms up to "X" carbon atoms with at least one linear or branched alkyl moiety bonded to a carbon atom that does not terminate the chain; and for a linear alkyl, a moiety comprising one carbon atom (i.e., -methyl), up to "X" carbon atoms; when the term "alkyl" is modified by "substituted" or "optionally substituted" it means an alkyl group having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence (in accordance with definitions appearing herein): $C_{1-20}$ alkyl; halogen; -alkoxy; —OH; —CN; alkylthio-; amino, —NH(alkyl), —NH(cycloalkyl), —N(alkyl)$_2$, —(C=O)—OH; —C(O)O-alkyl; —S(alkyl); or —S(O$_2$)-alkyl; or -aryl; cycloalkyl moieties may alternatively, or in addition, be substituted with one or more "ring-system substituents" as that term is defined herein; examples of suitable alkyl groups include, but are not limited to, methyl, ethyl, n-propyl, isopropyl, n-butyl, t-butyl, n-pentyl, heptyl, nonyl, decyl, fluoromethyl, trifluoromethyl and cyclopropylmethyl; where the term "alkyl" is indicated with two hyphens (i.e., "-alkyl-") it indicates that the alkyl moiety is bonded in a manner that the alkyl moiety connects a substrate with another moiety, for example, "-alkyl-OH" indicates an alkyl moiety connecting a hydroxyl moiety to a substrate;

"lower alkyl" means a group comprising about 1 to about 6 carbon atoms in the chain (i.e., $C_{1-6}$); non-limiting examples of suitable lower alkyl groups include methyl, ethyl, n-propyl, isopropyl, n-butyl, t-butyl, n-pentyl, and hexyl;

"alkylaryl" (or alkaryl) means an alkyl-aryl-group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

in general, as exemplified by the term "alkyl-aryl" defined above, a substituent that is the called out by the combination of terms used to define two other substituent fragments indicates that the substituent called out by the last term used is bonded to the substrate whilst the preceding term called out is bonded in turn to the substituent fragment it precedes, proceeding right to left to understand the order in which the various fragments are bonded to the substrate;

"alkynyl" means an aliphatic hydrocarbon group (chain) comprising at least one moiety of the structure:

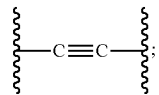 [SMILES: *C#C*]

or the structure:

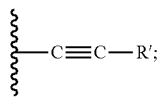

wherein R' is a defined substituent; the alkynyl moiety can be incorporated into a linear or branched hydrocarbon chain, or incorporated into a cyclic hydrocarbon chain (non-aromatic, termed "cycloalkynyl"); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —NR$_2$ group wherein R is selected independently for each occurrence from —H or alkyl; alkylamino means —NR'$_2$, wherein one R' is -alkyl and the other is —H or -alkyl selected independently for each occurrence; non-limiting examples of alkylamino moieties are —NH—CH$_3$ (methylamino-) and —N(CH$_3$)$_2$ (dimethylamino);

"ammonium ion" means —N$^+$R$_3$, wherein R is independently —H, alkyl, substituted alkyl, or the cationic portion of a dissociated acid capable of producing an ammonium ion from an amine; when not explicitly shown in representations herein the presence of an ammonium ion presumes that a charge-balancing anion is associated with the ammonium ion moiety, which anion is derived from the anionic portion of the acid used to provide said ammonium ion; it will be appreciated that many of the nitrogen atoms present in compounds of the invention can be converted to an ammonium ion thereby providing a salt of the parent compound, which is within the scope of the invention;

"aryl" (sometimes abbreviated "ar") means an aromatic monocyclic or multicyclic ring system comprising about 6 to about 14 carbon atoms (denoted herein also as "C$_{6-14}$-aryl"), preferably about 6 to about 10 carbon atoms ("C$_{6-10}$-aryl"); the aryl group can be optionally substituted with one or more independently selected "ring system substituents" (defined below); non-limiting examples of suitable aryl groups include phenyl

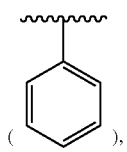

which is also abbreviated herein "Ph" for convenience, and naphthyl

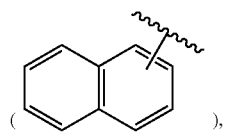

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"aryloxy" means an aryl-O— group (i.e., the moiety is bonded to a substrate through the ether oxygen), wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to a substrate is through the carbonyl carbon), wherein the aryl group is unsubstituted or substituted as previously defined; non-limiting examples of suitable aryloxycarbonyl groups include phenoxycarbonyl and naphthoxycarbonyl;

a "carboxylic acid" moiety means a substituent having the formula "—C(O)—OH", wherein the moiety is bonded to a substrate is through the carbonyl carbon;

"cycloalkyl," defined above with the "alkyl" definition, means a non-aromatic mono- or multicyclic ring system comprising about 3 to about 20 carbon atoms that may be substituted as defined herein; the term includes multicyclic cycloalkyls, for example, 1-decalin, norbornyl, adamantyl and the like;

"halogen" means fluorine, chlorine, bromine or iodine; preferred halogens, unless specified otherwise where the term is used, are fluorine, chlorine and bromine; a substituent which is a halogen atom means —Cl, —Br or —I, and "halo" means fluoro, chloro, bromo or iodo substituents bonded to the moiety defined, for example, "haloalkyl" means an alkyl, as defined above, wherein one or more of the bonding positions on the alkyl moiety typically occupied by hydrogen atoms is instead occupied by a halo group; perhaloalkyl means that all bonding positions not participating in bonding the alkyl substituent to a substrate are occupied by a halogen, for example, perfluoroalkyl, where alkyl is methyl, means —CF$_3$;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise 5 ring atoms, for example, thiazole thiadiazole, imidazole, isothiazole, oxazole, oxadiazole, or pyrazole; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include:

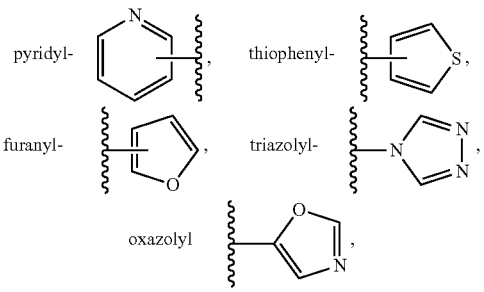

pyrazinyl, thienyl, pyrimidinyl, isoxazolyl, isothiazolyl, thiazolyl, pyrazolyl, furazanyl, pyrrolyl, pyrazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

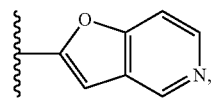

and the like (unless otherwise noted, bonded to the substrate through any available atom that results in a stable bonding arrangement);

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl—

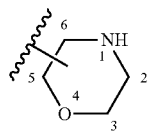

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like;

"tetrahydropyranyl" moiety means a 6-member cyclic ether of the formula:

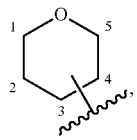

where the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 that are not occupied by the bond to the substrate can optionally be occupied by specified or optional substituents;

"piperidinyl" means:

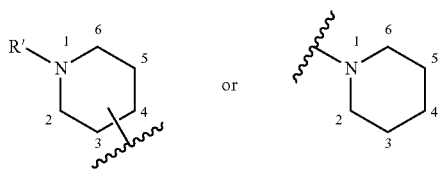

where the open bond line terminated on one end with a wavy line indicates the ring atom through which the moiety is bonded to the substrate (i.e., any of carbon atoms 2 to 6 (left-hand structure) or the ring nitrogen atom (right-hand structure)), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either —H or another specified substituent;

"pyridinyl" means:

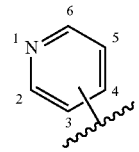

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 that is not the bond to the substrate can optionally be occupied by a specified substituent;

"quinoline" means:

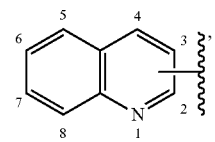

where the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 that are not bonded to the substrate can optionally be occupied by one of a list of enumerated substituents;

for any of the foregoing ring-system moieties, bonding of the moiety through a specific ring carbon atom (or heteroatom) is sometimes described for convenience and "bonded through C—X to C—Y carbon atoms," where "X" and "Y" are integers referring to the carbon atoms, for example, as numbered in the examples above;

"hydroxyl moiety" and "hydroxy" means an HO— group; "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

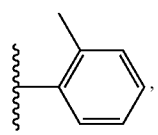

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding, for example:

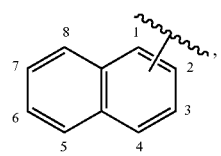

indicates that the naphthalene moiety may be bonded to the substrate through any of carbons 1 to 8.

Any carbon or heteroatom with unsatisfied valences in the text, schemes, examples, structural formulae and any Tables herein is assumed to have a hydrogen atom or atoms of sufficient number to satisfy the valences.

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents." The bulk composition is material that has not yet been formed into individual dosage units.

This invention also includes the compounds of this invention in isolated and purified form obtained by routine techniques. Polymorphic forms of the compounds and pharmaceutically acceptable salts thereof are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures.

All stereoisomers (for example, geometric isomers, optical isomers and the like) of the present compounds (including prodrugs of compounds of the invention as well as the salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt,", "solvate," "prodrug" and the like, is intended to equally apply to salts, solvates and prodrugs of isolated enantiomers, stereoisomer pairs or groups, rotamers, tautomers, or racemates of the inventive compounds.

Diasteromeric mixtures can be separated into their individual diastereomers on the basis of their physical chemical differences by methods well known to those skilled in the art, for example, by chiral chromatography and/or fractional crystallization. As is know, enantiomers can also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding enantiomers.

Where the compounds of the invention form salts by known, ordinary methods, these salts are also within the scope of this invention. Reference to a compound of the invention herein is understood to include reference to salts thereof, unless otherwise indicated. The term "salt(s)," as employed herein, denotes acidic salts formed with inorganic and/or organic acids, as well as basic salts formed with inorganic and/or organic bases. In addition, when a compound of the invention contains both a basic moiety, for example, but not limited to, a nitrogen atom, for example, an amine, pyridine or imidazole, and an acidic moiety, for example, but not limited to a carboxylic acid, zwitterions ("inner salts") may be formed and are included within the term "salt(s)" as used herein. Pharmaceutically acceptable salts (i.e., non-toxic, physiologically acceptable salts) are preferred. Salts of the compounds of the invention may be formed, for example, by reacting a compound of the invention with an amount of acid or base, for example, an equivalent amount, in a medium in which the salt precipitates or in an aqueous medium wherein the product is obtained by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Intl. Union of Pure and Applied Chemistry, pp. 330-331. These disclosures are incorporated herein by reference.

Where it is possible to provide an acid addition salt with a compound, in general, acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention, and all acid and base salts are considered equivalent to the free forms of the corresponding compounds for purposes of the invention.

Compounds of the invention may exist in exist in different tautomeric forms. All such forms are embraced and included within the scope of the invention. Examples of well-known tautomeric forms include, but are not limited to, ketone/enol tautomeric forms, imine-enamine tautomeric forms, and for example heteroaromatic forms such as the following moieties:

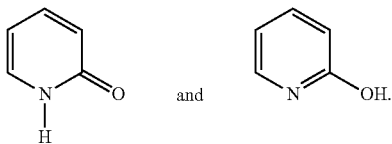 [SMILES: O=c1cccc[nH]1 ; "and" ; Oc1ccccn1]

Where a compound of the invention can exist in more than one such form, representation or presentation of one tautomeric form of such compound is considered herein equivalent to presentation of all the tautomeric forms in which the compound exists.

The term "purified," "in purified form" or "in isolated and purified form" for a compound refers to the physical state of said compound after being isolated from a synthetic process or natural source or combination thereof. Thus, the term "purified," "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When a variable (e.g., aryl, heterocycl, $R^3$, etc.) appears more than once in any moiety or in any compound of the invention, the selection of moieties defining that variable for each occurrence is independent of its definition at every other occurrence unless specified otherwise in the variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention that are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. It will be appreciated that other isotopes may be incorporated by know means also.

Certain isotopically-labeled compounds of the invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detection. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the Schemes and/or in the Examples herein below, by substituting an appropriate isotopically labeled reagent for a non-isotopically labeled reagent. Such compounds are included also in the present invention.

As mentioned above, in one aspect the invention provides pharmaceutical formulations (pharmaceutical compositions) suitable for use in blocking adenosine A2a receptors found in the basal ganglia, comprising at least one compound of Formula A presented herein, or a pharmaceutically acceptable salt thereof, and at least one pharmaceutically acceptable carrier. It will be appreciated that pharmaceutically formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of compounds of the invention, one or more other compounds which also have pharmacological activity, for example, as described herein below.

While formulations of the invention may be employed in bulk form, it will be appreciated that for most applications the inventive formulations will be incorporated into a dosage form suitable for administration to a patient or subject, each dosage form comprising an amount of the selected formulation that contains an effective amount of said one or more compounds of the invention. Examples of suitable dosage forms include, but are not limited to, dosage forms adapted for: (i) oral administration, e.g., a liquid, gel, powder, solid or semi-solid pharmaceutical composition that is loaded into a capsule or pressed into a tablet and may comprise additionally one or more coatings which modify its release properties, for example, coatings that impart delayed release or formulations that have extended release properties; (ii) a dosage form adapted for intramuscular administration (IM), for example, an injectable solution or suspension, and that may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachette or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions from the compounds described by this invention, generally pharmaceutically active compounds are combined with one or more pharmaceutically inactive excipients. These pharmaceutically inactive excipients impart to the composition properties that make it easier to handle or process, for example, lubricants or pressing aids in powdered medicaments intended to be tableted, or adapt the formulation to a desired route of administration, for example, excipients that provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier."

Pharmaceutical compositions can be solid, semi-solid or liquid. Solid form preparations can be adapted to a variety of modes of administration and include powders, dispersible granules, mini-tablets, beads, and the like for example, for tableting, encapsulation, or direct administration. Typically formulations may comprise up to about 95 percent active ingredient, although formulations with greater amounts may be prepared.

Liquid form preparations include solutions, suspensions and emulsions. Examples of liquid forms of medicament include, but are not limited to, water or water/surfactant mixtures, for example a water-propylene glycol solution, which can be employed in the preparation of formulations intended, for example, for parenteral injection, for example, as a solvent or as a suspending medium for the preparation of suspensions and emulsions where a medicament comprises constituents that are insoluble in water or water/surfactant mixtures. Liquid form preparations may also include solutions or suspensions for intranasal administration and may also include, for example, viscosity modifiers to adapt the formulation for application to particular mucosa tissues accessible via nasal administration.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations that are intended to be converted, shortly before use, to a suspension or a solution, for example, for oral or parenteral administration. Examples of such solid forms include freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch that incorporates either a matrix comprising the pharmaceutically active compound or a reservoir that comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for use of the compounds described herein for the potential treatment, management, alleviation or amelioration of conditions or disease states which can be, or are believed to be, treated, managed, alleviated or ameliorated by specific blocking of adenosine A2a receptors, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential for use in preventing or lessening the effect of drugs that cause movement disorders.

In accordance with the present invention, blocking adenosine A2a receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, or a salt thereof, and at least one pharmaceutically acceptable carrier (described below). It will be appreciated that pharmaceutical formulations of the invention may comprise more than one compound of the invention or a salt thereof, for example, the combination of two or three compounds of the invention, each present by adding to the formulation the desired amount of the compound or a salt thereof that has been isolated in a pharmaceutically acceptably pure form.

As mentioned above, administration of a compound of the invention to effect antagonism of A2a receptor sites, which is believed to be beneficial in the treatment of central nervous system diseases, is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof, for example. Methods for determining safe and effective administration of compounds that are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in whatever form administered, the dosage form administered will contain an amount of at least one compound of the invention, or a pharmaceutically acceptable salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention, e.g., a compound of Formula A, can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include compounds with dopaminergic activity, for example, i) L-DOPA; ii) DOPA decarboxylase inhibitors; and iii) COMT inhibitors.

Those skilled in the art will appreciate that treatment protocols utilizing at least one compound of Formula A can be varied according to the needs of the patient. Thus, compounds of Formula A used in the methods of this invention can be administered in variations of the protocols described above. For example, the compounds of this invention can be administered discontinuously rather than continuously during the treatment cycle.

There follows general synthetic schemes by which compounds of the invention may be prepared.

PREPARATIVE SCHEMES

Preparative Schemes: "Right-Side" Precursors

As shown in Preparative Schemes AI through ART below, compounds of the invention may be prepared by reacting a suitably functionalized triazole ("right-side" precursor), which supplies the "right-side" of the product compound desired, with a suitably functionalized "left-side" precursor, which provides either the "left-side" of the desired product compound directly, or provides an intermediate product in which the "left-side" fragment has incorporated into one or more a suitably reactive substituents that, through subsequent reactions at such reactive substituents, afford the desired product. Additionally, some of the coupling schemes illustrated below can be employed using intermediate compounds that contain certain reactive substituents (which may be present as a protected form of the reactive site), thereby yielding product compounds that contain sites that can be further reacted to provide additional compounds of the invention that are derivatives of the parent compound.

Scheme AI and AII—Preparation of Compounds of the Invention Via Joining Appropriate "Free-Amine" Precursors Providing the "Right-Side" Portion of a Compound of the Invention with a Suitably Substituted Reagent Supplying the "Left-Side" of the Desired Product With reference to Scheme AI, some compounds of the invention can be prepared by reacting suitably-substituted compound 19 (a precursor forming the "right-side" of a compound of the invention) with a suitably substituted aryl-boronic acid or heteroaryl-boronic acid precursor supplying a "left-side" fragment of the desired compound. As mentioned in the preamble, it will be appreciated that the reagent supplying the "left-side" fragment may include one or more reactive moieties that can be subsequently derivatized to supply a compound of the invention rather than reacting a complete "left-side" fragment that provides the desired compound of the invention directly from this coupling reaction. It will be appreciated that certain heteroaryl-boronic acid or arylboronic acid compounds are available as articles of commerce, including those in which the heteroaryl or aryl portion of the compound contains substituents suitable for further reaction, and which can therefore be utilized to form a precursor from which desired compounds of the invention can be prepared, as will be illustrated in the Examples below.

Scheme AI

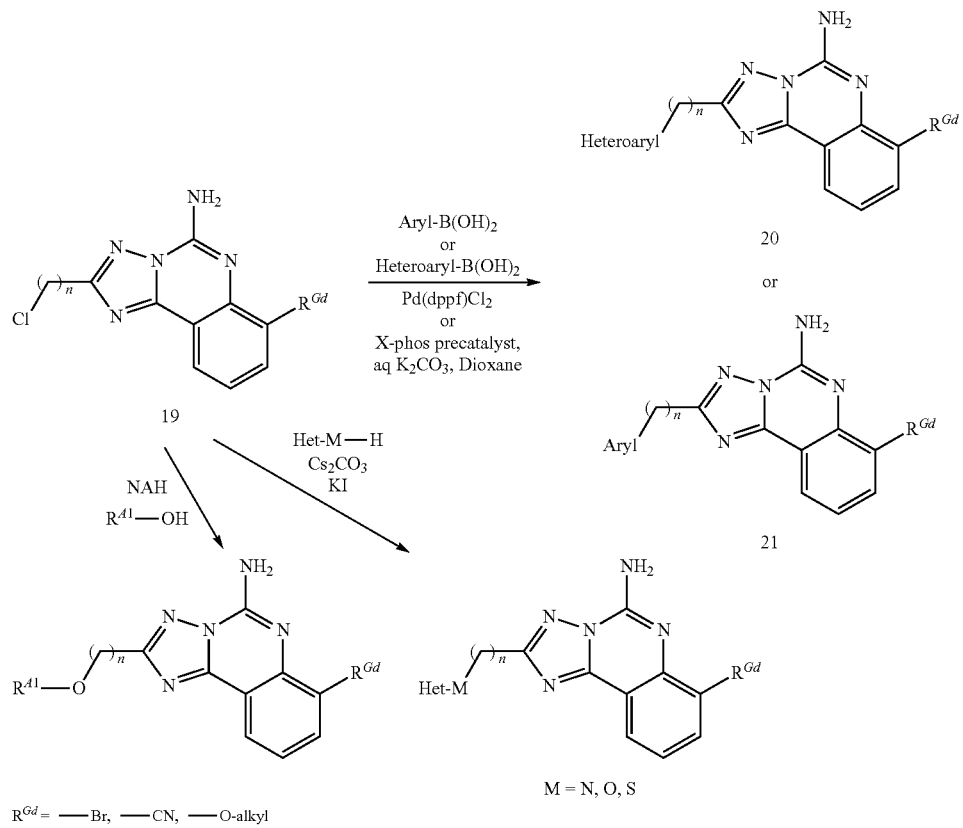

$R^{Gd}$ = —Br, —CN, —O-alkyl

As shown also in Scheme AI, a compound 19 in the presence of sodium hydride can be reacted with a reagent having a "left-side" fragment that contains a hydroxyl moiety, thereby providing a product which joins the "left-side" and "right-side" fragments with an alkoxy (—O—$CH_2$—) "linker" in place of the chloro-substituent present in compound 19. In such synthetic procedures, $R^{AI}$ can be alkyl, substituted alkyl, aryl (substituted or unsubstituted), heteroaryl (substituted or unsubstituted) bicycloalkylaryl (substituted or unsubstituted) or bicycloalkylheteroaryl (substituted or unsubstituted). In AI, the reaction shown is catalyzed by Pd(dppf)$Cl_2$ which is a palladium(2+) catalyst available as an article of commerce complexed with dichloromethane (DCM) (1,1'-Bis(diphenylphosphino)ferrocene-palladium(II)dichloride)

Amide-substituted compounds of the invention can be prepared in accordance with Scheme AII Scheme AII

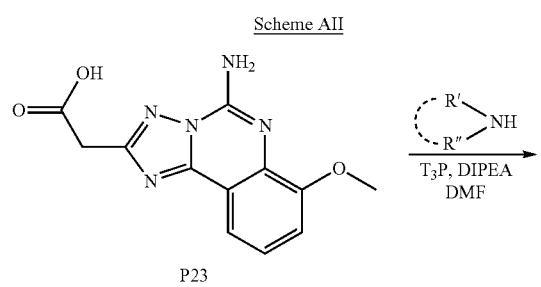

-continued

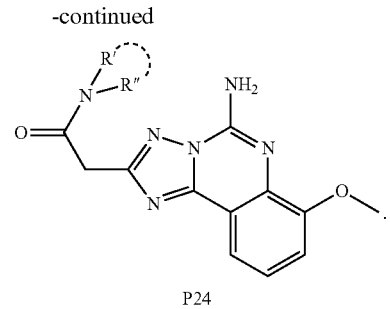

Thus, a suspension of P23 (the preparation of which is discussed further below) in DMF treated with an amine, for example, a cyclic amine, e.g. a piperidine or piperazine moiety (shown in AII as (R'—R")=NH), diisopropylethyl amine (DIPEA) and 2,4,6-tripropyl-1,3,5,2,4,6-trioxatriphosphoriane-2,4,6-trioxide (T3P) at room temperature provides the corresponding amide compound P24, which can be obtained from the reaction mixture by treating the reaction mixture with saturated NaHCO$_3$ and extracting with dichloromethane (DCM). Specific examples of these compounds are presented in the Examples below.

Scheme AIII—Preparation of Compounds of the Invention from DMoB-Protected Triazole Precursor and a "Left-Side" Precursor that is: (i) a Primary or Secondary Amine; (ii) an Alkyne or (iii) a Boronic Acid Scheme AIII illustrates several transformations that can provide a compound of the invention, or a precursor thereof, from hydroxy-functionalized compound 13, after conversion to the corresponding mesyl-functional group (com-

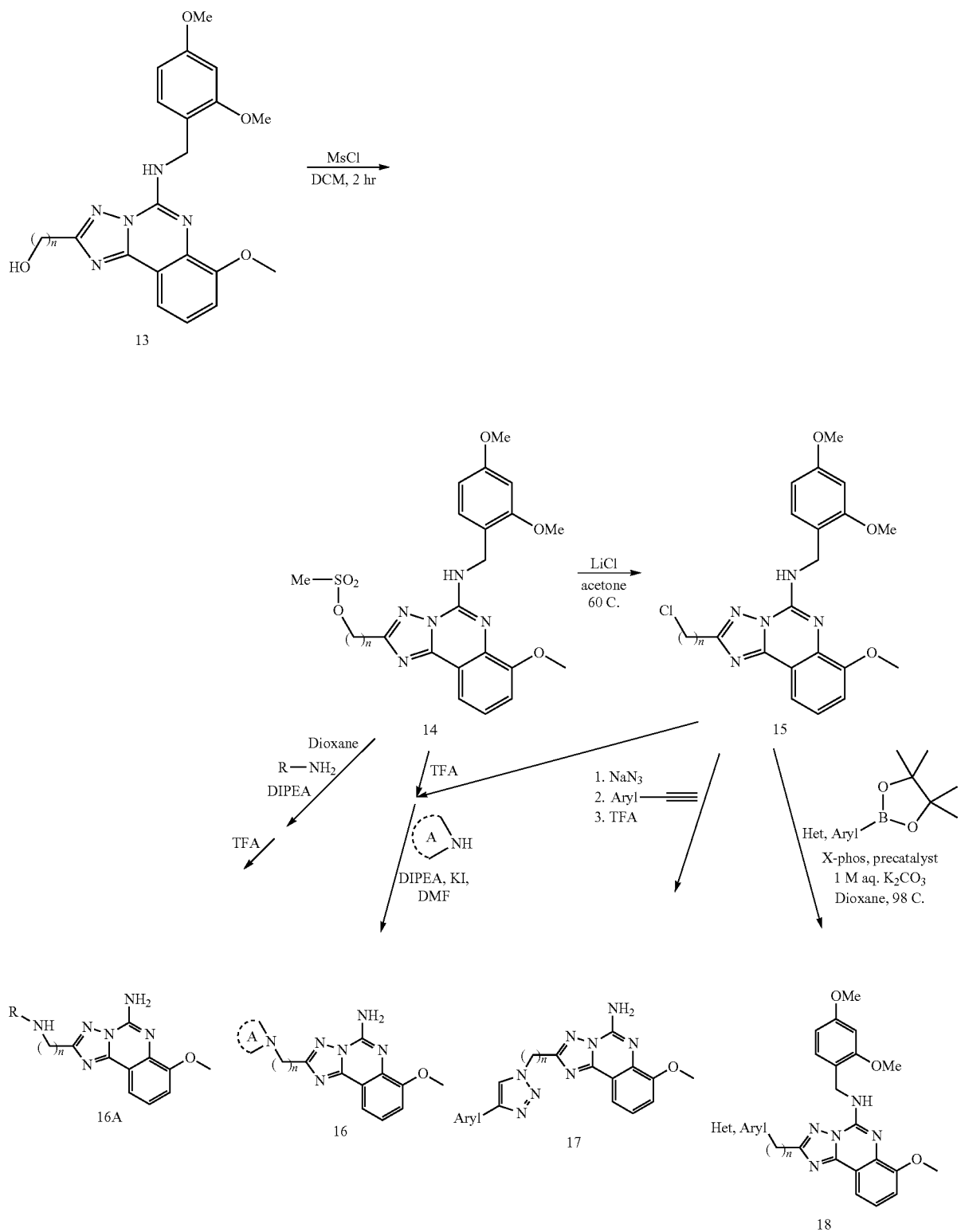

pound 14) via treatment with mesyl chloride (MsCl). Compound 14 can subsequently be reacted with a primary amine and the product deprotected to provide an amine-linked compound of the invention (compound 16A) or a precursor thereof.

Alternatively, compound 14 can be deprotected (using TFA) and reacted with a "left-side" precursor having a suitable reactive nitrogen (for example, a secondary amine shown) under suitable conditions (in the presence of potassium iodide and DIPEA (Hunig's base, diisopropylethylamine), thereby providing compounds of the invention (or a precursor thereof) in which the "left-side" and "right-side" fragments are linked by a secondary-amino or a cyclo-amino moiety (compound 16). Alternatively, the methoxy-functional group of compound 14 is converted to the corresponding methylchloride (compound 15).

As shown, compound 15 can be deprotected and reacted with a secondary- or cycloamine "left-side" precursor in the same manner as compound 14, to provide a compound of the invention or an intermediate thereof, or in the protected form compound 15 can be reacted with an appropriately substituted aryl- or heteroaromatic boronic acid in the presence of a suitable palladium catalyst (in accordance with the similar reaction shown in Scheme AI, above) to provide an aryl-substituted or heteroaryl-substituted triazole of the invention (or an intermediate thereof). As illustrated in Scheme AIII also, compound 15 can alternatively be reacted with sodium azide followed by reaction with a suitable aryl-alkyne, then deprotected to provide triazole-functionalized compounds of the invention or a precursor thereof.

With reference to Schemes AI to AIII, it will be appreciated that any synthetic scheme that provides any of compounds 13, 14, 15 or 19 can be employed to provide a suitable "right-side" precursor utilized in Schemes AI to AIII to ultimately provide a compound of the invention. It will be appreciated as well that any synthetic scheme that provides compound 4 (see Scheme B1) can be employed to provide a suitable quinolin-azole precursor for use in Scheme AII.

In some of the schemes above and throughout, reference is made to "X-phos precatalyst" that is utilized to provide a carbon-carbon bond between a heteroaryl-boronic acid reagent and the chloromethyl substituent shown in the schemes (e.g. compounds 15 and 19). As used herein, this phrase refers to dicyclohexylphosphino-2',4',6'-triisopropyl-1,1'-biphenyl)[2-(2-aminoethyl)phenyl]palladium(II) chloride), which is commercially available. Alternately, in some schemes, the catalyst employed is 1,1'-Bis(diphenylphosphino)ferrocene-palladium(II)dichloride (Pd(dppf)Cl$_2$), (for convenience abbreviated herein as PdCl$_2$(dppf)$_2$-CH$_2$Cl$_2$) also is an article of commerce. In general, suitable aryl-boronic acids and heteroaryl-boronic acids are also commercially available or are readily prepared from commercially available boronic acid compounds.

Preparative Schemes B: Synthetic Pathways Suitable for Preparation of "Right-Side" Precursor Compounds Preparative Schemes BI (which provide free amine products) and BII (infra, which provides protected amine products) illustrate general routes for preparing a "right-Side" precursor that can be employed in the general Schemes AI to AIII, shown above to prepare compounds of the invention. These are followed by several specific examples of preparation of variously functionalized "right-side" precursor compounds useful in synthesis of compounds of the invention.

Schemes BI—Preparation of Heteroaryl-Triazole Compounds of the Invention by Preparation and Cyclization of Heteroarylhydrazine-Substituted Quinazoline-Precursor Compounds.

Scheme BI illustrates several paths for the preparation of triazole precursor compounds. The substituted triazole compounds thus prepared are useful as a precursor in the preparation of substituted pyridine-triazole compounds of the invention, specific examples of which are described herein below.

As shown in the Schemes of BI, one or more —CH$_2$— moieties that will ultimately link the triazolo "core" of the "right-side" fragment of a compound of the invention to the "left-side" fragment can be incorporated into the "right-side" precursor at this stage of the synthesis.

Scheme BI

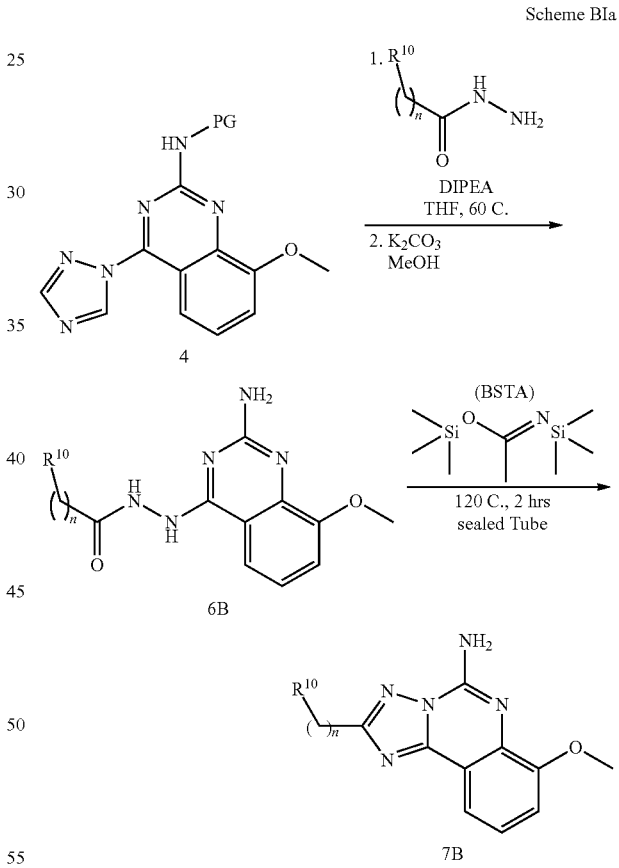

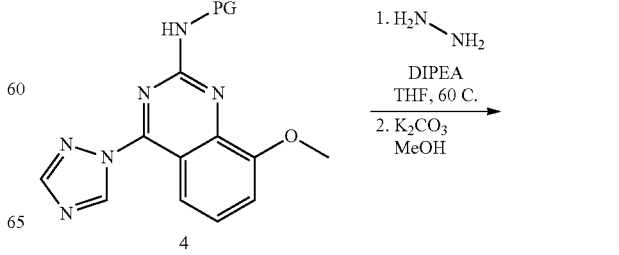

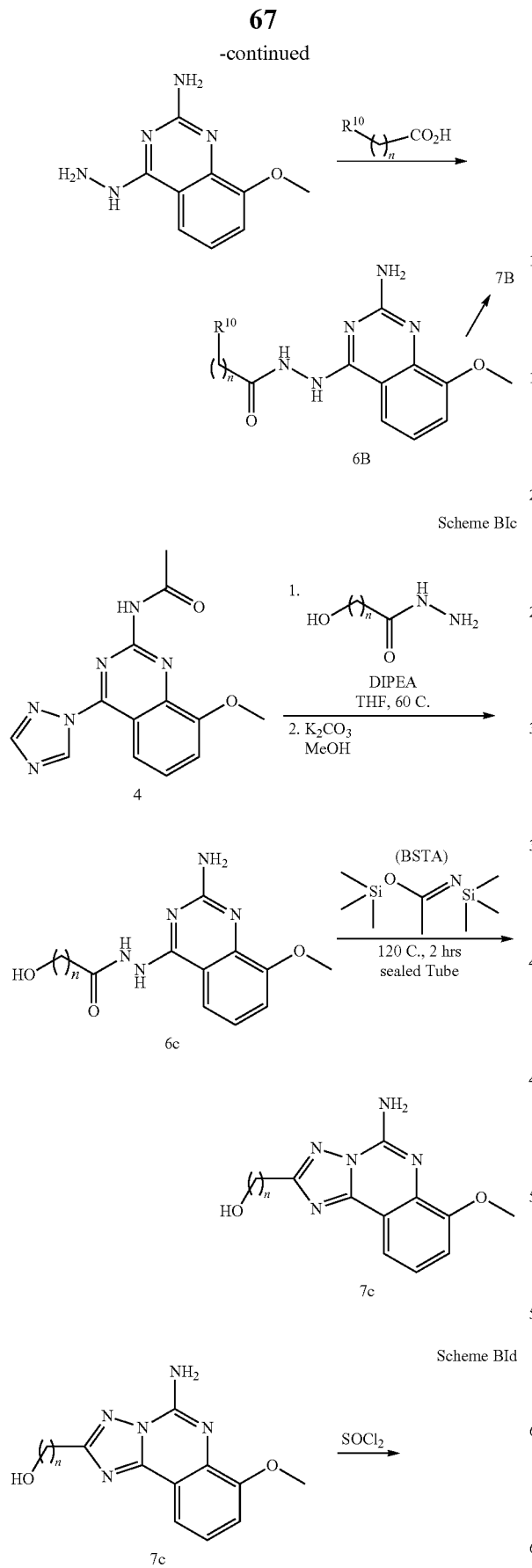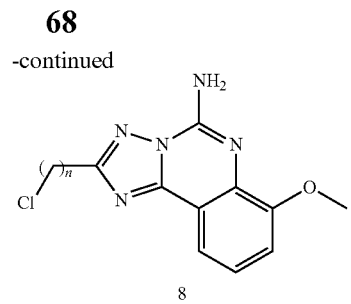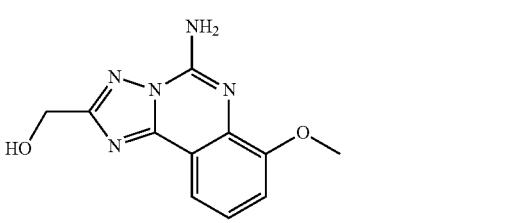

In Schemes of BI, "PG" is an acetyl or dimethoxybenzyl (DMB) protecting group (BIc illustrates an acetyl protecting group).

Schemes BIa and BIb illustrate two routes for preparing a hydrazine precursor in which the hydrazine intermediate ultimately contains an aryl- or heteroaryl-hydrazine-quinoline moiety prior to cyclization (where $R^{10}$ is a substituted aryl or substituted heteroaryl, for example, benzene or halopyridine). In route BIa, a quinazoline precursor, compound 4 can be reacted either with a hydrazine derivative, compound 4B (where $R^{10}$ is a functionalized heteroaryl) and subsequently deprotected to provide compound 6B. In route BIb, compound 4 can be reacted with hydrazine directly, deprotected to provide a hydrazinyl-quinazolin-amine intermediate, and the hydrazinyl-quinolin-amine subsequently reacted with an $R^{10}$-acid, wherein $R^{10}$ is a functionalized heteroaryl moiety, for example, 2-(2-bromopyridin-3-yl) acetic acid, to provide compound 6B. Prepared by either route, the hydrazinyl-quinoline intermediate, 6B, can be cyclized to provide a triazole compound of the invention. As mentioned herein, this is also useful for providing an $R^{10}$-substituted triazole precursor containing one or more reactive substituents that can be subsequently derivatized to provide additional compounds of the invention. Scheme BIc illustrates the use of a hydrazine derivative that provides a hydroxy-functionalized triazole compound (compound 7c), and Scheme BId illustrates conversion of the alcohol-functionalized triazole of compound 7c to the corresponding chloride compound 8. The latter two routes of Scheme BI provide a "right-side" precursor which is widely useful in coupling piperazine "left-side" precursor compounds, as is illustrated herein.

Scheme BIc is illustrated further by the preparation of (5-amino-7-methoxy-[1,2,4]triazolo[1,5-c]quinazolin-2-yl)methanol (compound 7c1) in accordance therewith:

Accordingly, Compound 7c1 was prepared by taking a portion of compound 4 (4.0 g, 14.1 mmol) thus prepared suspended in THF (300 ml). To the suspension was added 2-hydroxyacetohydrazide (1.39 g, 15.5 mmol, compound 4a wherein "n"=1), followed by DIPEA (1.71 g, 17.9 mmol). This mixture was stirred at 60° C. for 48 h, then concentrated in vacuo. The residue thus obtained was dissolved in MeOH (200 ml) and H₂O (100 mL). K₂CO₃ was added. The mixture was stirred at 65° C. for 2 h, cooled to RT. MeOH was removed in vacuo. The precipitates were collected by filtration, cooled to 0° C., washed with H₂O, DCM/Hexanes (1:1), and dried in vacuum oven to afford N'-(2-amino-8-methoxyquinazolin-4-yl)-2-hydroxyacetohydrazide (compound 6c1, which is compound 6c wherein "n"=1). The identity of the product was confirmed by LC/MS in accordance with the procedure described herein (LC/MS=264 [M+1]).

A portion of compound 6c1 thus prepared (3.5 g, 13.3 mmol) was stirred with N,O-Bis(Trimethylsilyl)acetamide (100 mL) at 120° C. for 3 h, cooled to RT, concentrated in vacuo with heating to remove trimethylsilyl N-(trimethylsilyl)acetimidate completely. MeOH was added to the residue and the mixture was concentrated in vacuo. The solids obtained were suspended in MeOH, cooled and filtered. The precipitate were washed with MeOH, dried and concentrated to afford (5-amino-7-methoxy-[1,2,4]triazolo[1,5-c]quinazolin-2-yl)methanol (compound 7c1). The identity of the product was confirmed by LC/MS in accordance with the procedure described herein (LC/MS=246 [M+1]).

In the same manner, Scheme BId is illustrated by the preparation of compound 8a (compound 8 wherein "n"=1) from compound 7c1:

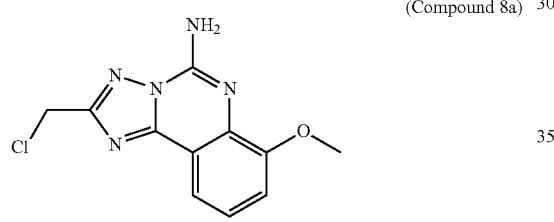

(Compound 8a)

Thus, with reference to Scheme BId, above, a portion of compound 7c1 previously prepared (2.8 g, 11.4 mmol) was mixed with SOCl₂ (10 ml) and the mixture stirred at 65° C. for 45 min. The mixture was then cooled to RT, concentrated to remove SOCl₂ completely, and the residue was suspended in DCM and filtered. The precipitates were collected and dried to afford 2-(chloromethyl)-7-methoxy-[1,2,4]triazolo[1,5-c]quinazolin-5-amine (compound 8a). The identity of the product was confirmed by LC/MS in accordance with the procedure described herein (LC/MS=264 [M+1]).

Preparative Schemes P: Preparation of Triazole Precursors

Scheme PI illustrates the preparation of compound PI-4, useful in providing "right-side" triazole precursor compounds (see e.g., Schemes BIa to BIc, above), from commercially available 2-amino-3-methoxy-benzoic acid.

Scheme PI

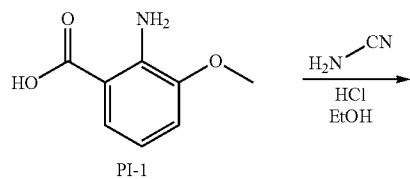

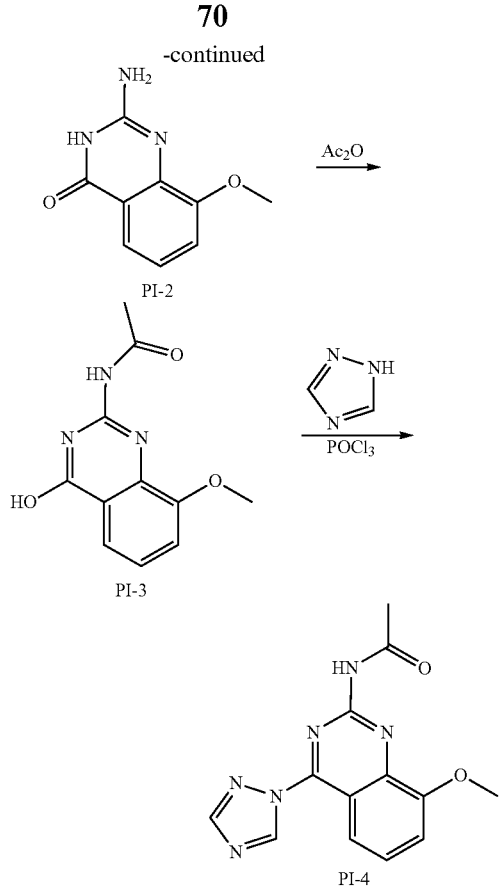

Preparation of N-(8-methoxy-4-(1H-1,2,4-triazol-1-yl)quinazolin-2-yl)acetamide (compound PI-4)

N-(8-methoxy-4-(1H-1,2,4-triazol-1-yl)quinazolin-2-yl)acetamide (compound PI-4) was prepared from a benzoic acid starting material in accordance with Scheme PI by adding into a solution of 2-amino-3-methoxybenzoic acid (compound PI-1) (50 g, 299 mmol) in EtOH (400 ml), cyanamide (18.86 g, 449 mmol) and concentrated HCl (12 ml, 299 mmol). The reaction mixture thus provided was refluxed overnight and then cooled to room temperature. The precipitates were collected through filtration, washing with cold ethanol to yield compound PI-2 (50 g). A portion of compound PI-2 thus provided (10 g, 52.3 mmol) was suspended in acetic anhydride (60 ml, 52.3 mmol). The suspension was placed into a sealed tube and heated at 130° C. for 40 minutes, providing N-(4-hydroxy-8-methoxyquinazolin-2-yl)acetamide (compound PI-3). The identity of the product was confirmed by LC/MS in accordance with the procedure described herein (LC/MS=259 [M+1]).

In a subsequent step, a portion of compound PI-3 thus provided (7 g, 30.0 mmol) was suspended in acetonitrile (300 ml) and added thereto was 1,2,4-triazole (20.73 g, 300 mmol), DIPEA (15.31 ml, 90 mmol), and then dropwise was added POCl₃ (8.22 ml, 90 mmol). This reaction mixture was stirred at room temperature overnight. The yellow precipitates formed were filtered and washed with EtOH twice and then ether to afford N-(8-methoxy-4-(1H-1,2,4-triazol-1-yl)quinazolin-2-yl)acetamide (compound PI-4).

The PI synthetic scheme was carried out by substituting 3-hydroxypropanehydrazide (compound 4a in Scheme BI where "n"=2) in place of 2-hydroxyacetohydrazide used in the previous preparative example. When this substitution was made, scheme PI provided 2-(2-chloroethyl)-7-methoxy-[1,2,4]triazolo[1,5-c]quinazolin-5-amine (compound 8b, compound 8 in Scheme BI where "n"=2). Isolation and purification of 8b was carried out in a DCM/Hexane mixture instead of DCM alone, and the identity of the product was confirmed by LC/MS (LC/MS=279 [M+1]).

When the PI synthetic procedure was carried out using 4-hydroxybutanehydrazide (compound 4a in Scheme BI where "n"=3) in place of 3-hydroxypropanehydrazide used in the previous preparative example, producing thereby 2-(2-chloropropyl)-7-methoxy-[1,2,4]triazolo[1,5-c]quinazolin-5-amine (compound 8c, compound 8 in Scheme BI where "n"=3). Compound 8c was isolated by evacuating the SOCl$_2$ from the reaction mixture and using the residue as prepared. The product was confirmed by LC/MS (LC/MS=293 [M+1]).

It will be appreciated that preparative scheme PI can be carried out starting with other methoxy-benzoic acid starting materials in place of compound PI-1 (2-amino-3-methoxy-benzoic acid) to provide variously-substituted "right-side" triazole precursors for use in preparing compounds of the invention. For example, carrying out Scheme PI using 2-amino-5-fluoro-3-methoxybenzoic acid enables, after a process of Scheme BI, the provision of compound 8d (2-(chloromethyl)-9-fluoro-7-methoxy-[1, 2, 4]triazolo[1,5-c]quinazolin-5, LC/MS=282.1 [M+1]). In the same manner, employing 2-amino-4-fluoro-3-methoxybenzoic acid enables the preparation of compound 8e.

It will be appreciated that in some procedures employing fluorinated amino-methoxybenzoic acid starting materials, the step of preparing an acetamide-protected analog of compound 3 may be eliminated and the free-base may be employed in the reactions instead of employing an acetamide-protected form of the compound. Such a scheme is illustrated in preparative example PII, wherein compound 8F is prepared starting with 2-amino-4,6-difluorobenzoic acid (compound PIM).

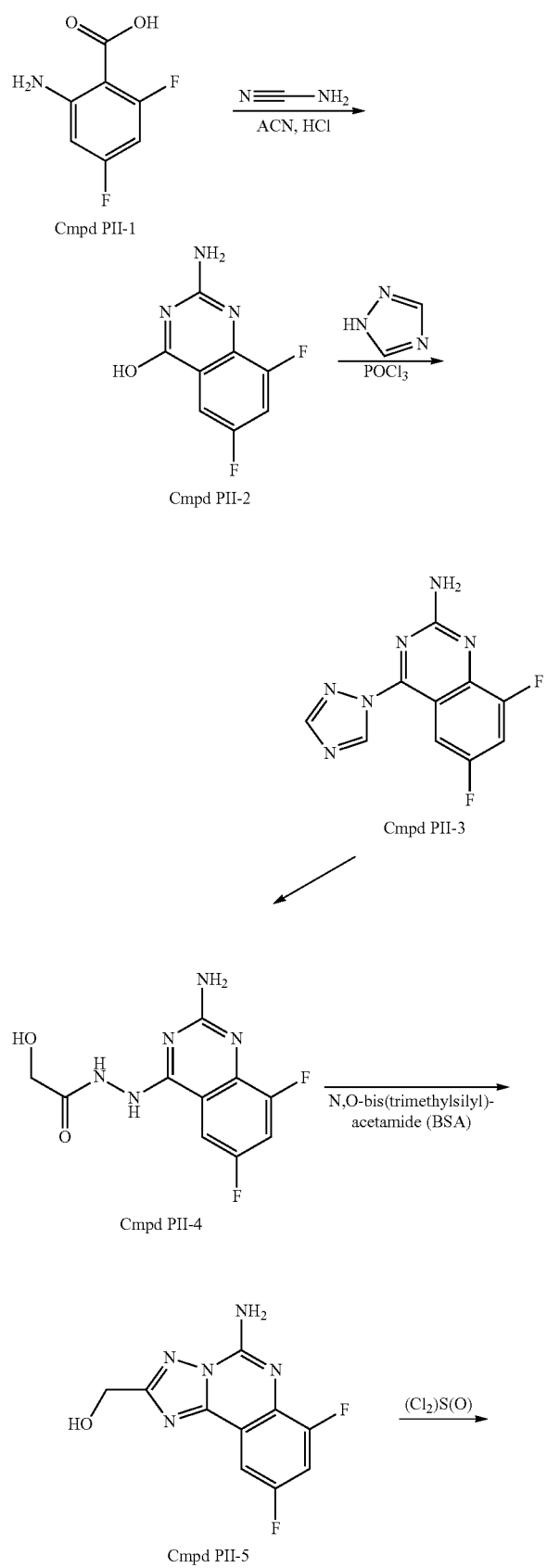

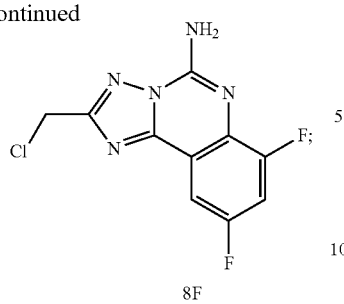

8F

Step A: Preparation of 2-amino-6,8-difluoroquinazolin-4-ol (Cmpd PII-2)

To a solution of the 2-amino-4,6-difluorobenzoic acid (Cmpd PII-1, 5 g, 28.9 mmol)) in acetonitrile (20 ml) was added cyanoamide (1.821 g, 43.3 mmol)) and concentrated hydrochloric acid (3 ml). Reaction mixture was refluxed overnight, cooled to room temperature, and then the precipitate was collected through filtration, washing with acetonitrile to yield the desired product 2-amino-6,8-difluoroquinazolin-4-ol (Cmpd PII-2). Retention time: 0.10, LC/MS=198 [M+1].

Step B: Preparation of 6,8-difluoro-4-(1H-1,2,4-triazol-1-yl)quinazolin-2-amine (Cmpd PII-3)

To a stirred solution of 2-amino-6,8-difluoroquinazolin-4-ol (2 g, 10.14 mmol) and triazole (7.01 g, 101 mmol) in acetonitrile (30 mL), $POCl_3$ (10.63 ml, 60.9 mmol) was added slowly in one over 1 h making sure to maintain the temperature below 60° C. The reaction was stirred overnight at room temperature, cooled to room temperature, and then the precipitate was collected through filtration, washing with acetonitrile to yield the desired product 6,8-difluoro-4-(1H-1,2,4-triazol-1-yl)quinazolin-2-amine (Cmpd PII-3) as a colorless solid. Retention time: 0.20, LC/MS=249 [M+1].

Step C: Preparation of N'-(2-amino-6,8-difluoroquinazolin-4-yl)-2-hydroxyacetohydrazide (Cmpd PII-4)

Into a stirred mixture of 2-hydroxyacetohydrazide (0.18 g, 2.0 mmol) in 20 mL of THF was added 6,8-difluoro-4-(1H-1,2,4-triazol-1-yl)quinazolin-2-amine (Cmpd PII-3, 0.18 g, 2.0 mmol). The mixture was stirred at room temperature overnight, then the solvent was evaporated under reduced pressure. DCM was added to the residue and the solid was filtered off. The yellow solid was dissolved in water and the residue was filtered off and retained. Acetonitrile was added into the aqueous phase with stirring until precipation and the solid was filtered again. Solids were collected and dried in vacuo at room temperature to give N'-(2-amino-6,8-difluoroquinazolin-4-yl)-2-hydroxyacetohydrazide (Cmpd PII-4) as a yellow solid. The identity of the product was verified by LC/MS—Retention time: 0.54, LC/MS=270 [M+1].

Step D: Preparation of (5-amino-7,9-difluoro-[1,2,4]triazolo[1,5-c]quinazolin-2-yl)methanol (Cmpd PII-5)

N'-(2-amino-6,8-difluoroquinazolin-4-yl)-2-hydroxyacetohydrazide (Cmpd PII-4, 0.8 g, 2.97 mmol) was added to a stirred, cooled room temperature mixture of BSA (12 g, 60 mmol) and the mixture was stirred at 120° C. for 2 h. After 2 hours, BSA was removed under vacuum and 5 mL of MeOH was added slowly. The solvent was removed under vacuum, water was added, and the mixture was filtered and washed with dichloromethane to give (5-amino-7,9-difluoro-[1,2,4]triazolo[1,5-c]quinazolin-2-yl)methanol as yellow solid. Retention time: 1.35, LC/MS=252[M+1].

Step E: Preparation of 2-(chloromethyl)-7,9-difluoro-[1,2,4]triazolo[1,5-c]quinazolin-5-amine (8F)

A portion of Cmpd PII-5, prepared in the previous step (0.4 g, 1.60 mmol) was suspended in 5 mL of $SOCl_2$ and DCM (10 mL). The mixture was stirred at RT for 1 h, concentrated in vacuo to remove $SOCl_2$ completely. The residue was suspended in DCM/Hex (1:2), cooled to 0° C., filtered, and the solid was dried in vacuum oven to give 2-(chloromethyl)-7,9-difluoro-[1,2,4]triazolo[1,5-c]quinazolin-5-amine. Retention time: 1.68, LC/MS=270 [M+1].

It will be appreciated that by using the PI and PII synthesis procedures described above with variously substituted aminobenzoic acid starting material, other precursors with various substituents on the "aryl-ring" of the triazole "right-side" precursor compound may be prepared. Accordingly, following the procedure of PI with 2-amino-3-bromobenzoic acid will provide compound 8G, and employing 2-amino-3-trifluoromethyl-benzoinc acid as a starting material will provide compound 8H:

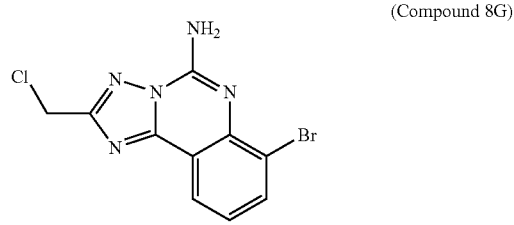

(Compound 8G)

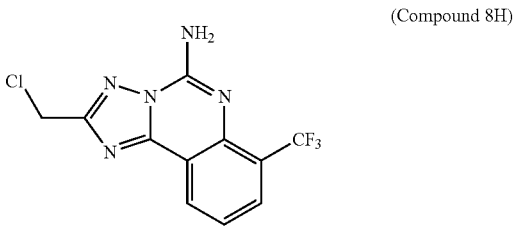

(Compound 8H)

Moreover, compound 8G can be employed to prepare additional analogs, for example, using Scheme PI(a), the cyano-functionalized analog can be prepared.

Scheme PI(a)

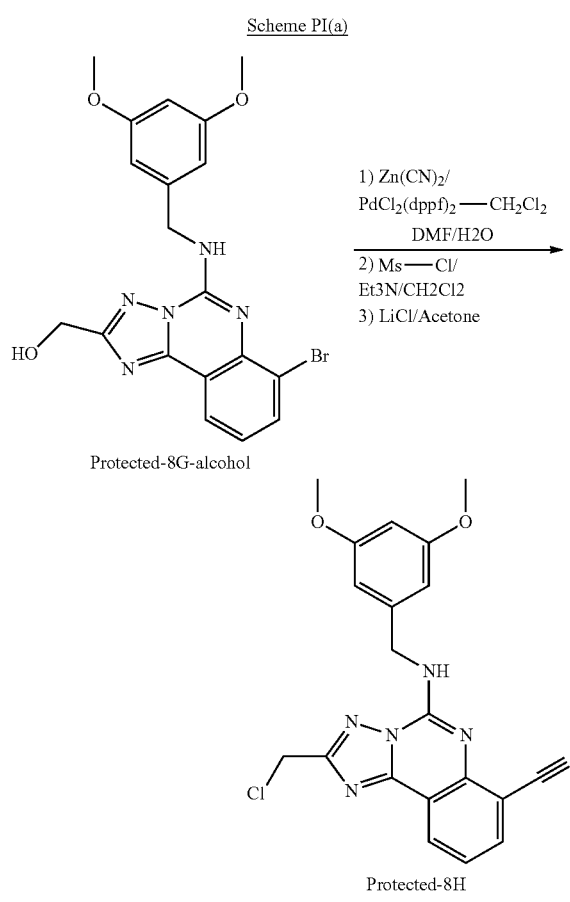

Protected-8G-alcohol

1) Zn(CN)₂/
PdCl₂(dppf)₂—CH₂Cl₂
DMF/H2O
2) Ms—Cl/
Et3N/CH2Cl2
3) LiCl/Acetone

Protected-8H

In accordance with Scheme PI(a), a mixture of Protected-8G-alcohol prepared in accordance with PI (200 mg; 0.45 mmol), zinc cyanide (31.7 mg; 0.27 mmol) and PdCl₂(dppf)₂:CH₂Cl₂ were dissolved in DMF (1 mL) and water (0.1 mL). The resulting clear red solution was degassed with nitrogen, stirred and heated at 120° C. for 14 hr. MS analysis of the reaction mixture showed absence of the starting bromo tricyclic alcohol and presence of the product nitrile (MH⁺=391). The reaction mixture was quenched with water, and organics were extracted with EtOAc. The organic extract was further washed with water, brine and dried over solid anhydrous Na₂SO₄. The crude product was purified by preparative TLC, developing the plate with EtOAc-CH₂Cl₂ (1:1) to provide the cyano analog of protected 8G-alcohol (herein CN-8G-alcohol isolated as beige solid).

The compound CN-8G-alcohol thus prepared was dissolved (140 mg; 0.36 mmol) in CH₂Cl₂ (2 mL) and CDCl₃ (2 mL). The solution was cooled in an ice bath and treated sequentially with Et₃N (40 mg; 55 uL; 0.395 mmol) and MsCl (49 mg; 0.43 mmol), taking care not to use even a slight excess of Et₃N to avoid quaternary salt formation. The ice bath was removed after 5 minutes, and the reaction mixture was stirred at RT for 45 minutes when the analysis (TLC, MS) showed absence of alcohol. The reaction mixture was diluted with EtOAc and washed with water, brine, dried and concentrated to obtain the crude mesylate.

The crude mesylate prepared in the previous step was redissolved in acetone (3 mL), treated with solid LiCl (76 mg; 1.79 mmol) and was stirred with heating at 58° C. for 3 hr. After confirming the complete formation of the tricyclic chloride (MH⁺=408/410), the reaction mixture was cooled to RT and acetone was removed under house vacuum. The residue was dissolved in CH₂Cl₂/CHCl₃ (4:1) and washed with water, brine and concentrated to obtain a beige solid. The crude product thus obtained was purified by preparative TLC (30% EtOAc-CH₂Cl₂) to furnish compound protected-8H as off-white solid.

General Preparative Scheme BII: Preparation of "Protected-Amine," "Right-Side" Triazole Precursors Scheme BII illustrates the preparation of a "protected-amine" "right-side" precursor from commercially available 2-amino-3-methoxy-benzoic acid. As was shown in Scheme BI, Scheme BII illustrates that one or more —CH₂— moieties, which will ultimately link the triazolo "core" portion of the "right-side" fragment of a compound of the invention to the "left-side" fragment, can be incorporated into the "Right-side" precursor at this stage of the synthesis.

Scheme BII

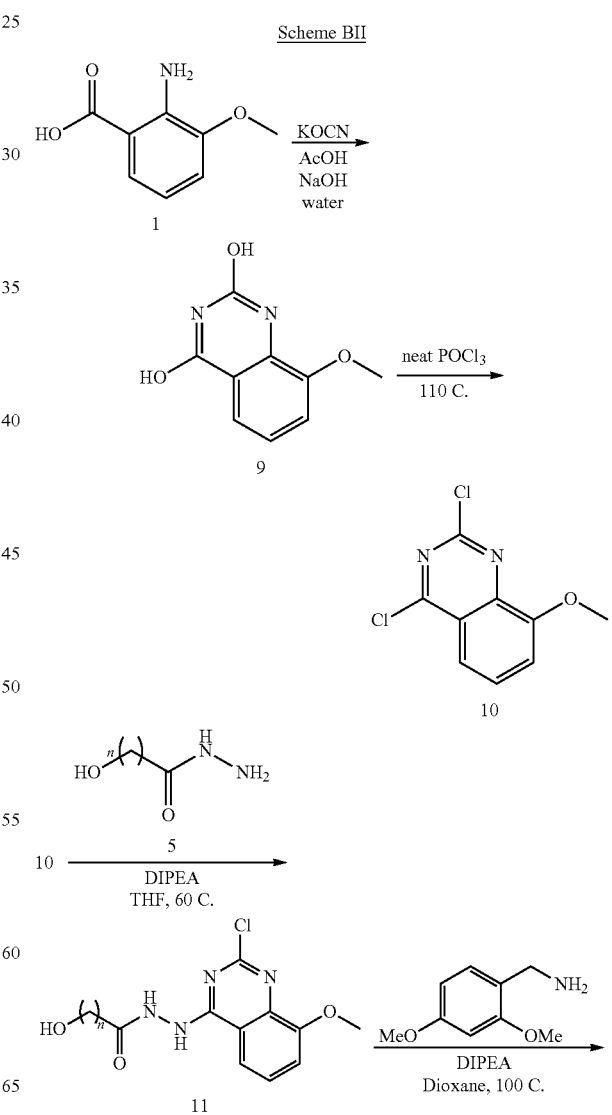

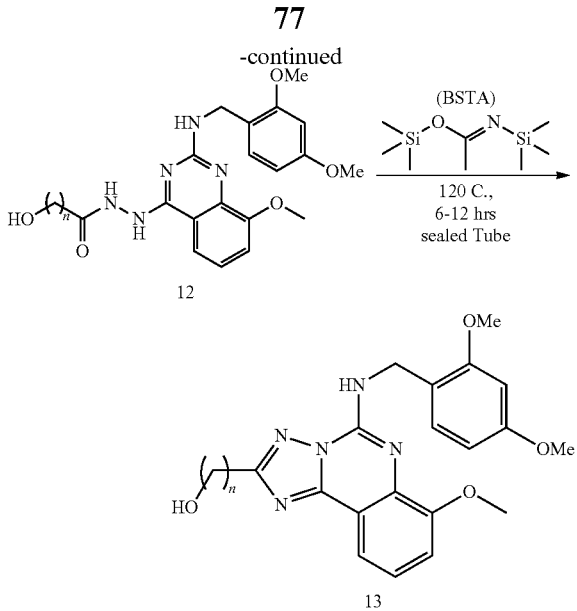

Preparative Example PIII: Preparation of (5-(2,4-dimethoxybenzylamino)-7-methoxy-[1,2,4]triazolo[1,5-c]quinazolin-2-yl)methanol (compound 13a) in accordance with Scheme BII

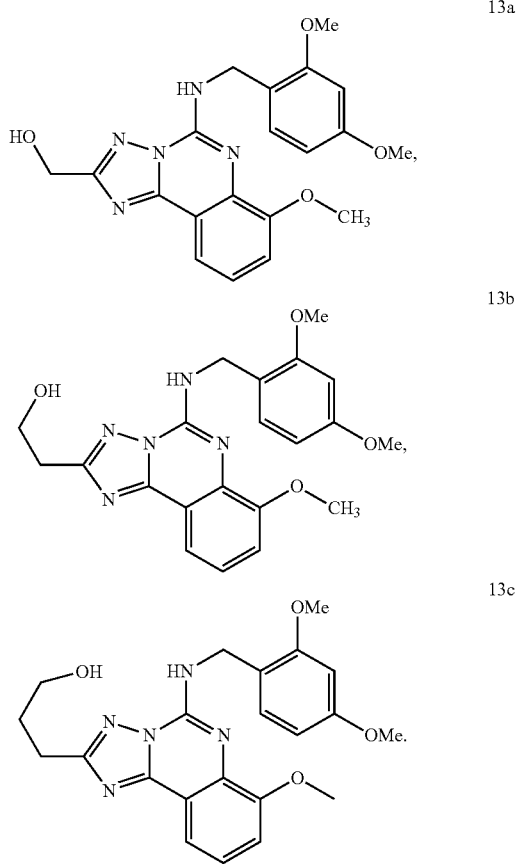 [SMILES: COc1ccc(CNc2nc3c(OC)cccc3c3nc(CO)nn23)c(OC)c1 ; COc1ccc(CNc2nc3c(OC)cccc3c3nc(CCO)nn23)c(OC)c1 ; COc1ccc(CNc2nc3c(OC)cccc3c3nc(CCCO)nn23)c(OC)c1]

With reference to Scheme BII, above, (5-(2,4-dimethoxybenzylamino)-7-methoxy-[1,2,4]triazolo[1,5-c]quinazolin-2-yl)methanol (compound 13a, which is compound 13 of Scheme BII where "n"=1) was prepared starting from compound 1 by placing into a reaction vessel a suspension of compound 1 (3 g, 17.95 mmol) in water (100 ml) and acetic acid (1.099 ml, 19.20 mmol) maintained at 55-60° C., and adding thereto a solution of KOCN (3.49 g, 43.1 mmol) in water (7 mL). After about 4 hours of stirring at 55-60° C., the reaction was cooled to ambient temperature and solid NaOH (31.6 g, 790 mmol, 35-44eq) was added quickly in one portion.

The resultant pale brownish cloudy solution became clear and then became white murky solution after 10 min. The reaction mixture was cooled to 0° C. and Conc. HCl (around 38 mL) was added to make pH 4-5 while maintaining the reaction mixture at 0° C., generating a white precipitate. The reaction mixture was filtered, and the solids obtained were washed with water (500 mL) and dried under vac. oven overnight to afford compound 9. The identity of compound 9 was verified by LC/MS in accordance with the procedure listed herein (193 [M+1]

A stirred suspension of compound 9 prepared above (2.0 g, 10.41 mmol) in neat $POCl_3$ (9.70 ml, 104 mmol) was heated to 105° C. overnight. After 16 hrs, the murky solution became clear and the reaction mixture was cooled down. The $POCl_3$ was evaporated until solution became solid. The crude product thus obtained was mixed with EtOAc (500 mL) and the mixture poured into a 12 L beaker. Aqueous $NaHCO_3$(aq) was added and the mixture was stirred for 30 min. The crude product solids became soluble in EtOAc and any remaining $POCl_3$ was quenched. The resulting organic layer was washed with $NaHCO_3$(aq), and brine solution, dried over MgSO4, filtered and concentrated, yielding pale yellowish solid product, compound 10. The identity of compound 10 was verified by LC/MS in accordance with the procedure listed herein (230 [M+1].

Thus prepared, compound 10 (15.2 g, 66.4 mmol) was dissolved in THF (664 ml), and to this solution was added DIPEA (13.91 ml, 80 mmol) and 2-hydroxyacetohydrazide (with reference to Scheme BII, compound 5 where "n"=1, 5.98 g, 66.4 mmol). The reaction mixture was stirred at 65° C. overnight, then the reaction mixture was cooled to RT and the solvent was evaporated. The crude product was redissolved in DCM and stirred for 30 min providing a pale yellowish precipitate. The precipitate was filtered and washed with DCM then dried in vacuo to afford compound 11a (with reference to Scheme BII, compound 11 wherein "n"=1). The identity of compound 11a was verified by LC/MS in accordance with the procedure listed herein (283 [M+1]).

(Compound 11a)

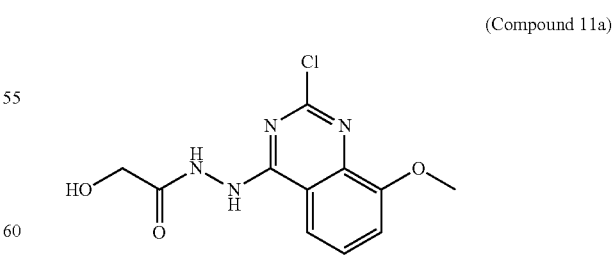

Compound 11a thus obtained (14.7 g, 52.0 mmol) was suspended in dioxane (520 ml) and added thereto was DIPEA (22.71 ml, 130 mmol) and (2,4)-dimethoxyphenylmethanamine (10.16 ml, 67.6 mmol). The reaction mixture was heated to 100° C. for 16 hrs. then cooled to room temperature. The reaction was filtered and washed with dioxane until no yellow solution came out and washed with hexane several times and dried in vacuo to afford compound 12a (with reference to Scheme BII, compound 12, wherein "n"=1). The identity of compound 12a was verified by LC/MS in accordance with the procedure listed herein (414 [M+1]).

Thus obtained, compound 12a (20.3 g, 49.1 mmol) was placed into a tube, BSTA (144 ml, 589 mmol) was added and the tube was sealed. The sealed reaction mixture was heated to 130° C. overnight. Afterward, the reaction mixture was cooled down, transferred to a rotary evaporator and the BSTA was evaporated from the rotary evaporator for one hour in a water bath heated to 70° C.

The crude material thus obtained was dissolved in MeOH (170 mL) and 2.5 mL of conc. HCl was added. The solution became murky and after 10 min, the precipitate that had formed was filtered and washed with water (5×) and the solids were washed 2× with DCM (50 mL) followed by 1× with water, then dried under vac. oven overnight to afford as a pale yellow powder, compound 13a. The identity of compound 13a was verified by LC/MS in accordance with the procedure listed herein (396 [M+1]).

It will be appreciated that by selecting an appropriate hydrazide (compound 5, Scheme BII) analogs of compound 13a having an alkoxy-substituent where "n">1 can be prepared. For example, following Scheme BII using 3-hydroxy-propanehydrazide (Scheme BII, compound 5 where "n"=2) to react with compound 10 in place of 2-hydroxyacetohydrazide used as compound 5 in Preparative Example PII ("n"=1), ultimately yields compound 13b (shown above) from this procedure.

Once the hydroxy-substituted "right-side" precursor is prepared, for example, compounds 13a, 13b, or 13c, the hydroxy-substituted compound can be reacted to provide additional functionality at that location, for example, conversion to the corresponding chloride as shown in Scheme PIV.

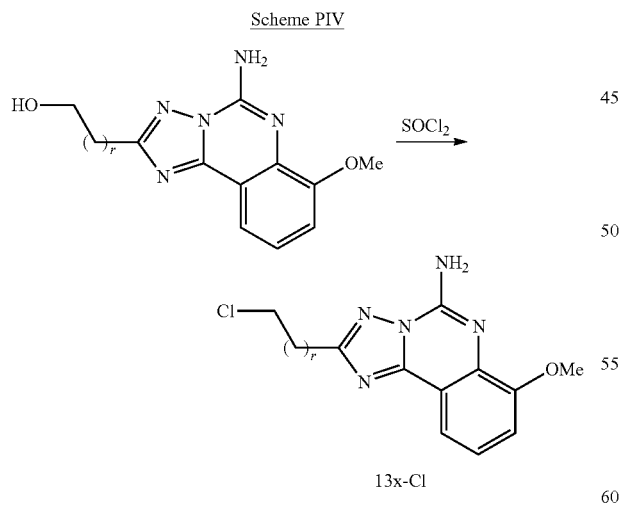

DCM/Hex (1:2), cooled to 0° C., filtered and dried to afford the titled compound LC/MS=279 [M+1].

In the same manner, compound 13c-C1 (13x-C1 where "x" is "c" and "r" is 2) was prepared by suspending 3-(5-amino-7-methoxy-[1,2,4]triazolo[1,5-c]quinazolin-2-yl)propan-1-ol in (240 mg, 0.878 mmol) in SOCl$_2$ (25 ml) and DCM (50 ml). The mixture was stirred at RT for 1 h, concentrated in vacuo to remove SOCl$_2$ completely to afford the titled compound. LC/MS=293 [M+1].

Variations on this procedure can provide a triazolo core with different functionality. For example, a 7-methoxy 9-fluoro-triazole can be prepared in accordance with the following scheme in a similar procedure by starting with -amino-5-fluoro-3-methoxybenzoic acid in accordance with Scheme E3, below.

A variation of synthesis Scheme BII is shown in Scheme PV (below). Thus, after obtaining compound 10 in accordance with Scheme BII, compound 10 was reacted with a hydrazinyl-oxopropanoate to provide compound P11b. In turn, compound 11b was reacted as shown in Scheme PV to provide "right-side" precursor P23, which is useful in preparing amide-substituted triazole compounds of the invention, for example, compounds Ex-153 and Ex-154 (described herein below).

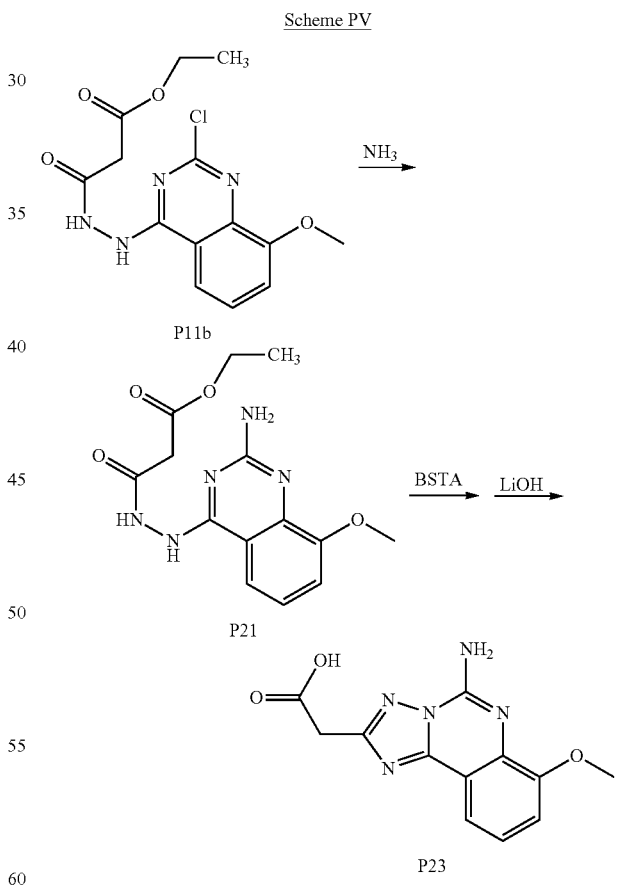

Thus, compound 13b-C1 (13x-C1 where "x" is "b" and "r" is 1) was prepared by suspending 2-(5-amino-7-methoxy-[1,2,4]triazolo[1,5-c]quinazolin-2-yl)ethanol (4 g, 15.4 mmol) in DCM (50 mL) and SOCl$_2$ (50 ml). The mixture was stirred at RT for 1 h, concentrated in vacuo to remove SOCl$_2$ completely. The residue was suspended in In accordance with the foregoing, to a stirred suspension of compound 10 (3.0 g, 13.10 mmol, prepared in accordance with general Scheme BII) in THF (30 mL) was added ethyl 3-hydrazinyl-3-oxopropanoate (2.01 g, 13.75 mmol) and DIPEA (6.86 ml, 39.3 mmol). The reaction mixture was heated to 55° C. overnight then cooled to ambient temp. and the solvent was evaporated. To the residue, DCM and water were added and the mixture extracted with DCM (×3). The organic extract was evaporated to afford compound P11b, (3.1 g, 67%) used as prepared.

To a pressure tube of P11b (2.1 g, 6.20 mmol) was added 90 mL ammonia (2M in isopropanol). The pressure tube was sealed and heated to 105 C overnight. The reaction mixture was cooled to room temperature and evaporated solvent. The crude product, compound P21 (2.72 g, 8.54 mmol), without further purification was mixed with N,O-bistrimethylsilyl acetamide (BSTA, 20.9 ml, 85 mmol) and the mixture sealed in a pressure tube then heated, with stirring, to 130° C. for 4 hrs. The reaction mixture was cooled to ambient temperature, then transferred to a rotary evaporator and the solvent removed. The residue was purified by silica chromatography (1/1 EtOAc/Hex to 10% MeOH/DCM) yielding ethyl 2-(5-amino-7-methoxy-[1,2,4]triazolo[1,5-c]quinazolin-2-yl)acetate. This product was suspended in THF (20 mL) and water (4 mL), mixed with LiOH—H$_2$O. The mixture was stirred at room temperature overnight, then the solvent was evaporated and the residue dried under vac. oven overnight to yield P23.

General Preparation of "Left-Side" Precursors

Preparative Example PVI: Preparation of Piperazine-Functional "Left-Side" Precursors

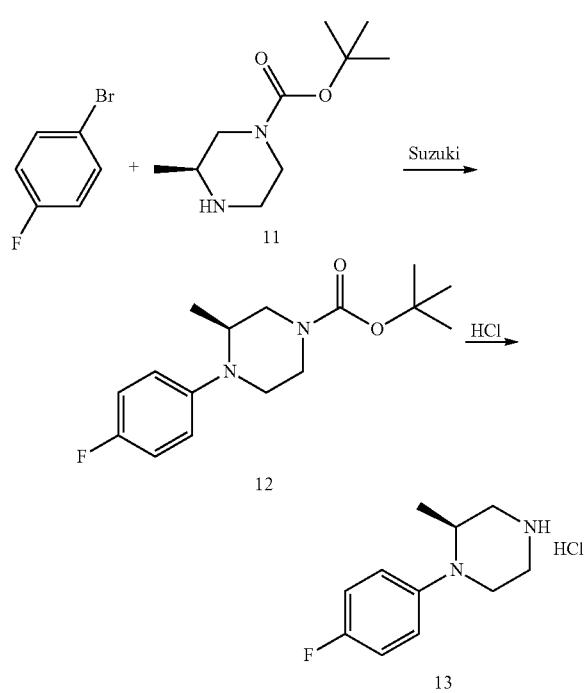

(Step 1) To a microwave tube was added (S)-4-N-Boc-2-methylpiperazine, 11 (250 mg, 1.248 mmol), 4-fluorobromobenzene (240 mg, 1.373 mmol), potassium tert-butoxide (140 mg, 1.248 mmol), Tris(dibenzylideneacetone)dipalladium-chloroform adduct (64.6 mg, 0.062 mmol), 2-dicyclohexylphosphino-2',6'-di-I-propoxy-1,1'-biphenyl (87 mg, 0.187 mmol) and toluene (416 µl). The reaction mixture was microwaved at 100° C. for 2 hrs. The solvent was evaporated and EtOAc was added. The organic layer was washed with water, dried over MgSO4, filtered, and concentrated.

The crude product was purified by ISCO (EtOAc/Hex=1/5) to give the desired product 13, which was confirmed by LC/MS=295 [M+1].

(Step 2) To a stirred solution of 13 (210 mg, 0.713 mmol) in DCM (446 µl) was added 4M HCl in dioxane solution (5 mL). The reaction mixture was stirred at RT overnight.

The solvent was evaporated and the crude product was concentrated under high vac. to give the desired product, 13, which yielded LC/MS=195 [M+1].

EXAMPLES

Example 1: Preparation of Cycloamine-Triazole Compounds in Accordance with Scheme E1—Coupling "Right-Side" Piperazine-Precursor with Aryl or Heteroaryl-Halo Precursor Piperazine precursor compounds were prepared using the reaction chemistry shown in Scheme AIII to provide Ex-E2-pre piperazine-functionalized compounds (where the piperazine functional group is HN—R"). Compounds of the invention were prepared from the piperazine precursor in accordance with Scheme E1.

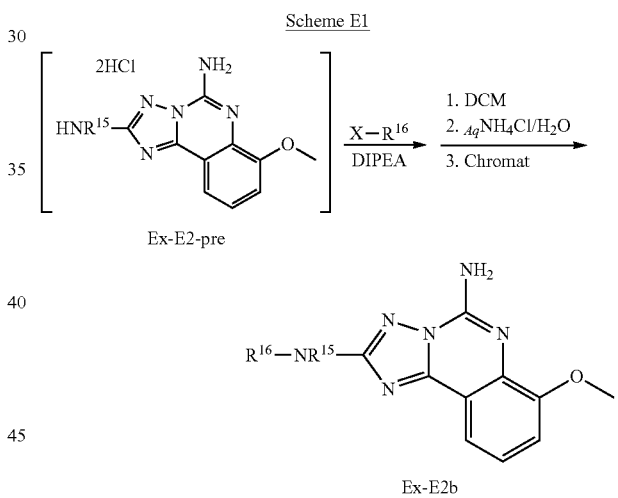

Thus, in accordance with Scheme E1, the compound of Ex-199 was prepared by suspending 80 mg of dihydrichloride salt (80 mg) of a compound of 2-((2,2-dimethylpiperazin-1-yl)methyl)-7-methoxy-[1,2,4]triazolo[1,5-c]quinazolin-5-amine (the compound of Formula Ex-E2-pre where HNR[15] is as shown below in Table V for Ex-199) was suspended in DIPEA (101 µL) with 2-fluoro-5-(trifluoromethyl)pyridine (47.8 mg, reagent X—R[16] for Ex-199 in Table V) and heated at 80° C. overnight, then diluted with DCM. The organic layer was separated, washed with sat. aq NHCl$_4$ then water, dried over MgSO$_4$, filtered and concentrated. The residue was purified by silica chromatography (EtOAc/Hex=1/1 to 100% EtOAc) to yield Ex-199.

All of the compounds of the form Ex-E2b from Scheme E1 shown in Table V were prepared in a similar manner from the appropriate piperazine precursor and appropriate X—R[16] reagent.

TABLE V

| Example No | HN—R¹⁵ | X—R¹⁶ | R¹⁶—NR¹⁵— | LC/MS [M + 1] |
|---|---|---|---|---|
| Ex-199 | | | | 487 [M + 1] |
| Ex-200 | | | | 514 [M + 1] |
| Ex-201 | | | | 464 [M + 1] |
| Ex-202 | | | | 464 [M + 1] |
| Ex-203 | | | | 538 [M + 1] |
| Ex-204 | | | | 488 [M + 1] |
| Ex-205 | | | | 511 [M + 1] |

Example 2: Preparation of Cycloamine-Triazole and Derivative Compounds in Accordance with Scheme AIII—Coupling "Right-Side" Precursor with Amine or Cycloamine Exemplified in Scheme E3 with Piperazine Scheme E2 illustrates preparation of compounds of the invention in accordance with general Scheme AIII to prepare compounds of the structure of Compound 16 by coupling a functionalized piperidine reagent and a suitable chloro-functionalized "right-side" triazole precursor.

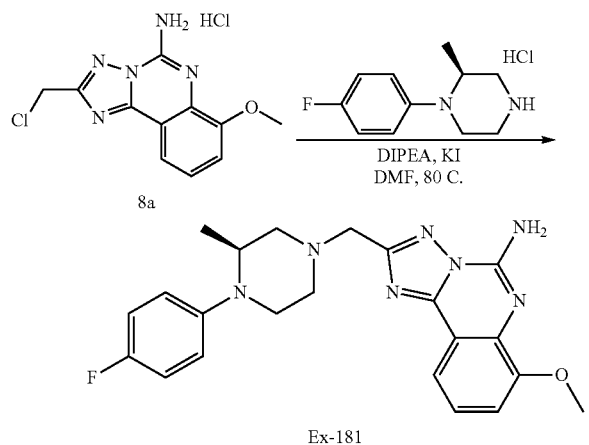

Scheme E2

Ex-181

Thus, in accordance with Scheme E2, to a stirred solution of the hydridochloride salt of compound 8a (80 mg, 0.267 mmol) in DMF (2665 µl) was added piperazine (78 mg, 0.293 mmol, prepared in accordance with preparative Example PIII, above), DIPEA (186 µl, 1.066 mmol), and KI (8.85 mg, 0.053 mmol). The reaction mixture was heated to 80° C. and stirred overnight. After cooling to ambient, NH₃Cl(aq) was added. The resulting precipitate was filtered, washed, dried and purified by flash chromatography (ISCO) (EtOAc/Hex=1/1 to 10% MeOH/DCM) to give compound EX-181 (62 mg). The identity of the product was confirmed by LC/MS (LC/MS=422 [M+1]).

Using the coupling procedure described above in Scheme E2 and various "Left-side" amino-functionalized "left-side" precursor compounds, additional examples of compounds of the invention described above were prepared which have the general structure:

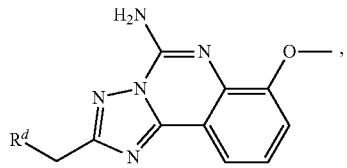

where R$^d$ is defined in Table VI

TABLE VI

| Example No. | R$^d$ | LC-MS |
|---|---|---|
| Ex-10 | *(structure: F-phenyl-piperazine with methyl)* | 440 [M + 1] |
| Ex-180 | *(structure: methoxyphenyl-dimethylpiperazine)* | 448 [M + 1] |
| Ex-181 | *(structure: F-phenyl-methylpiperazine)* | 422 [M + 1]. |
| Ex-182 | *(structure: F-pyridyl-methylpiperazine)* | 423 [M + 1]. |
| Ex-183 | *(structure: F-phenyl-dimethylpiperazine)* | 436 [M + 1]. |
| Ex-187 | *(structure: methoxyphenyl-dimethylpiperazine)* | 448 [M + 1] |
| Ex-188 | *(structure: ethoxycarbonyl-spirocyclopropyl-piperazine)* | 412 [M + 1]. |
| Ex-189 | *(structure: methoxyethylphenyl-spirocyclopropyl-piperazine)* | 490 [M + 1] |
| Ex-190 | *(structure: methoxyethoxyphenyl-spirocyclopropyl-piperazine)* | 490 [M + 1] |
| Ex-191 | *(structure: F-phenyl-spirocyclopropyl-piperazine)* | 434 [M + 1]. |
| Ex-192 | *(structure: F-ethyl-spirocyclopropyl-piperazine)* | 386 [M + 1]. |

TABLE VI-continued

| Example No. | R^d | LC-MS |
|---|---|---|
| Ex-193 | 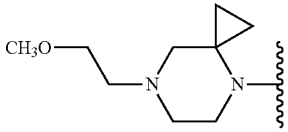 | 398 [M + 1]. |
| Ex-194 | 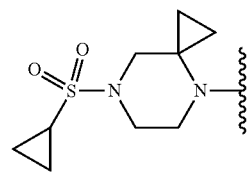 [SMILES: *N1CCN(S(=O)(=O)C2CC2)CC12CC2] | 444 [M + 1]. |
| Ex-195 | 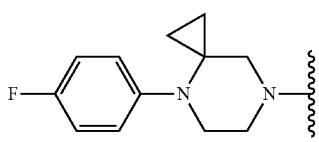 [SMILES: *N1CCN(c2ccc(F)cc2)C2(CC2)C1] | 434 [M + 1]. |
| Ex-196 | 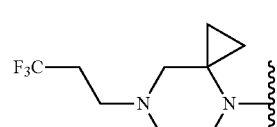 | 436 [M + 1]. |
| Ex-197 | 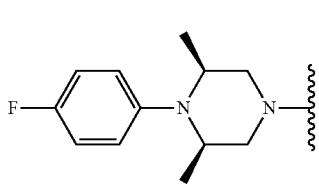 [SMILES: *N1C[C@@H](C)N(c2ccc(F)cc2)[C@@H](C)C1] | 436 [M + 1]. |
| Ex-198 | 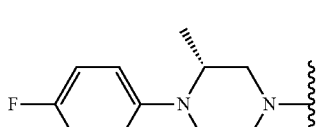 | 422 [M + 1]. |
| Ex-208 | 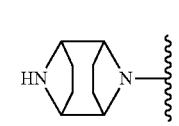 | 366 [M + 1]. |
| Ex-209 | 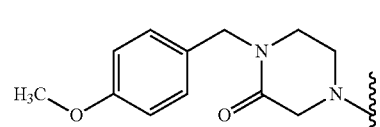 | 448 [M + 1] |
| Ex-210 | 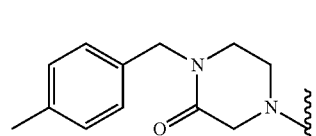 | 432 [M + 1] |
| Ex-34 | 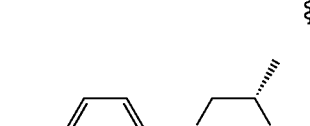 | Rt = 1.84 [M + 1] = 438 |
| Ex-35 | 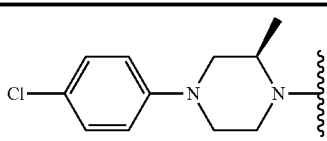 | Rt = 1.81 [M + 1] = 438 |
| Ex-43 | 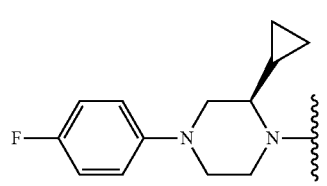 [SMILES: *N1CCN(c2ccc(F)cc2)C[C@H]1C1CC1] | 448 [M + 1]. |
| Ex-44 | 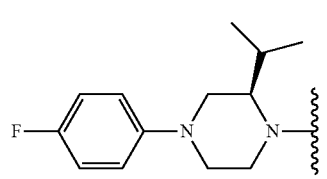 [SMILES: *N1CCN(c2ccc(F)cc2)C[C@H]1C(C)C] | 450 [M + 1]. |
| Ex-45 | 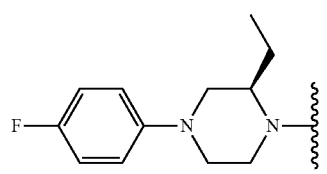 [SMILES: *N1CCN(c2ccc(F)cc2)C[C@H]1CC] | 436 [M + 1]. |

Using the coupling procedure described above in Scheme E2, an appropriate "right-side" precursor and various amino-functionalized "Left-side" precursor compounds, additional examples of compounds of the invention were prepared which have the general structure:

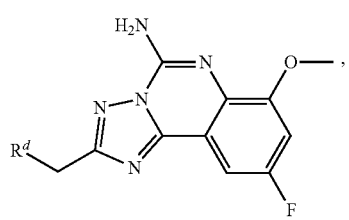

where $R^d$ is defined in Table VIa

TABLE VIa

| Example No. | R^d | LC-MS |
|---|---|---|
| Ex-178 | 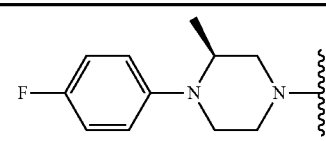 | 422 [M + 1] |
| Ex-184 | 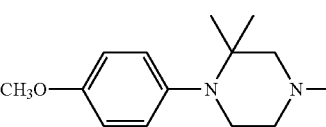 | 466 [M + 1] |

TABLE VIa-continued

| Example No. | $R^d$ | LC-MS |
|---|---|---|
| Ex-185 | Br-phenyl-N-(2,2-dimethylpiperazin-1-yl) | 515 [M + 1] |
| Ex-186 | 3-methoxyphenyl-N-(2,2-dimethylpiperazin-1-yl) | 466 [M + 1] |
| Ex-206 | benzyl-diazabicyclo | 448 [M + 1] |
| Ex-207 | benzyl-diazabicyclo | 448 [M + 1] |
| Ex-211 | 4-fluorobenzyl-piperazinone | 454 [M + 1] |

The synthesis presented in Scheme E2, above, was repeated using compound 8d (preparative Scheme PI, above) and an appropriate "left-side" precursor in accordance with reaction Scheme E3 to prepare (R)-9-fluoro-2-((4-(4-fluorophenyl)-2-methylpiperazin-1-yl) methyl)-7-methoxy-[1,2,4]triazolo[1,5-c]quinazolin-5-amine (compound Ex-178).

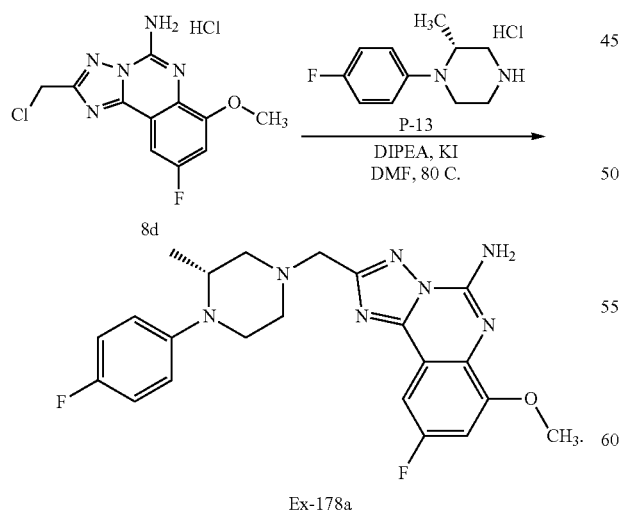

Scheme E3

Ex-178a

Thus, in accordance with Scheme E3, Hunig's Base (0.093 mL, 0.533 mmol) was added to a stirred, room temperature mixture of (R)-1-(4-fluorophenyl)-3-methyl-piperazine (41.4 mg, 0.213 mmol) in DMF (1 mL) and the mixture was stirred at room temperature for 10 min. 2-(chloromethyl)-9-fluoro-7-methoxy-[1, 2, 4]triazolo[1,5-c]quinazolin-5-amine (50 mg, 0.178 mmol) and potassium iodide (1.473 mg, 8.88 μmol) were added thereafter, and the resultant mixture was kept stirring at 80° C. overnight. The mixture was cooled, water (8 mL) was added and the yellow precipitate was collected and washed with water, dried. The yellow solid obtained was further purified by column chromatography on silica gel Teledyne ISCO Si; 24 g prepacked, eluting with $CH_2Cl_2$/MeOH=20:1 to give R)-9-fluoro-2-((4-(4-fluorophenyl)-2-methylpiperazin-1-yl)methyl)-7-methoxy-[1,2,4]triazolo[1,5-c]quinazolin-5-amine (compound Ex-178) as a light yellow solid. LC/MS=422.2 [M+1].

This same synthetic procedure was carried out using an appropriately functionalized "left-side" piperazine precursor to provide compounds of the invention have the structure of Formula E3-A:

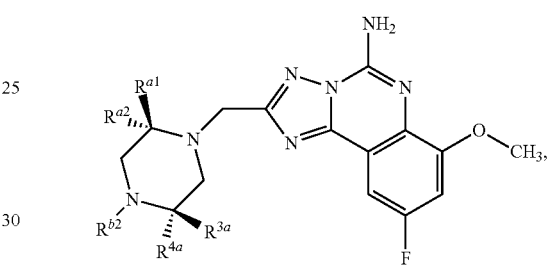

Formula E3-A, wherein $R^{a1}$ to $R^{a4}$ and $R^{b2}$ are each defined in Table VII.

TABLE VII

| Example No. | $R^{a1}/R^{a2}$ | $R^{a3}/R^{a4}$ | $R^{b2}$ | LC/MS [M + 1] |
|---|---|---|---|---|
| Ex-11 | —$CH_3$/—H | —H/—H | 4-F-phenyl | 440.2 |
| Ex-37 | —H/—$CH_3$ | —H/—H | 4-F-phenyl | |
| Ex-41 | —$CH_3$/—H | —H/—H | 5-F-pyridin-2-yl | |
| Ex-42 | —$CH_3$/—H | —H/—H | 5-$CF_3$-pyridin-2-yl | |
| Ex-178a | —H/—H | —$CH_3$/—H | 4-F-phenyl | 422.2 |

The synthesis presented in Scheme E3, above, was repeated using compound 8a and an appropriate "left-side" functionalized piperazine precursor to provide compounds of the invention, for example, compound Ex-170:

Ex-170

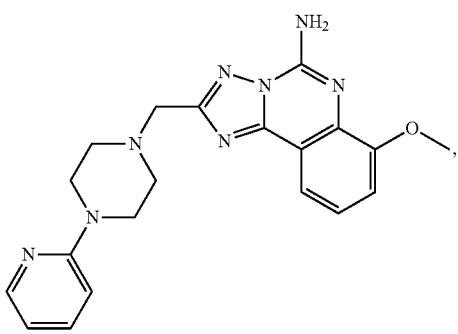

Thus, compound Ex-170 was prepared by combining 2-(chloromethyl)-7-methoxy-[1,2,4]triazolo[1,5-c]quinazolin-5-amine (40 mg, 0.15 mmol) in DMF (2 mL) with DIPEA (39 mg, 0.30 mmol) and mopholine (26 mg, 0.30 mmol). The mixture was stirred at ambient for 48 hours. The product (Ex-170, Table VIII) was purified using Gilson® reverse phase HPLC (acetonitrile (0.1% TFA)/H2O with 0.1% TFA). The compound was characterized by LC/MS [M+1=391].

This same procedure was carried out to provide additional compounds of the invention having the Formula E3-B:

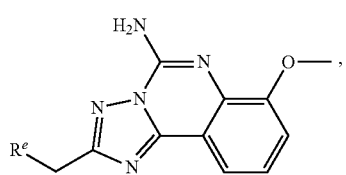

E3-B where $R^e$ is defined in Table VIII.

TABLE VIII

| Example No. | $R^e$ | LC-MS | Retention Time (min) |
|---|---|---|---|
| Ex-170 | | 391 [M + 1] | 1.38 |
| Ex-171 | | 482 [M + 1] | |
| Ex-172 | | 423 [M + 1] | 1.68 |

TABLE VIII-continued

| Example No. | $R^e$ | LC-MS | Retention Time (min) |
|---|---|---|---|
| Ex-173 | | 473 [M + 1] | 1.82 |
| Ex-174 | | 405 [M + 1] | 1.45 |
| Ex-175 | | 458 [M + 1] | 1.97 |
| Ex-176 | | 440 [M + 1] | 1.78 |
| Ex-177 | | 476 [M + 1] | 2.09 |
| Ex-212 | | 390 [M + 1] | 1.77 |

The compounds shown in Table IX were also prepared using the synthesis procedure of E3 and an appropriately substituted piperazine "left-side" precursor.

TABLE IX

| Example No. | Structure | M + 1 | Ret. Time (min) |
|---|---|---|---|
| Ex-1 | (structure) | 422.2 | 1.85 |
| Ex-2 | (structure) | 404.2 | 1.71 |
| Ex-9 | (structure) | 404.2 | 1.497 |
| Ex-10 | (structure) | 422.2 | 1.565 |

The synthesis process presented in Scheme E3, above, was repeated using compound 8b (preparative Example PI, above) and an appropriate piperazine reagent in accordance with Scheme E3ab:

Scheme E3ab

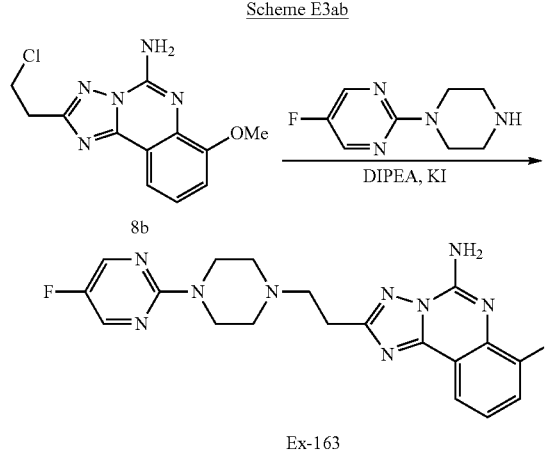

Ex-163

Preparation of 7-methoxy-2-(2-(piperidin-1-yl)ethyl)-[1,2,4]triazolo[1,5-c]quinazolin-5-amine (Ex-163)

Into a vessel was placed 2-(2-chloroethyl)-7-methoxy-[1,2,4]triazolo[1,5-c]quinazolin-5-amine (compound 8b, 150 mg, 0.54 mmol), 5-fluoro-2-(piperazin-1-yl)pyrimidine (92 mg, 1.1 mmol), DIPEA (105 mg, 0.81 mmol) and KI (269 mg, 1.62 mmol) in DMF (50 mL), and the mixture was stirred at 80° C. for 18 h. The mixture was cooled down to RT, diluted with DCM, washed with H₂O (3×), dried and concentrated. Chromatography purification MeOH/DCM (1:30-1:20-1:10) afforded the compound Ex-163, which was characterized using. LC/MS=424 [M+1].

Using a procedure similar to that used in the preparation of compound Ex-163, compounds of the invention having the structure of Formula E3-C were prepared:

E3-C

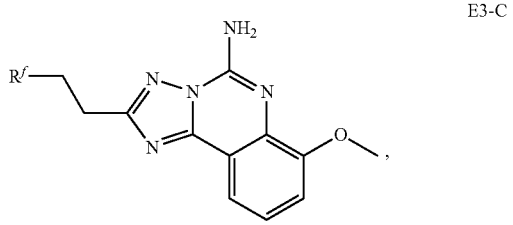

where "R$^e$" is defined in Table X.

TABLE X

| Ex-ample No. | R$^f$ | LC-MS | Retention Time (min) |
|---|---|---|---|
| Ex-163 | ![](pyrimidine-piperazine with F) | 424 [M + 1] | 1.95 |

TABLE X-continued

| Ex-ample No. | R$^f$ | LC-MS | Retention Time (min) |
|---|---|---|---|
| Ex-164 | | 423 [M + 1] | 1.96 |
| Ex-165 | | 405 [M + 1] | 1.81 |
| Ex-166 | | 404 [M + 1] | 1.97 |
| Ex-167 | ![](difluoropyridine-methylpiperazine) | 439 [M + 1] | 1.83 |
| Ex-168 | | 436 [M + 1] | 1.74 |
| Ex-169 | | 437 [M + 1] | 1.66 |

Compound Ex-158 was prepared in accordance with Scheme E3-ac from compound 8c (preparative Example PI, above) and an appropriate piperazine reagent.

Scheme E3-ac

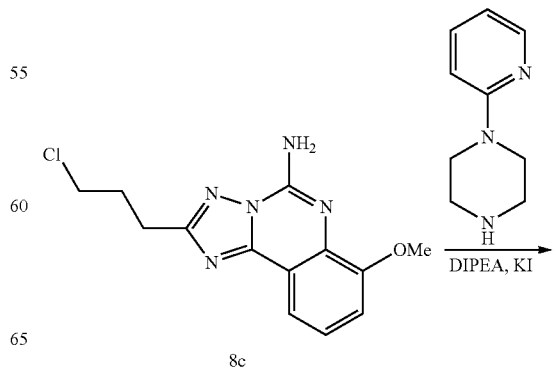

8c

-continued

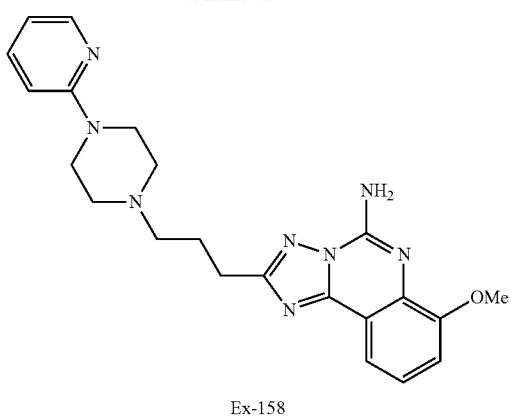

Ex-158

Preparation of 7-methoxy-2-(3-morpholinopropyl)-[1,2,4]triazolo[1,5-c]quinazolin-5-amine Into a vessel was placed 2-(3-chloropropyl)-7-methoxy-[1,2,4]triazolo[1,5-c]quinazolin-5-amine (compound 8c, 80 mg, 0.286 mmol), 1-(pyridin-2-yl)piperazine (75 mg, 0.86 mmol), and KI (142 mg, 0.858 mmol) in DMF (2 mL). The mixture was stirred at 80° C. for 18 h. The mixture was cooled down to RT, diluted with DCM, washed with H$_2$O (3×), dried and concentrated. Chromatography purification MeOH/DCM (1:30-1:20-1:10) afforded compound Ex-158, which was characterized by LC/MS=419 [M+1].

Using the procedure shown in Scheme E3-ac and an appropriate piperazine derivative, the compounds of Formula E3-D were prepared:

E3-D

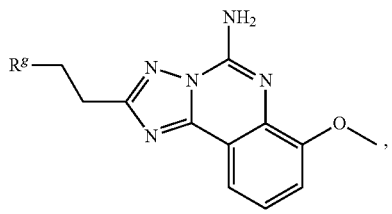

where "R$^g$" is defined in Table XI.

TABLE XI

| Example No. | Structure | LC-MS | Retention Time (min) |
|---|---|---|---|
| Ex-158 | 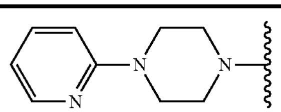 | 419 [M + 1] | 1.77 |
| Ex-159 | 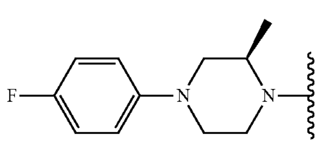 [SMILES: *N1CCN(c2ccc(F)cc2)C[C@H]1C] | 450 [M + 1] | 1.73 |

Example 3: Preparation of Compounds of the Invention Via DIPEA-Mediated Coupling of a Piperazine "Left-Side" Precursor and Triazolo "Right-Side" Precursor Additional compounds of the invention were prepared in accordance with general preparative scheme AI from triazole "right-side" precursor 8F (prep scheme PII) and an appropriate piperazine reagent in accordance with Scheme E3-ac:

Scheme E3-ac

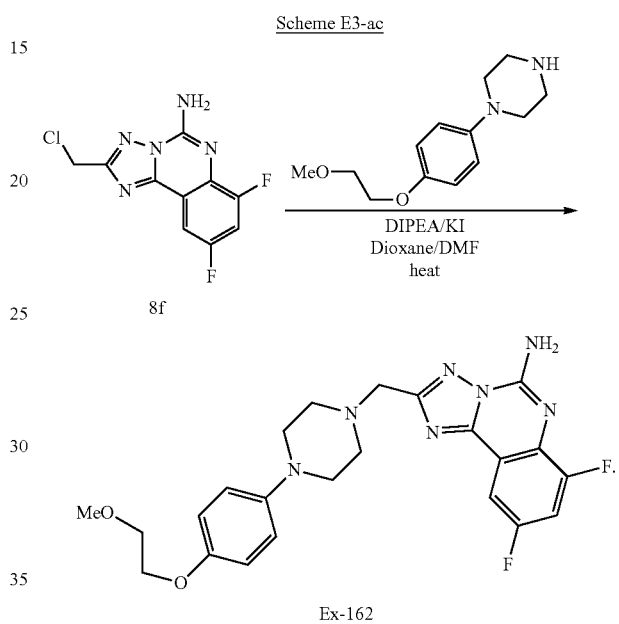

Ex-162

Using this same procedure, compounds of Formula E3-E were prepared:

Formula E3-E

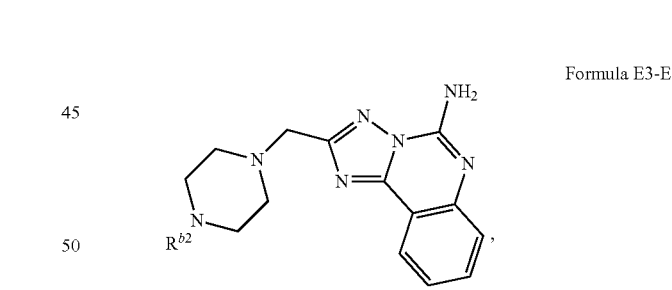

wherein R$^{b2}$ is defined in Table XII.

TABLE XII

| Example No. | R$^{2b}$ | Retention time (min) LC-MS [M + 1]. |
|---|---|---|
| Ex-160 | | 1.46<br>433 |

TABLE XII-continued

| Example No. | R[2b] | Retention time (min) LC-MS [M + 1]. |
|---|---|---|
| Ex-161 | 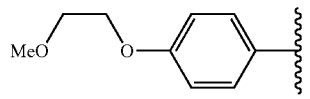 | 1.41 434 |

Example 4: Preparation of Cycloamine-Triazole Piperazine Compounds Using Palladium Catalyst in Accordance with Scheme AIII from DMB-Protected "Right-Side" Piperazine-Substituted Precursor (Ex-E4-Pre) and Appropriately-Substituted Aryl Bromide Using the process described in Scheme E3, the compound Ex-E4-pre was prepared from Compound 8a-Protected (see general prep Scheme AIII (preparation of cmpd 15) and Scheme BId) and an appropriate acyl-protected piperazine precursor as shown in Scheme E4.

Scheme E4

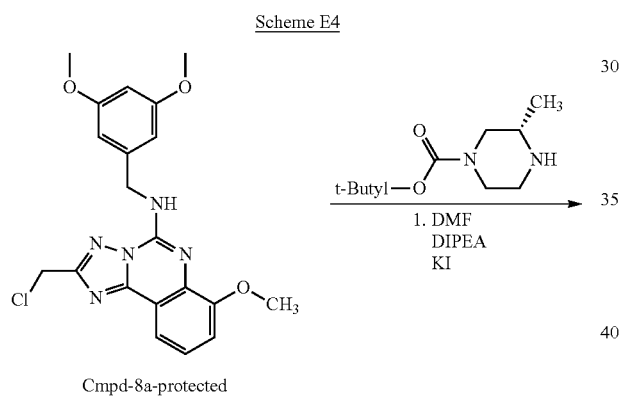

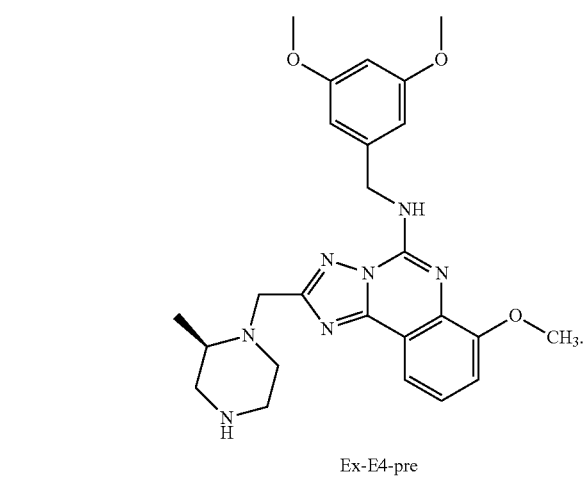

Ex-E4-pre

The compound Ex-55 was prepared from Compound Ex-E4-pre and an appropriately substituted aromatic reagent Scheme E4-ab.

Scheme E4-ab

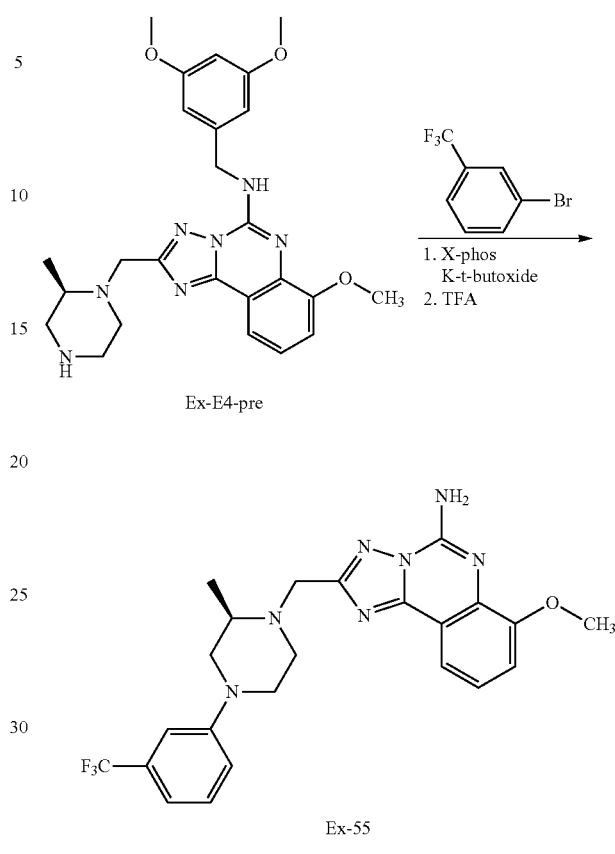

Ex-55

Accordingly, into a vessel containing the compound of Formula Ex-E4-pre previously prepared ([(R)—N-(3,5-dimethoxybenzyl)-7-methoxy-2-((2-methylpiperazin-1-yl)methyl)-[1,2,4]triazolo[1,5-c]quinazolin-5-amine], 30 mg, 0.063 mmol) dissolved in THF (628 uL), was added Chloro (2-dicyclohexylphosphino-2',6'-di-i-propoxy-1,1'-biphenyl) [2-(2-aminoethylphenyl)]-palladium(II) (X-Phos, 9 mg, 0.013 mmol), 3-bromobenzotrifluoride (27.46, 0.0123 mmol) and finally potassium tert-butoxide (22 mg, 0.188 mmol). The reaction mixture was heated at 100° C. for 15 h then cooled to ambient temperature of 21° C. 10% w/v citric acid (1000 uL) was added followed by dichloromethane (2×1000 uL). The organic layers were separated and then concentrated in vacuo via a Genevac. The residue thus collected was then dissolved in trifluoroacetic acid (300 uL, 3.89 mmol) and heated to 40 C for 4 h and then allowed to stir at 21° C. for 8 hours. The reaction was then diluted with DMSO (1000 uL) and was purified by reverse phase semi prep HPLC Waters XBridge (CH$_3$CN/H$_2$O/NH$_4$OH, C18, 5 u, 19×100 mm system) to yield compound Ex-55 as a solid, which was characterized using LC/MS=472 [M+1].

Compounds of the invention having the structure of Formula E4-A were prepared by using this same method by reacting an appropriate aryl moiety with the compound of Formula Ex-E4-pre in accordance with Scheme E4-ab:

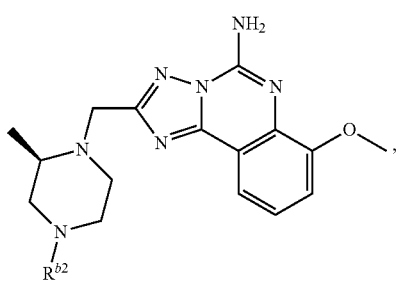

Formula E4-A, wherein $R^{b2}$ is defined in Table XIII, below.

TABLE XIII

| Example No. | $R^{b2}$ | [M + 1] | Retention Time |
|---|---|---|---|
| EX-55 | 3-CF3-phenyl | 472 | 1.07 |
| EX-56 | 2-F-phenyl | 422 | 0.95 |
| EX-57 | 3-F-phenyl | 422 | 0.96 |
| EX-58 | 2-Cl-phenyl | 438 | 1.02 |
| EX-59 | 2-CN-phenyl | 429 | 0.89 |
| EX-60 | 3-CN-phenyl | 429 | 0.89 |
| EX-61 | 4-CN-phenyl | 429 | 0.87 |
| EX-62 | pyrimidin-2-yl | 406 | 0.75 |

TABLE XIII-continued

| Example No. | $R^{b2}$ | [M + 1] | Retention Time |
|---|---|---|---|
| EX-63 | quinolin-6-yl | 455 | 0.81 |
| EX-64 | 2-methylphenyl | 418 | 1.04 |
| EX-65 | 3-methylphenyl | 418 | 0.99 |
| EX-66 | 4-methylphenyl | 418 | 0.98 |
| EX-67 | 2-methoxyphenyl | 434 | 0.90 |
| EX-68 | 3-methoxyphenyl | 434 | 0.91 |
| EX-69 | pyridin-3-yl | 405 | 0.71 |
| EX-70 | pyridin-4-yl | 405 | 0.70 |
| EX-71 | naphthalen-1-yl | 454 | 1.10 |
| EX-72 | naphthalen-2-yl | 454 | 1.07 |

TABLE XIII-continued

| Example No. | $R^{b2}$ | [M + 1] | Retention Time |
|---|---|---|---|
| EX-73 | 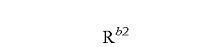 | 434 | 0.87 |

Example 5: Compounds of the Invention Prepared According to General Scheme AIII to Provide Compounds of Structure 16a in Accordance with Synthesis Scheme E5

"Right-side" precursors having substituents in the $R^{E5a}$ position as defined in Table XIV (below) were employed to prepare piperidine-substituted compounds of the invention using the synthesis procedure described in general scheme AIII, as shown in Scheme E5.

Scheme E5

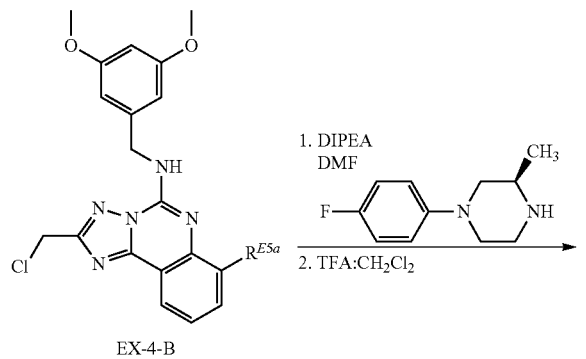

EX-4-B

EX-4-C

Accordingly, the compound Ex-4-B—CN (compound Ex-4-B where substituent $R^{E5a}$ is —CN), (110 mg; 0.27 mmol), 1-(4-fluorophenyl)-3(R)-methyl piperazine hydrochloride (85 mg; 0.37 mmol) and Hunig's base (0.14 mL; 104 mg; 0.807 mmol) in anhydrous DMF (1 mL) was stirred and heated at 80° C. for 18 hr. The reaction mixture was cooled to RT, diluted with water and extracted with EtOAc. The organic extract was washed with water and brine. Combined aqueous layers were back extracted with $CH_2Cl_2$. Both organic extracts were combined, dried over solid anhydrous $Na_2SO_4$ and concentrated to yield a beige solid. The crude product was purified by preparative TLC (5% $CH_3OH$—$CH_2Cl_2$) and the major fluorescent band that was the 2,4-dimethoxybenzyl protected form of Ex-4-C-CN (Ex-4-C wherein substituent $R^{E5a}$ is —CN) was isolated as an off-white solid that was characterized by LC/MS=567 ($MH^+$).

The isolated product from the previous step was dissolved in $CH_2Cl_2$:TFA (1 mL each) and stirred at 57° C. for 4 hr. The clear reaction mixture had become deep purple and MS showed complete deprotection of the DMB group to give the desired product. The solvents were removed on a rotary evaporator and the residual TFA was removed by azeotrope formation with toluene to give a yellow sticky semi-solid. This material was treated with 7% $NH_3$ in methanol, stirred for 10 minutes and concentrated to obtain a beige solid. The crude product was purified by preparative TLC ($CH_2Cl_2$ with 7% $NH_3$ in methanol, 96:4) to afford compound Ex-156, an off-white solid characterized using LC/MS: 417 ($MH^+$); $R_t$=2.02.

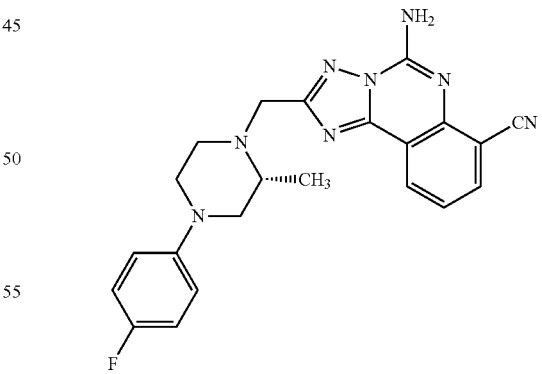

Ex-156

Compound Ex-157 (Ex-4-C, wherein —$R^{Ex5a}$ is —Br) and Compound Ex-155 (compound Ex-4-C, wherein $R^{Ex5a}$ is —$CF_3$) were prepared using the procedure of Scheme E5, and are listed in Table XIV with their corresponding characterization data.

TABLE XIV

| Example No. | Structure | M + 1 (R_t) |
|---|---|---|
| EX-157 | 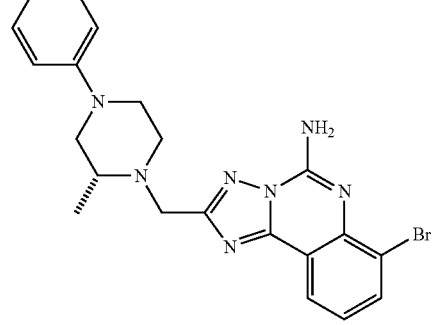 | 470 (2.13) |
| Ex-156 | 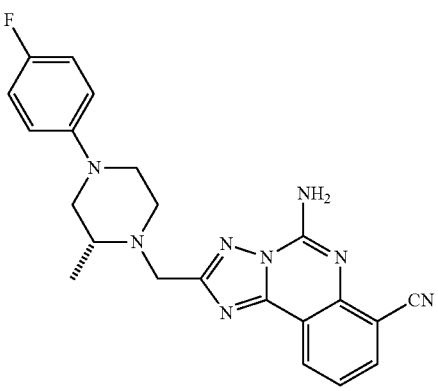 [SMILES: C[C@@H]1CN(c2ccc(F)cc2)CCN1Cc1nc2c3cccc(C#N)c3nc(N)n2n1] | 417 (2.02) |
| EX-155 | 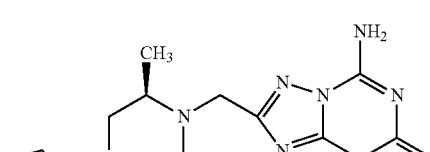 | 460 (1.93) |

Example 6: Preparation of [1,2,4]triazolo[1,5-c]quinazolin-2-yl)-1-(4substituted-piperazin-1-yl)ethanone compounds from 2-(5-amino-7-methoxy-[1,2,4]triazolo[1,5-c]quinazolin-2-yl)acetic acid "right-side" precursor and an appropriately-substituted piperazine reagent Scheme E11

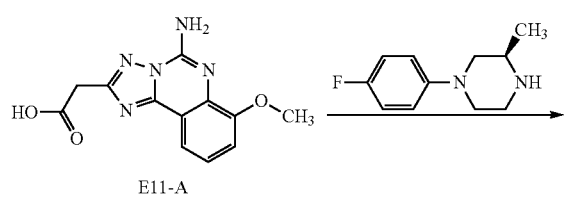

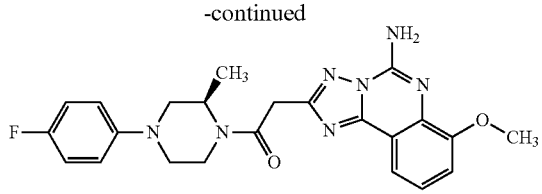

Ex-154

To a stirred suspension of E11-A (0.025 g, 0.081 mmol) followed by Dichloromethane (5 ml), 4-fluorophenylpiperazine (0.031 g, 0.161 mmol), DIPEA (0.070 ml, 0.404 mmol), and 1-propanephosphonic acid cyclic anhydride (0.096 ml, 0.161 mmol). The reaction was stirred room temperature overnight.

The reaction mixture was concentrated, diluted with water (~0.5 mL) and then dissolved in DMSO (~4 mL).

The residue was purified by preparative HPLC (Reverse phase C-18, Phenomenex Gemini, Axia 150×21.2 mm, 5 u), eluting with 10-95% Acetonitrile/Water+0.1% TFA (20 mL/min) over 10 min. to give the product as a TFA salt. LCMS M+H=450

Using a similar procedure, the compound of Formula Ex-153 was also prepared from a suitably substituted piperazine "left-side" precursor and the compound of Formula P23 (see Scheme AII):

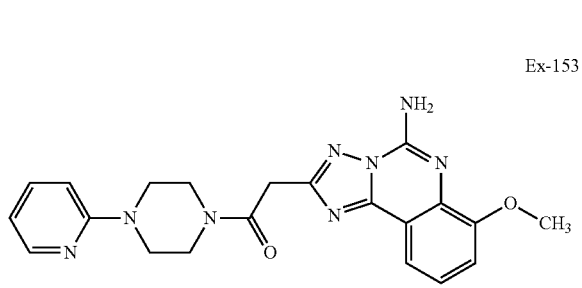 [SMILES: COc1cccc2c1nc(N)n1nc(CC(=O)N3CCN(c4ccccn4)CC3)nc21]

Ex-153

The compound of Formula Ex-153 was characterized by LC/MS (Rt 0.51, Meth B, [M+1]=419]

Example 7: Preparation of Compound of the Invention Ex-50 from "Right-Side" Precursor of Formula 13a

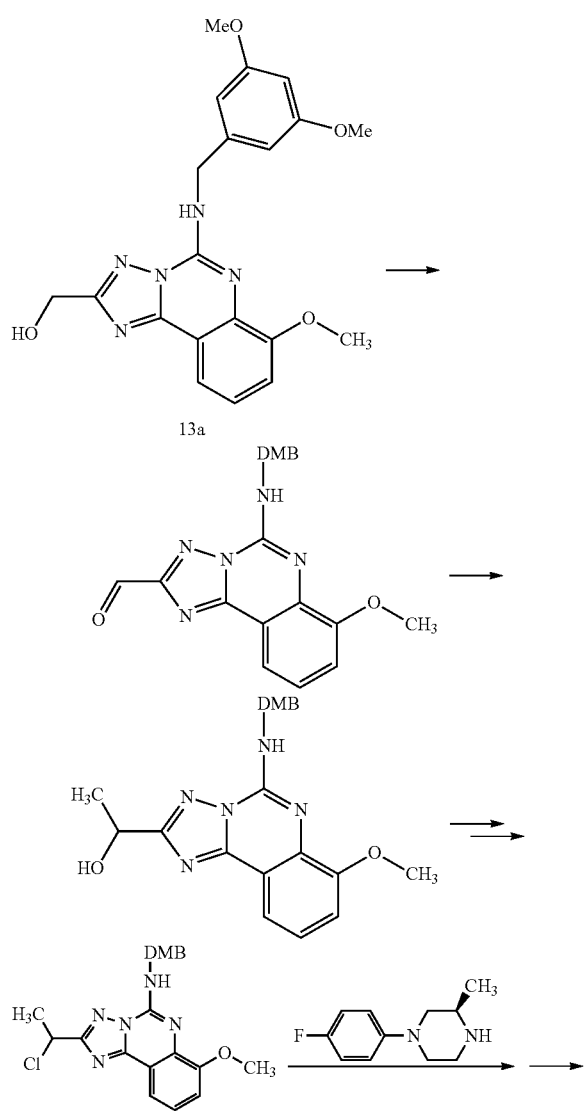

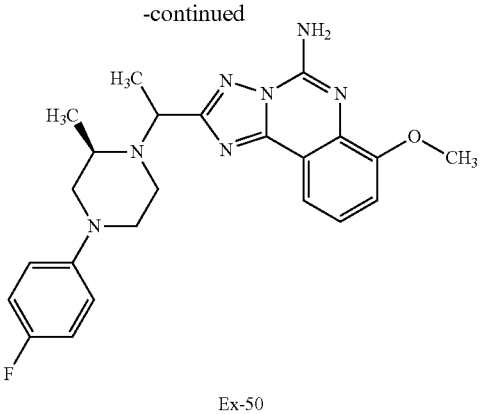

Ex-50

Step A: 5-[(2,4-dimethoxybenzyl)amino]-7-methoxy [1,2,4]triazolo[1,5-c]quinazoline-2-carbaldehyde To a dichloromethane (50 mL) solution of {5-[(2,4-dimethoxybenzyl)amino]-7-methoxy[1,2,4]triazolo[1,5-c]quinazolin-2-yl}methanol (compound 13a prepared in accordance with general preparative procedure PII, above, 1,000 mg, 2.53 mmol) was added 1,1,1-tris(acetyloxy)-1,1-dihydro-1,2-benziodoxl-3-(1H)-one (1,126 mg, 2.66 mmol). The reaction mixture was stirred at room temperature for 30 minutes, washed with saturated sodium bicarbonate solution and then with brine, dried (magnesium sulfate), filtered, and concentrated in vacuo. Chromatography over silica gel, eluting with hexanes/ethyl acetate, afforded the title compound as a white solid. $^1$H NMR (500 MHz, DMSO-d$_6$) δ 10.19 (s, 1H), 8.59 (t, J=5.8 Hz, 1H), 7.84 (dd, J=7.9, 1.3 Hz, 1H), 7.37 (t, J=7.9 Hz, 1H), 7.30 (dd, J=8.0, 1.3 Hz, 1H), 7.26 (d, J=8.4 Hz, 1H), 6.57 (d, J=2.4 Hz, 1H), 6.42 (dd, J=8.4, 2.4 Hz, 1H), 4.70 (d, J=5.7 Hz, 2H), 3.90 (s, 3H), 3.84 (s, 311), 3.71 (s, 3H); LC-MS: m/z 394.1 (M+H).

Step B: (±)-1-{5[(2,4-dimethoxybenzyl)amino]-7-methoxy[1,2,4]triazolo[1,5-c]quinazolin-2-yl}ethanol To a tetrahydrofuran (10 mL) solution of 5-[(2,4-dimethoxybenzyl)amino]-7-methoxy[1,2,4]triazolo[1,5-c]quinazoline-2-carbaldehyde (537 mg, 1.37 mmol) at 0° C. was added 3.0 M tetrahydrofuran solution of methylmagnesium chloride (1.0 mL, 3.0 mmol). The reaction mixture was stirred in an ice-bath for 45 minutes and then at room temperature for 1.5 hours. It was quenched with saturated ammonium chloride solution and extracted with ethyl acetate (3×50 mL). The combined organic layers were washed with brine and concentrated in vacuo to afford the crude solid. It was recrystallized from ethyl acetate/hexanes to afford the title compound as an off-white solid. $^1$H NMR (500 MHz, DMSO-d$_6$) δ 8.09 (t, J=6.1 Hz, 1H), 7.76 (d, J=8.0 Hz, 1H), 7.30 (t, J=7.7 Hz, 1H), 7.26-7.20 (m, 2H), 6.57 (d, J=2.3 Hz, 1H), 6.43 (dd, J=8.3, 2.5 Hz, 1H), 5.58 (d, J=5.1 Hz, 1H), 4.99 (quintet, J=6.1 Hz, 1H), 4.68 (d, J=5.9 Hz, 2H), 3.89 (s, 3H), 3.84 (s, 3H), 3.71 (s, 3H), 1.55 (d, J=6.6 Hz, 3H); LC-MS: m/z 410.1 (M+H).

Step C: (±)-1-{5-[(2,4-dimethoxybenzyl)amino]-7-methoxy[1,2,4]triazolo[1,5-c]quinazolin-2-yl}ethyl methanesulfonate To a dichloromethane (20 mL) solution of (±)-1-{-[4(2,4-dimethoxybenzyl)amino]-7-methoxy[1,2,4]triazolo[1,5- c]quinazolin-2-yl}ethanol (437 ing, 0.865 mmol) and diisopropylethylamine (0.75 mL, 4.3 mmol) was added methanesulfonyl chloride (0.25 mL, 3.2 mmol). The reaction mixture was stirred for 15 minutes at room temperature. It was washed with water and with brine, dried (magnesium sulfate), and concentrated in vacuo. Chromatography over silica gel, eluting with hexanes/ethyl acetate, afforded the title compound as a white solid. $^1$H NMR (500 MHz, DMSO-$d_6$) δ 8.24 (t, J=6.0 Hz, 1H), 7.78 (d, J=7.9 Hz, 1H), 7.39-7.26 (m, 1H), 7.25 (d, J=8.3 Hz, 2H), 6.57 (d, J=2.4 Hz, 1H), 6.43 (dd, J=8.2, 2.6 Hz, 1H), 6.01 (q, J=6.6 Hz, 1H), 4.69 (d, J=6.2 Hz, 2H), 3.89 (s, 3H), 3.84 (s, 3H), 3.71 (s, 3H), 3.27 (s, 3H), 1.83 (d, J=6.6 Hz, 3H); LC-MS: m/z 488.0 (M+H).

Step D: (±)-2-(1-chloroethyl)-N-(2,4-dimethoxybenzyl)-7-methoxy[1,2,4]triazolo[1,5-c]quinazolin-5-amine To an acetone (15 mL) solution of (±)-1-{5-[(2,4-dimethoxybenzyl)amino]-7-methoxy[1,2,4]triazolo[1,5-c]quinazolin-2-yl}ethyl methanesulfonate (340 mg, 0.697 mmol) was added lithium chloride (150 mg, 3.54 mmol). The reaction mixture was refluxed for 24 hours and concentrated in vacuo. It was dissolved in dichloromethane (50 mL), washed with saturated sodium bicarbonate solution, dried (magnesium sulfate), and concentrated in vacuo to afford the title compound as a crude solid. It was used in the subsequent reaction without further purification. $^1$H NMR (500 MHz, DMSO-$d_6$) δ 8.21 (t, J=6.0 Hz, 1H), 7.78 (dd, J=7.9, 1.3 Hz, 1H), 7.32 (t, J=8.0 Hz, 1H), 7.27-7.23 (m, 2H), 6.57 (d, J=2.3 Hz, 1H), 6.43 (dd, J=8.3, 2.5 Hz, 1H), 5.57 (q, J=6.8 Hz, 1H), 4.68 (dd, J=6.3, 2.5 Hz, 2H), 3.89 (s, 3H), 3.84 (s, 3H), 3.71 (s, 3H), 1.98 (d, J=6.7 Hz, 3H); LC-MS: m/z 428.0 (M+H).

Step E: N-(2,4-dimethoxybenzyl)-2-{1-[(2R)-4-(4-fluorophenyl)-2-methylpiperazin-1-yl]ethyl}-7-methoxy[1,2,4]triazolo[1,5-c]quinazolin-5-amine To a N,N-dimethylformamide (5 mL) solution of (3R)-1-(4-fluorophenyl)-3-methylpiperazine (158 mg, 0.813 mmol) and (±)-2-(1-chloroethyl)-N-(2,4-dimethoxybenzyl)-7-methoxy[1,2,4]triazolo[1,5-c]quinazolin-5-amine (300 ing, 0.701 mmol) was added potassium iodide (148 mg, 0.892 mmol) and diisopropylethylamine (0.30 mL, 1.7 mmol). The reaction mixture was heated to 80° C. for 18 hours. It was cooled to room temperature and diluted with saturated ammonium chloride solution. It was extracted with ethyl acetate (3×25 mL), and the combined organic layers were washed with water and with brine, dried (magnesium sulfate), and concentrated in vacuo. Chromatography over silica gel, eluting with hexanes/ethyl acetate, afforded the title compound as two separated diastereomers.

Less polar diastereomer $^1$H NMR (500 MHz, DMSO-$d_6$) δ 8.11 (t, J=6.0 Hz, 1H), 7.78 (d, J=7.9 Hz, 1H), 7.30 (t, J=7.9 Hz, 1H), 7.28-7.19 (m, 2H), 7.00 (t, J=8.7 Hz, 2H), 6.91-6.86 (m, 2H), 6.57 (d, J=2.3 Hz, 1H), 6.44 (dd, J=8.4, 2.3 Hz, 1H), 4.69 (d, J=6.0 Hz, 2H), 4.55 (q, J=6.9 Hz, 1H), 3.89 (s, 3H), 3.84 (s, 3H), 3.71 (s, 3H), 3.40 (d, J=11.2 Hz, 1H), 3.24 (d, J=10.6 Hz, 1H), 2.99-2.84 (m, 1H), 2.89-2.83 (m, 1H), 2.67-2.51 (m, 3H), 1.44 (d, J=6.8 Hz, 3H), 1.20 (d, J=6.2 Hz, 3H); LC-MS: m/z 586.1 (M+H).

More polar diastereomer $^1$H NMR (500 MHz, DMSO-$d_6$) δ 7.98 (t, J=6.1 Hz, 1H), 7.77 (dd, J=7.9, 1.3 Hz, 1H), 7.30 (t, J=7.9 Hz, 1H), 7.26 (d, J=8.4 Hz, 1H), 7.23 (dd, J=8.0, 1.4 Hz, 1H), 7.02-6.94 (m, 2H), 6.89-6.84 (m, 2H), 6.58 (d, J=2.4 Hz, 1H), 6.45 (dd, J=8.4, 2.4 Hz, 1H), 4.75-4.64 (m, 2H), 4.64-4.57 (m, 1H), 3.89 (s, 3H), 3.84 (s, 3H), 3.71 (s, 3H), 3.45 (d, J=11.3 Hz, 1H), 3.38 (d, J=11.5 Hz, 1H), 3.13 (dt, J=11.7, 2.9 Hz, 1H), 2.63 (td, J=11.1, 2.9 Hz, 1H), 2.59-2.48 (m, 1H), 2.41 (td, J=11.4, 2.9 Hz, 1H), 2.36 (t, J=10.6 Hz, 1H), 1.58 (d, J=7.0 Hz, 3H), 1.29 (d, J=6.1 Hz, 3H); LC-MS: m/z 586.1 (M+H).

Step F: 2-{1-[(2R)-4-(4-fluorophenyl)-2-methylpiperazin-1-yl]ethyl}-7-methoxy[1,2,4]triazolo[1,5-c]quinazolin-5-amine The less polar diastereomer of N-(2,4-dimethoxybenzyl)-2-{1-[(2R)-4-(4-fluorophenyl)-2-methylpiperazin-1-yl]ethyl}-7-methoxy[1,2,4]triazolo[1,5-c]quinazolin-5-amine (78 mg, 0.133 mmol) was charged with trifluoroacetic acid (2 mL) and heated at 50° C. for 3 hours. The reaction mixture was concentrated in vacuo and charged with a 2.0 M methanolic solution of ammonia (4 mL), precipitating one diasteromer of the title compound as a white solid. $^1$H NMR (500 MHz, DMSO-$d_6$) δ 7.79 (s, 2H), 7.76 (d, J=8.1 Hz, 1H), 7.29 (t, J=7.9 Hz, 1H), 7.21 (d, J=7.9 Hz, 1H), 7.00 (t, J=8.7 Hz, 2H), 6.89 (dd, J=8.9, 4.7 Hz, 2H), 4.53 (q, J=6.9 Hz, 1H), 3.89 (s, 3H), 3.39 (d, J=11.3 Hz, 1H), 3.24 (d, J=11.8 Hz, 1H), 2.94-2.89 (m, 1H), 2.89-2.83 (m, 1H), 2.66-2.53 (m, 3H), 1.43 (d, J=6.8 Hz, 3H), 1.20 (d, J=6.2 Hz, 3H); LC-MS: m/z 436.0 (M+H).

The more polar diastereomer of N-(2,4-dimethoxybenzyl)-2-{1-[(2R)-4-(4-fluorophenyl)-2-methylpiperazin-1-yl]ethyl}-7-methoxy[1,2,4]triazolo[1,5-c]quinazolin-5-amine (100 mg, 0.171 mmol) was charged with trifluoroacetic acid (2 mL) and heated at 50° C. for 3 hours. The reaction mixture was concentrated in vacuo and charged with a 2.0 M methanolic solution of ammonia (4 mL). The reaction mixture was concentrated in vacuo to afford a crude solid. Chromatography over silica gel, eluting with hexanes/ethyl acetate, afforded the other diasteromer of the title compound. $^1$H NMR (500 MHz, DMSO-$d_6$) δ 7.77 (s, 2H), 7.74 (dd, J=8.0, 1.2 Hz, 1H), 7.29 (t, J=8.0 Hz, 1H), 7.21 (d, J=7.9 Hz, 1H), 6.98 (t, J=8.7 Hz, 2H), 6.86 (dd, J=8.9, 4.7 Hz, 2H), 4.59 (q, J=7.1 Hz, 1H), 3.89 (s, 3H), 3.45 (d, J=11.1 Hz, 1H), 3.37 (d, J=11.4 Hz, 1H), 3.13 (d, J=11.5 Hz, 1H), 2.63 (td, J=11.1, 2.8 Hz, 1H), 2.55-2.46 (m, 1H), 2.42 (td, J=11.4, 2.9 Hz, 1H), 2.35 (t, J=10.6 Hz, 1H), 1.57 (d, J=7.0 Hz, 3H), 1.28 (d, J=6.1 Hz, 3H); LC-MS: m/z 436.0 (M+H).

It will be appreciated that by applying the foregoing methods, all of the compounds presented in Tables can be prepared.

A2a Activity of Compounds of the Invention

Binding affinities of compounds of the invention for the human A2a receptor were determined in a competition binding assay using Scintillation Proximity technology. Thus, 0.3 ug of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo-[1,5-c]pyrimidine (the tritiated compound) and 100 ug of wheatgerin agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination:

Materials
- HEK293 cells expressing the human, rat, dog or monkey adenosine 2a receptor (Purchased from Perkin-Elmer # RBHA2AM400UA).
- The Tritiated compound was prepared in-house by MRL Radiochemistry according to published methods.
- Wheatgerm agglutinin-coated yttrium silicate SPA beads (GE Healthcare #RPNQ0023). Dilute to 25 mg/ml in assay buffer.
- Assay Buffer was prepared in house: Dulbecco's calcium and magnesium free phosphate buffered saline+10 mM MgCl$_2$
- Adenosine deaminase from calf intestine, 10 mg/2 ml (Roche #10 102 105 001).
- DMSO
- A2a antagonist standard (9-chloro-1-(2-furanyl)-[1,2,4]triazolo1,5-c]quinazolin-5-amine from Tocris Bioscience)

Compound Dilution
- Make eight 1:3 serial dilutions in 100% DMSO from a 3 mM compound stock
- Transfer 50 nl of compound into a 384-well OptiPlate (Perkin Elmer).
- Typically, final concentrations of compound used in the assay ranged from 3000 nM to 0.152 nM.

Radioisotope
- Dilute a solution of the Tritiated compound to 1.25 nM in assay buffer. This is a 2.5× solution. The final concentration in the assay is 0.5 nM. Calculate the concentration by counting two 5 ul aliquots.

Membrane Preparation
- Use 0.25 ug of membrane/well. Dilute membranes to 9.7 ug/ml in assay buffer. Treat with 20 ug/ml adenosine deaminase (ADA) for 15 minutes at room temperature to degrade endogenous adenosine.

Membrane-Bead Mixture
- Use 100 ug/well wheatgerm agglutinin-coated yttrium silicate SPA beads.
- Mix ADA-treated membranes and SPA beads together for 30 min prior to assay.

Assay Assembly
- To the Perkin-Elmer Optiplate-384 containing the compound titration add 20 ul of 2.5× solution of the Tritiated compound and 30 ul of the membrane-bead mixture. Incubate for one hour at room temperature with agitation.
- Include total binding (assay buffer+1% DMSO) and non-specific binding (CGS15943, 1 uM) wells.

Counting
- Allow the beads to settle for one hour.
- Count in TopCount.

Calculations
- A curve fitting program (i.e., Prism, Activity Base, Chemcart) is used to determine the EC50.
- The Ki value is calculated using the Cheng-Prusoff equation.

$$Ki=EC50/(1+(\text{radioligand concentration}/Kd))$$

Using the foregoing assay method, the following results were obtained using various of the compounds of the invention described herein. Each example compound tested is reported in the following format: Example number: A2a EC50 reported in nM. Thus, for example, the compound Ex-1 was determined to have an EC50 using the above-described assay, of 4.251 nM, and is accordingly reported as "Ex-1: A2a=4.251":

Ex-1: A2a=4.251; Ex-2: A2a=10.1; Ex-3: A2a=189.7; Ex-4: A2a=43.54; Ex-5: A2a=6.785; Ex-6: A2a=4.023; Ex-7: A2a=20.91; Ex-8: A2a=21.25; Ex-9: A2a=44; Ex-10: A2a=54.67; Ex-11: A2a=7.682; Ex-12: A2a=87.95; Ex-13: A2a=87.1; Ex-14: A2a=52.77; Ex-15: A2a=8.097; Ex-16: A2a=36.51; Ex-17: A2a=26.7; Ex-18: A2a=26.9; Ex-19: A2a=29.6; Ex-20: A2a=51.7; Ex-21: A2a=20.3; Ex-22: A2a=10; Ex-23: A2a=17.7; Ex-24: A2a=14.4; Ex-25: A2a=34.5; Ex-26: A2a=21.8; Ex-27: A2a=6.8; Ex-28: A2a=15.6; Ex-29: A2a=18.6; Ex-30: A2a=9.2; Ex-31: A2a=49.1; Ex-32: A2a=78.3; Ex-33: A2a=35.9; Ex-34: A2a=18.5; Ex-35: A2a=3.7; Ex-36: A2a=18.1; Ex-37: A2a=48.9; Ex-38: A2a=37.5; Ex-39: A2a=13.3; Ex-40: A2a=22.6; Ex-41: A2a=18.1; Ex-42: A2a=28.3; Ex-43: A2a=2.108; Ex-44: A2a=3.6; Ex-45: A2a=5.7; Ex-46: A2a=50.2; Ex-47: A2a=59.2; Ex-48: A2a=18.2; Ex-49: A2a=4.9; Ex-50: A2a=139.4; Ex-51: A2a=73.8; Ex-52: A2a=48.5; Ex-53: A2a=15.93; Ex-54: A2a=106; Ex-55: A2a=5.2; Ex-56: A2a=8.5; Ex-57: A2a=4.178; Ex-58: A2a=12.4; Ex-59: A2a=30.9; Ex-60: A2a=18.8; Ex-61: A2a=11.4; Ex-62: A2a=26.5; Ex-63: A2a=1.444; Ex-64: A2a=13.1; Ex-65: A2a=7.0; Ex-66: A2a=3.0; Ex-67: A2a=8.9; Ex-68: A2a=7.71; Ex-69: A2a=39.8; Ex-70: A2a=92.8; Ex-71: A2a=11.5; Ex-72: A2a=6.7; Ex-73: A2a=2.1; Ex-74: A2a=31.82; Ex-75: A2a=47.4; Ex-76: A2a=13.48; Ex-77: A2a=9.691; Ex-78: A2a=4.537; Ex-79: A2a=21.12; Ex-80: A2a=19.37; Ex-81: A2a=68.2; Ex-82: A2a=627.6; Ex-83: A2a=47.65; Ex-84: A2a=57.21; Ex-85: A2a=7.682; Ex-86: A2a=3.325; Ex-87: A2a=21.47; Ex-88: A2a=22.16; Ex-89: A2a=72.24; Ex-90: A2a=53.5; Ex-91: A2a=42.25; Ex-92: A2a=5.2; Ex-93: A2a=4.6; Ex-94: A2a=1.848; Ex-95: A2a=3.098; Ex-96: A2a=3.411; Ex-97: A2a=18.18; Ex-98: A2a=39.66; Ex-99: A2a=46.29; Ex-100: A2a=29.4; Ex-101: A2a=4.954; Ex-102: A2a=2.14; Ex-103: A2a=5.559; Ex-104: A2a=23.13; Ex-105: A2a=16.79; Ex-106: A2a=4.728; Ex-107: A2a=6.98; Ex-108: A2a=5.268; Ex-109: A2a=4.664; Ex-110: A2a=1.105; Ex-111: A2a=0.9182; Ex-112: A2a=1.597; Ex-113: A2a=27.30; Ex-114: A2a=12.25; Ex-115: A2a=1.388; Ex-116: A2a=3.033; Ex-117: A2a=12.7; Ex-118: A2a=1.246; Ex-119: A2a=1.974; Ex-120: A2a=20.75; Ex-121: A2a=13.24; Ex-122: A2a=4.858; Ex-123: A2a=4.248; Ex-124: A2a=2.824; Ex-125: A2a=1.026; Ex-126: A2a=2.393; Ex-127: A2a=3.076; Ex-128: A2a=0.964; Ex-129: A2a=11.58; Ex-130: A2a=0.8983; Ex-131: A2a=0.6984; Ex-132: A2a=2.041; Ex-133: A2a=1.684; Ex-134: A2a=4.566; Ex-135: A2a=10.7; Ex-136: A2a=11.42; Ex-137: A2a=20.57; Ex-138: A2a=14.28; Ex-139: A2a=81.77; Ex-140: A2a=4.929; Ex-141: A2a=2.339; Ex-142: A2a=16.49; Ex-143: A2a=13.89; Ex-144: A2a=20.12; Ex-145: A2a=18.37; Ex-146: A2a=6.348; Ex-147: A2a=6.6; Ex-148: A2a=18; Ex-149: A2a=13.42; Ex-150: A2a=15.02; Ex-151: A2a=2.217; Ex-152: A2a=2.2; Ex-153: A2a=7.3; Ex-154: A2a=2.6; Ex-155: A2a=136.4; Ex-156: A2a=740; Ex-157: A2a=14.4; Ex-158: A2a=7.1; Ex-159: A2a=24.4; Ex-160: A2a=343.4; Ex-161: A2a=524.9; Ex-162: A2a=74.2; Ex-163: A2a=7.8; Ex-164: A2a=2.5; Ex-165: A2a=3.3; Ex-166: A2a=13.5; Ex-167: A2a=11.5; Ex-168: A2a=4.1; Ex-169: A2a=2.6; Ex-170: A2a=157; Ex-171:

A2a=30.4; Ex-172: A2a=13.3; Ex-173: A2a=22.6; Ex-174: A2a=37.5; Ex-175: A2a=5.6; Ex-176: A2a=8.9; Ex-177: A2a=12.7; Ex-178: A2a=19.3; Ex-180: A2a=1.1; Ex-181: A2a=19.9; Ex-182: A2a=10.2; Ex-183: A2a=5.0; Ex-184: A2a=16.4; Ex-185: A2a=5.7; Ex-186: A2a=3.5; Ex-187: A2a=5.8; Ex-188: A2a=12.6; Ex-189: A2a=3.1; Ex-190: A2a=6.7; Ex-191: A2a=8.2; Ex-192: A2a=153.1; Ex-193: A2a=127.8; Ex-194: A2a=24.8; Ex-195: A2a=41.6; Ex-196: A2a=95.7; Ex-197: A2a=32.4; Ex-198: A2a=8.25; Ex-199: A2a=10.8; Ex-200: A2a=15.6; Ex-201: A2a=50.2; Ex-202: A2a=29.1; Ex-203: A2a=8.5; Ex-204: A2a=11.5; Ex-205: A2a=4.1; Ex-206: A2a=30.9; Ex-207: A2a=144.8; Ex-208: A2a=143.1; Ex-209: A2a=9.4; Ex-210: A2a=7.7; Ex-211: A2a=9.9.

What is claimed is:

1. A compound of Formula A, or a pharmaceutically acceptable salt thereof:

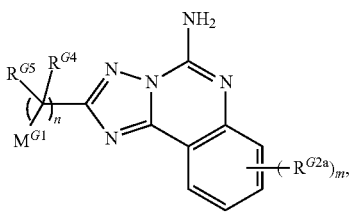

Formula A wherein:
"m" and "n" are independently an integer of from 1 to 3, with the proviso that no more than two $R^{G2a}$ substituents are located on adjacent ring carbon atoms;
$R^{G2a}$ is independently: (i) —OH; (ii) —CN; (iii) Halogen; (iv) —$C_{1-6}$-linear alkyl, optionally substituted by one or more fluorine atoms; or (v) —$C_{1-6}$-alkoxy, optionally substituted by a $C_{1-4}$-alkoxy moiety;
$R^{G4}$ and $R^{G5}$ are:
  (a) independently, for each occurrence, (i) —H; (ii) —F; or (iii) —$C_{1-6}$-alkyl which is optionally substituted with one or more fluorine substituents; or
  (b) $R^{G4}$ and $R^{G5}$ are taken together to form a carbonyl [—C(O)—] moiety, with the proviso that where "m">1, $R^{G4}$ and $R^{G5}$ are not selected to form two adjacent carbonyl moieties; and
$M^{G1}$ is a moiety of the formula:

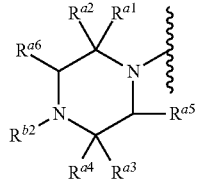

wherein:
$R^{a1}$, $R^{a2}$, $R^{a3}$, $R^{a4}$, $R^{a5}$, and $R^{a6}$, are defined as follows:
  (a) $R^{a6}$ is: —H; or —$CH_3$; and $R^{a1}$; $R^{a2}$; $R^{a3}$; $R^{a4}$; and $R^{a5}$ are independently:
    (i) —H;
    (ii) an aromatic moiety of from 6 to 10 carbon atoms; or
    (iii) —$C_{1-5}$ linear, branched or cyclic alkyl which is optionally substituted with one or more of —F or —$C_{1-4}$-alkyl substituent wherein one or more carbon atoms in said optional $C_{1-4}$-alkyl substituent are optionally substituted with one or more —F atoms; or
  (b) $R^{a1}$, $R^{a2}$, $R^{a3}$, and $R^{a4}$ are independently: —H, —$C_{1-5}$ linear, —$C_{3-5}$-branched or —$C_{3-5}$-cyclic alkyl; and $R^{a5}$ and $R^{a6}$ together form a bridge of the formula: —$(CH_2)_q$—, thereby providing a moiety of the structure:

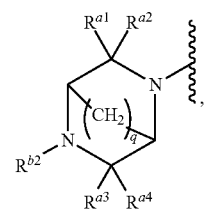

where "q" is 1 or 2;
  (c) one pair of $R^{a1}/R^{a2}$ or $R^{a3}/R^{a4}$ together form an oxo-functional group and the other pair are hydrogen, providing a structure of Formula Ga$^1$ or Ga$^2$:

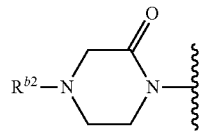

Formula Ga$^1$

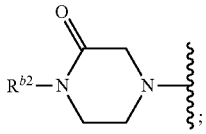

Formula Ga$^2$ (d) one pair of $R^{a1}/R^{a2}$ or $R^{a3}/R^{a4}$ are each —H and the other pair together comprise up to five carbon atoms which are cyclized to form a spirocyclo moiety of Formula Fb$^3$ or Formula Fb$^4$:

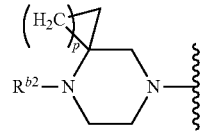

Formula Fb$^3$

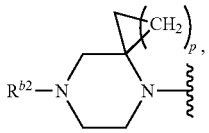

Formula Fb$^4$ wherein "p" is an integer from 1 to 3; or
  (e) $R^{a1}$, $R^{a2}$, $R^{a3}$, $R^{a4}$, $R^{a5}$, and $R^{a6}$ are selected to provide an ethylene-bridged moiety of the formula:

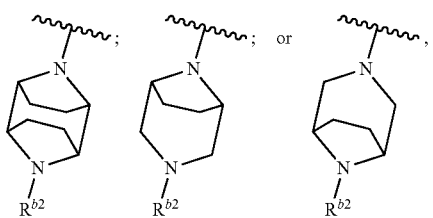

wherein: (i) $R^{a6}$ together with one of $R^{a3}$ or $R^{a4}$ form an ethylene bridge and any of $R^{a1}$, $R^{a2}$, $R^{a3}$, $R^{a4}$, or $R^{a5}$, which are not part of said ethylene bridge are hydrogen; (ii) $R^{a5}$ together with one of $R^{a1}$ or $R^{a2}$ form an ethylene bridge and any of $R^{a1}$, $R^{a2}$, $R^{a3}$, $R^{a4}$, or $R^{a6}$ which are not part of said ethylene bridge are hydrogen; or (iii) $R^{a6}$ together with one of $R^{a3}$ or $R^{a4}$, and $R^{a5}$ together with one of $R^{a1}$ or $R^{a2}$ each form ethylene bridge, and any of $R^{a1}$, $R^{a2}$, $R^{a3}$, or $R^{a4}$ which are not selected to form an ethylene bridge are hydrogen; and $R^{b2}$ is:
(a) $C_{1-6}$-linear, $C_{3-6}$-branched, or $C_{3-6}$-cyclic-alkyl, which alkyl moiety is optionally substituted with one or more substituents which are, independently: (i) halogen; (ii) $C_{1-6}$-alkoxy; or (iii) $C_{1-6}$-alkyl-SO$_2$—;
(b) —C(O)—$R^{c1}$ wherein, "$R^{c1}$" is: (i) aryl; (ii) $C_{1-6}$-alkoxy; or (iii) $C_{1-6}$-linear, $C_{3-6}$-branched, or $C_{3-6}$-cyclic-alkyl;
(c) a mono- or polycyclic aryl moiety comprising from 5 to 10 carbon atoms which is optionally linked to a nitrogen of the piperazine moiety through a carbonyl carbon, thereby forming an amide linkage, and wherein the ring of said aryl moiety optionally comprises one or more substituents which are, independently:
  (i) halogen;
  (ii) $C_{1-6}$-alkyl, optionally halogen substituted;
  (iii) $C_{1-6}$-alkoxy;
  (iv) $C_{1-6}$-alkoxy-$C_{1-6}$-alkoxide;
  (v) aryloxy of from 6 to 10 carbon atoms;
  (vi) $C_{1-6}$-heterocycloalkyl comprising from 1 to 3 heteroatoms which are, independently for each occurrence "N", "S", or "O", wherein said heterocycl-ring may optionally include a carbonyl group (C=O);
  (vii) $(R^{d1})_2N$—, wherein "$R^{d1}$" is independently —H or —$C_{1-6}$-alkyl;
  (viii) nitrile;
  (ix) mono- or polycyclic heteroaryl of from 5 to 10 carbon atoms, comprising from 1 to 4 heteroatoms which are, independently for each occurrence, "N", "O", or "S"; or
  (x) —C(O)—OH; or
(d) a mono- or polycyclic heteroaryl moiety comprising from 5 to 10 carbon atoms and from 1 to 4 heteroatoms which are independently for each occurrence, "N", "O", or "S", which is optionally linked to a nitrogen of the piperazine moiety through a carbonyl carbon, thereby forming an amide linkage, and wherein, optionally one or more ring carbon atoms is substituted with a moiety which is, independently for each occurrence:
  (i) —halogen;
  (ii) —$C_{1-6}$-alkyl-sulfonyl;
  (iii) —$C_{1-6}$-alkyl which is optionally substituted with one or more substituents that are, independently for each occurrence, halogen or $C_{1-6}$-alkoxide;
  (iv) —$C_{1-6}$-alkoxide which is optionally substituted with one or more substituents that are, independently for each occurrence, halogen or —$C_{1-6}$-alkyl;
  (v) $C_{1-6}$—C(O)—;
  (vi) —CN; or
  (vii) $C_{1-6}C(O)O$—.

2. A compound of Formula A, or a pharmaceutically acceptable salt thereof, having the structure of Formula AI:

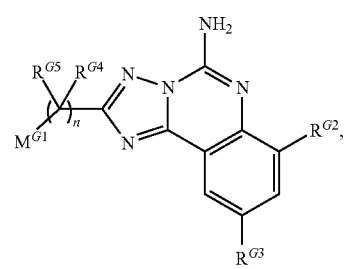

Formula AI wherein:
"n", $M^{G1}$, $R^{G4}$ and $R^{G5}$ are as defined for the compound of Formula A;
$R^{G2}$ is independently:
  (i) —OH;
  (ii) —CN;
  (iii) Halogen;
  (iv) —$C_{1-3}$-linear alkyl which is optionally substituted by one or more fluorine substituents; or
  (v) —$C_{1-6}$-alkoxy, which is optionally substituted by a $C_{1-4}$-alkoxy moiety; and
$R^{G3}$ is —H or —F.

3. A compound of claim 1 having the Formula CC1:

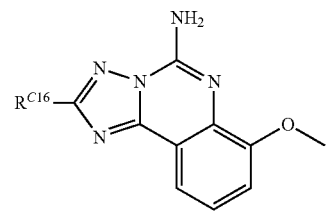

CC1, or a salt thereof, wherein R$^{e16}$ is:
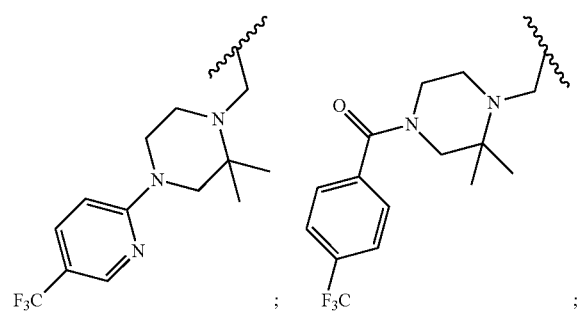
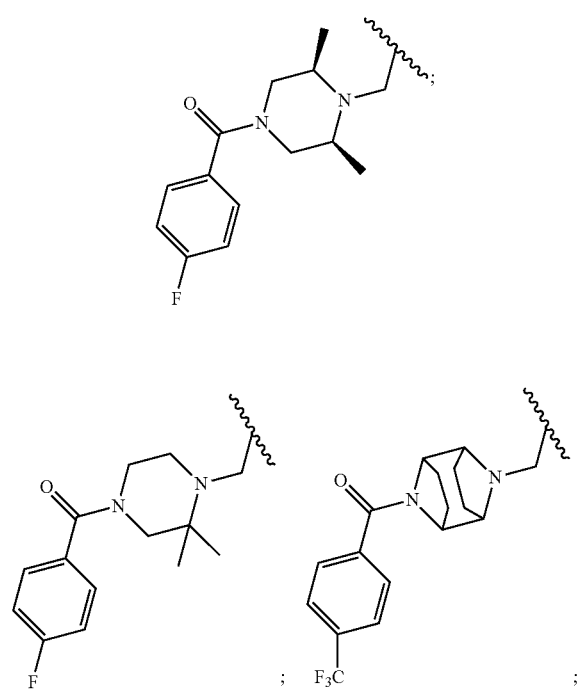
; or
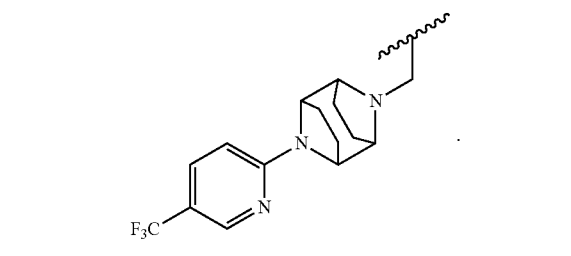
4. The compound of claim 1 having the Formula CC2:
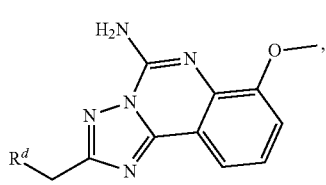
or a salt thereof,
wherein R$^d$ is:
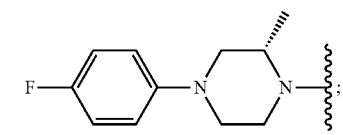
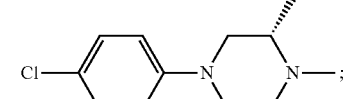
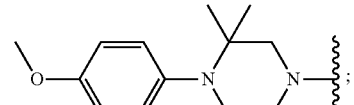
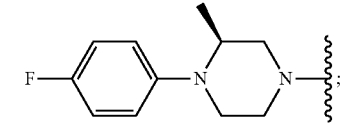
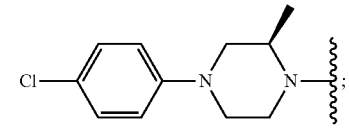
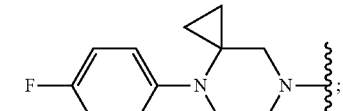
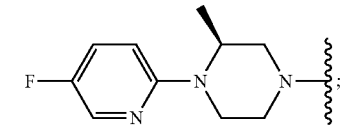
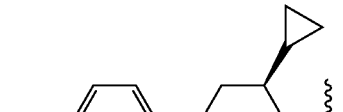
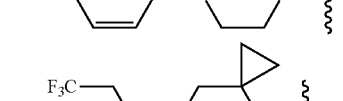
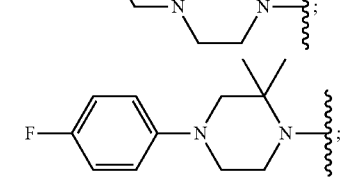

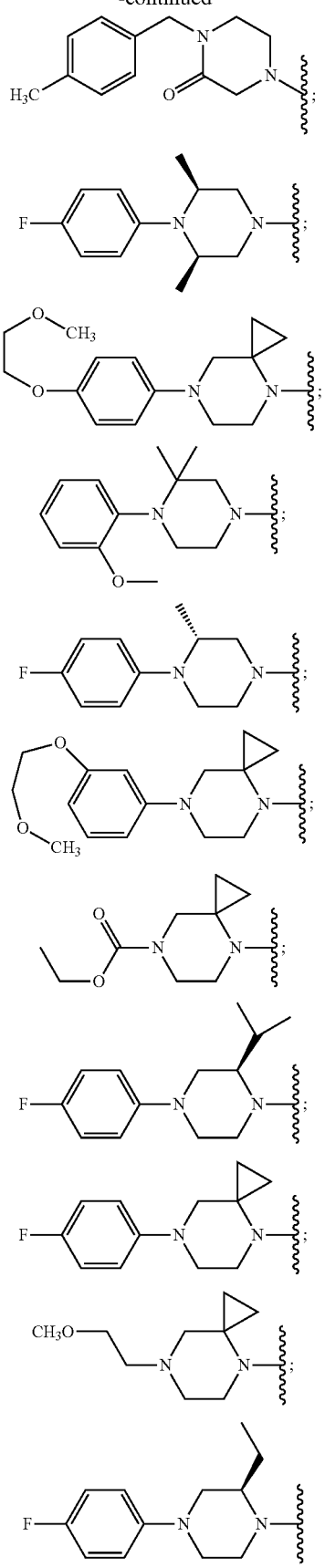
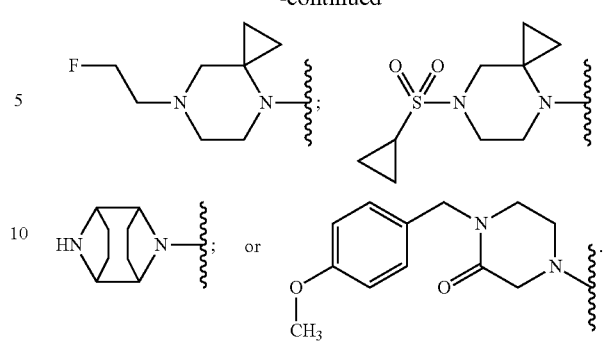
5. The compound of claim 1 having the Formula CC3:
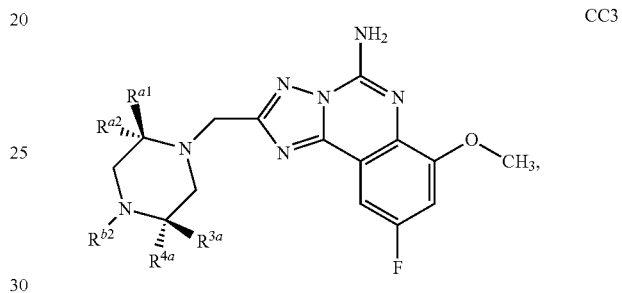
or a salt thereof,
wherein $R^{a1}$ to $R^{a4}$ and $R^{b2}$ are each defined in Table CTI.
TABLE CTI
| $R^{a1}/R^{a2}$ | $R^{a3}/R^{a4}$ | $R^{b2}$ |
|---|---|---|
| —CH₃/—H | —H/—H | 4-F-phenyl |
| —H/—CH₃ | —H/—H | 4-F-phenyl |
| —CH₃/—H | —H/—H | 5-F-pyridin-2-yl |
| —CH₃/—H | —H/—H | 5-CF₃-pyridin-2-yl |
| —H/—H | —CH₃/—H | 4-F-phenyl |

6. A compound of claim 1 having the Formula CC4:
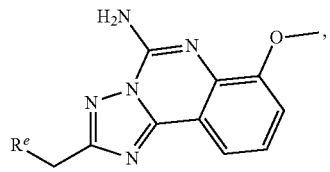
or a salt thereof,
wherein R$^e$ is:
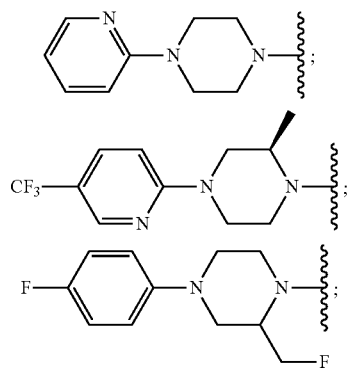
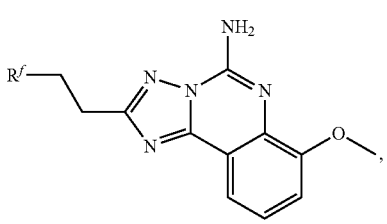
7. A compound of claim 1 having the Formula CC5:
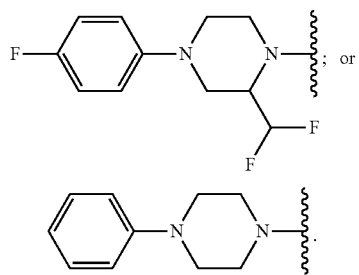
or a salt thereof,
where "R$^f$" is:
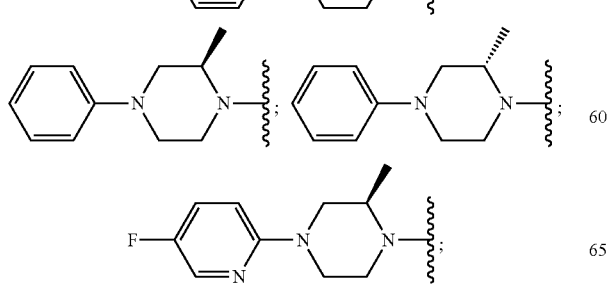

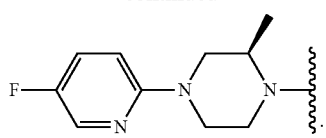
8. A compound of claim 1 having the Formula CC6:
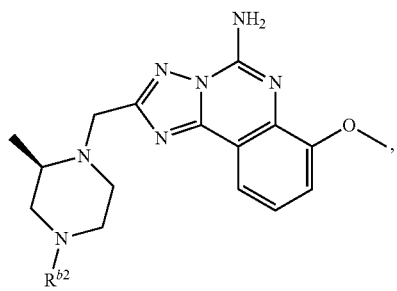
or a salt thereof,
  wherein $R^{b2}$ is:
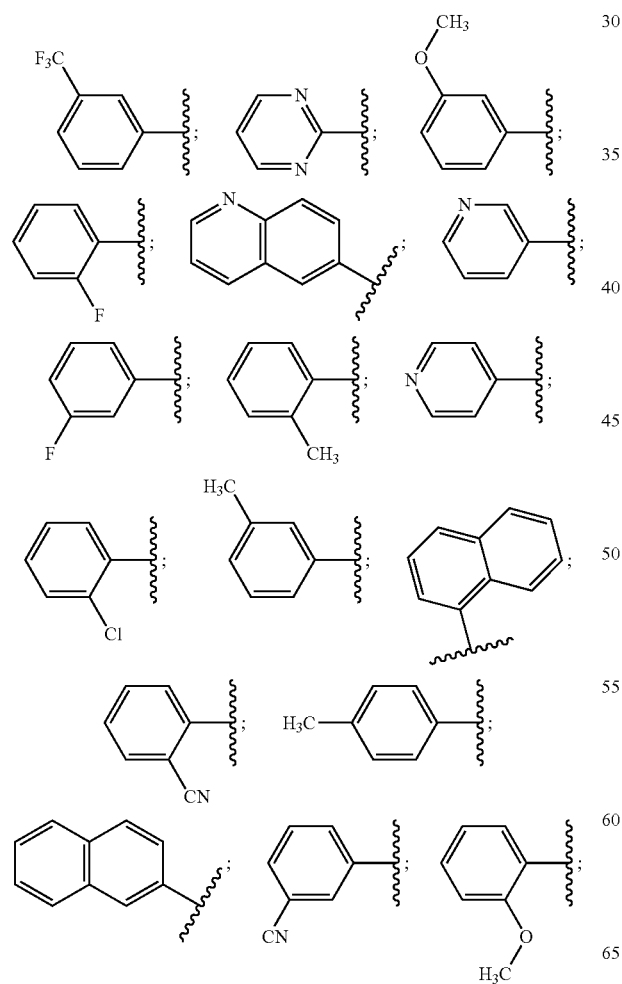
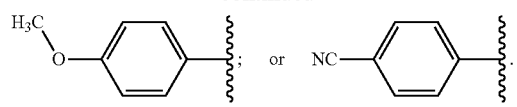
9. The compound of claim 1 having the Formula CC7:
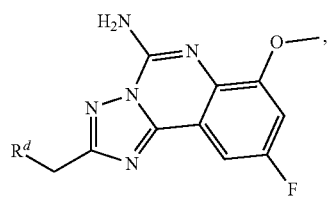
or a salt thereof,
  wherein $R^d$ is:
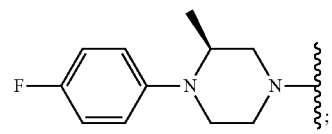
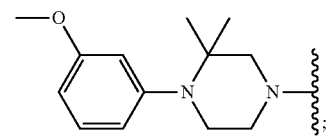
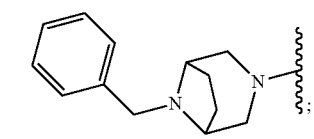
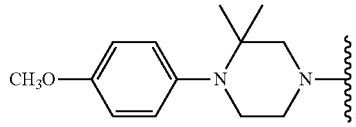
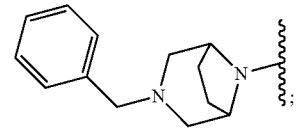
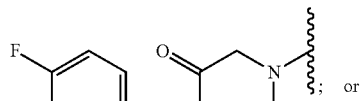
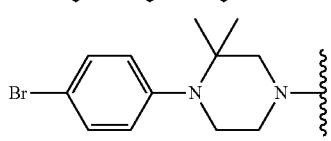

10. The following compounds, or a salt thereof:

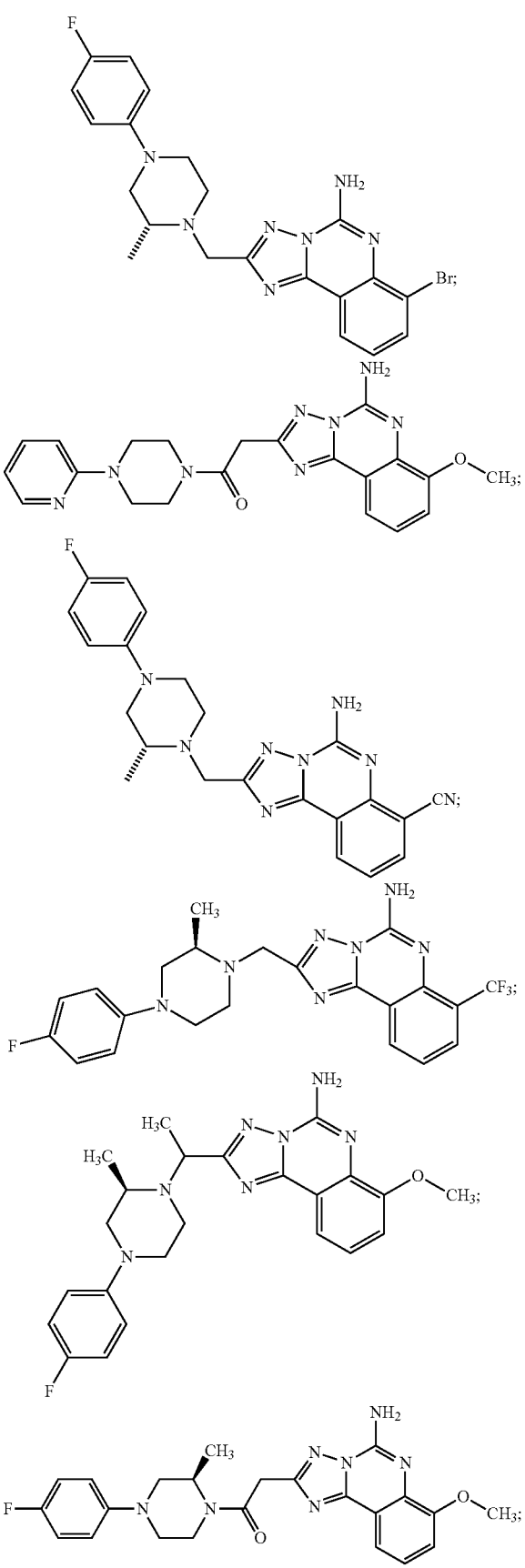

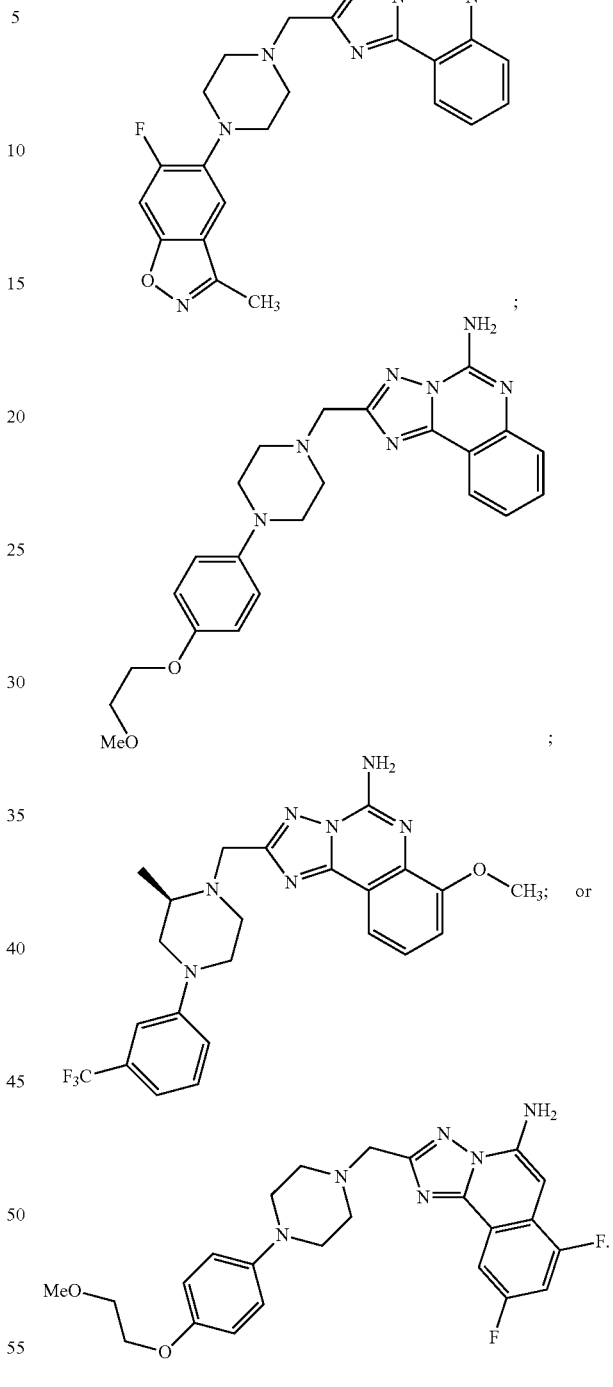

11. A method of treating a central nervous system disease by administering a compound of claim 1.

12. A pharmaceutical composition that comprises an inert carrier and a compound of claim 1, or a pharmaceutically acceptable salt thereof.

13. A compound of claim 1, or a pharmaceutically acceptable salt thereof, for use in medicine.

14. A method of treating a central nervous system disorder in a mammalian patient in need thereof by administering a therapeutically effective amount of a compound of claim 1, or a pharmaceutically acceptable salt thereof.

15. The method of claim 14 wherein said central nervous system disorder is a movement disorder associated with Parkinson's disease or the treatment thereof using dopaminergic therapy.

* * * * *